(12) United States Patent
Huh et al.

(10) Patent No.: US 10,193,080 B2
(45) Date of Patent: Jan. 29, 2019

(54) CONDENSED CYCLIC COMPOUND AND ORGANIC LIGHT-EMITTING DEVICE INCLUDING THE SAME

(71) Applicants: Samsung Electronics Co., Ltd., Suwon-si, Gyeonggi-do (KR); Samsung SDI Co., Ltd., Yongin-si, Gyeonggi-do (KR)

(72) Inventors: Dalho Huh, Suwon-si (KR); Miyoung Chae, Suwon-si (KR); Hyunjung Kim, Suwon-si (KR); Soonok Jeon, Seoul (KR); Yeonsook Chung, Seoul (KR); Yongsik Jung, Yongin-si (KR); Wook Kim, Suwon-si (KR); Jhunmo Son, Yongin-si (KR); Namheon Lee, Suwon-si (KR); Sangmo Kim, Hwaseong-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 217 days.

(21) Appl. No.: 14/804,898

(22) Filed: Jul. 21, 2015

(65) Prior Publication Data

US 2016/0118601 A1    Apr. 28, 2016

(30) Foreign Application Priority Data

Oct. 23, 2014 (KR) .................. 10-2014-0144278

(51) Int. Cl.
*H01L 51/50* (2006.01)
*H01L 51/00* (2006.01)
(Continued)

(52) U.S. Cl.
CPC ........ *H01L 51/0072* (2013.01); *C07D 209/88* (2013.01); *C07D 405/04* (2013.01);
(Continued)

(58) Field of Classification Search
None
See application file for complete search history.

(56) References Cited

U.S. PATENT DOCUMENTS 9,548,463 B2    1/2017 Yagi et al.
2010/0253212 A1 10/2010 Cheng et al.
(Continued)

FOREIGN PATENT DOCUMENTS

CN    103333158    *  7/2013    ........... C07D 409/14
CN    103232472 A    8/2013
(Continued)

*Primary Examiner* — Gregory D Clark
(74) *Attorney, Agent, or Firm* — Cantor Colburn LLP

(57) ABSTRACT

A condensed cyclic compound represented by Formulae 1A or 1B:

Formula 1A (Continued)

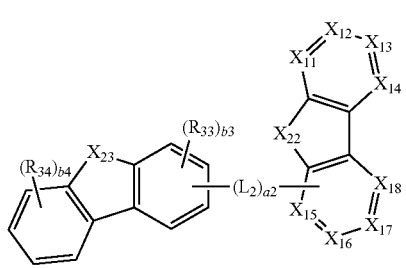

Formula 1B wherein in Formulae 1A and 1B, groups and variables are the same as described in the specification.

20 Claims, 1 Drawing Sheet

(51) Int. Cl.
  *C09K 11/02* (2006.01)
  *C07D 405/04* (2006.01)
  *C09K 11/06* (2006.01)
  *C07D 409/04* (2006.01)
  *C07D 209/88* (2006.01)
  *C07D 405/10* (2006.01)
  *C07D 471/04* (2006.01)

(52) U.S. Cl.
  CPC ......... *C07D 405/10* (2013.01); *C07D 409/04* (2013.01); *C07D 471/04* (2013.01); *C09K 11/025* (2013.01); *C09K 11/06* (2013.01); *H01L 51/0058* (2013.01); *H01L 51/0073* (2013.01); *H01L 51/0074* (2013.01); *H01L 51/0085* (2013.01); *C09K 2211/1007* (2013.01); *C09K 2211/1011* (2013.01); *C09K 2211/1022* (2013.01); *C09K 2211/1029* (2013.01); *C09K 2211/1044* (2013.01); *C09K 2211/1088* (2013.01); *C09K 2211/1092* (2013.01); *C09K 2211/185* (2013.01); *H01L 51/5012* (2013.01)

(56) References Cited

U.S. PATENT DOCUMENTS

| | | | |
|---|---|---|---|
| 2013/0234119 A1 | 9/2013 | Mizuki et al. | |
| 2013/0285035 A1* | 10/2013 | Taka | C09K 11/06 257/40 |
| 2014/0001451 A1* | 1/2014 | Mizuki | H01L 51/0067 257/40 |

FOREIGN PATENT DOCUMENTS

| | | |
|---|---|---|
| JP | 2011-213918 A | 10/2011 |
| JP | 2011256143 A | 12/2011 |
| JP | 201249518 A | 3/2012 |
| JP | 201289777 A | 5/2012 |
| KR | 1020100039393 A | 4/2010 |
| KR | 1020120031684 A | 4/2012 |
| KR | 1020120124429 A | 11/2012 |
| KR | 101224805 B1 | 1/2013 |
| KR | 10-2016-0011038 A | 1/2016 |
| WO | 2013060418 A1 | 5/2013 |

* cited by examiner

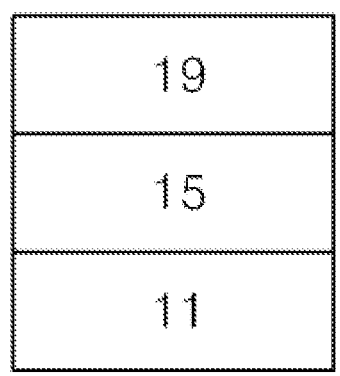

CONDENSED CYCLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2014-0144278, filed on Oct. 23, 2014, in the Korean Intellectual Property Office, the disclosure of which is incorporated herein in its entirety by reference

BACKGROUND

1. Field

The present disclosure relates to a condensed cyclic compound and an organic light-emitting device including the same.

2. Description of the Related Art

Organic light-emitting devices (OLEDs) are self-emission devices that have wide viewing angles, high contrast ratios, and short response times. In addition, OLEDs exhibit excellent brightness, driving voltage, and response speed characteristics, and produce multicolored images.

A typical organic light-emitting device includes an anode, a cathode, and an organic layer that is disposed between the anode and the cathode and includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and electrons are recombined in the emission layer to produce excitons. These excitons change from an excited state to a ground state, thereby generating light.

Various types of organic light emitting devices are known. However, there still remains a need in OLEDs having low driving voltage, high efficiency, high brightness, and long lifespan.

SUMMARY

Provided are novel condensed cyclic compounds and organic light-emitting devices including the same.

Additional aspects will be set forth in part in the description which follows and, in part, will be apparent from the description, or may be learned by practice of the presented exemplary embodiments.

According to an aspect of an exemplary embodiment, there is provided a condensed cyclic compound represented by Formulae 1A or 1B:

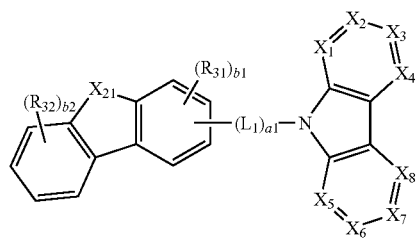

Formula 1A

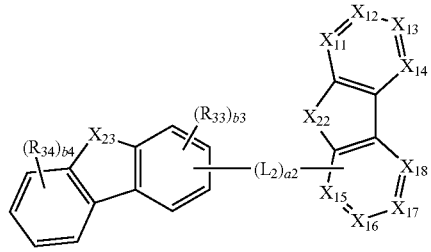

Formula 1B

In Formulae 1A and 1B, $X_1$ may be N or $C(R_1)$, $X_2$ may be N or $C(R_2)$, $X_3$ may be N or $C(R_3)$, $X_4$ may be N or $C(R_4)$, $X_5$ may be N or $C(R_5)$, $X_6$ may be N or $C(R_6)$, $X_7$ may be N or $C(R_7)$, $X_8$ may be N or $C(R_8)$, $X_{11}$ may be N or $C(R_{11})$, $X_{12}$ may be N or $C(R_{12})$, $X_{13}$ may be N or $C(R_{13})$, $X_{14}$ may be N or $C(R_{14})$, $X_{15}$ may be N, C, or $C(R_{15})$, $X_{16}$ may be N, C, or $C(R_{16})$, $X_{17}$ may be N, C, or $C(R_{17})$, and $X_{18}$ may be N, C or $C(R_{18})$, and when $X_{15}$ is C, $X_{15}$ may be connected with $*-(L_2)_{a2}-*'$, when $X_{16}$ is C, $X_{16}$ may be connected with $*-(L_2)_{a2}-*'$, $X_{17}$ is C, $X_{17}$ may be connected with $*-(L_2)_{a2}-*'$, and when $X_{18}$ is C, $X_{18}$ may be connected with $*-(L_2)_{a2}-*'$, $X_{21}$ may be selected from O, S, Se, $C(R_{21})(R_{22})$, $Si(R_{21})(R_{22})$, and $N(R_{23})$, $X_{22}$ may be selected from O, S, Se, $C(R_{24})(R_{25})$, $Si(R_{24})(R_{25})$, and $N(R_{26})$, $X_{23}$ may be selected from O, S, Se, $C(R_{27})(R_{28})$, $Si(R_{27})(R_{28})$, and $N(R_{29})$, $L_1$ and $L_2$ may be each independently selected from a phenylene group, a pyridinylene group, a fluorenylene group, a dibenzofuranylene group, and a dibenzothiophenylene group;

a phenylene group, a pyridinylene group, a fluorenylene group, a dibenzofuranylene group, and a dibenzothiophenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —$Si(Q_1)(Q_2)(Q_3)$, and —$Si(R_{41})(R_{42})$—, —O—, —S—, and —Se—, wherein a1 and a2 may be each independently an integer selected from 0 to 5, and when a1 is 2 or more, 2 or more groups $L_1$ may be identical to or different from each other, and when a2 is 2 or more, 2 or more groups $L_2$ may be identical to or different from each other, $R_1$ to $R_8$, $R_{11}$ to $R_{18}$, and $R_{31}$ to $R_{34}$ may be each independently selected from a hydrogen, a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a phenyl group, a pyridinyl group, a fluorenyl group, a dibenzofuranyl group, and a dibenzothiophenyl group, a phenyl group, a pyridinyl group, a fluorenyl group, a dibenzofuranyl group, and a dibenzothiophenyl group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —Si($Q_{11}$)($Q_{12}$)($Q_{13}$), and —Si($Q_{21}$)($Q_{22}$)($Q_{23}$), and b1 and b3 may be each independently 1, 2, or 3, and b2 and b4 may be each independently 1, 2, 3, or 4, and when b1 is 2 or more, 2 or more groups $R_{31}$ may be identical to or different from each other, when b2 is 2 or more, 2 or more groups $R_{32}$ may be identical to or different from each other, when b3 is 2 or more, 2 or more groups $R_{33}$ may be identical to or different from each other, and when b4 is 2 or more, 2 or more groups $R_{34}$ may be identical to or different from each other.

In Formula 1A, i) at least one of $X_3$ and $X_7$ may be C(CN), ii) at least one of groups $R_{31}$ in the number of b1 and groups $R_{32}$ in the number of b2 may be a cyano group, or iii) at least one of $X_3$ and $X_7$ may be C(CN) and at least one of groups $R_{31}$ in the number of b1 and groups $R_{32}$ in the number of b2 may be a cyano group.

In Formula 1B, i) at least one of $X_{13}$ and $X_{17}$ may be C(CN), ii) at least one of groups $R_{33}$ in the number of b3 and groups $R_{34}$ in the number of b4 may be a cyano group, or iii) at least one of $X_{13}$ and $X_{17}$ may be C(CN) and at least one of groups $R_{33}$ in the number of b3 and groups $R_{34}$ in the number of b4 may be a cyano group.

In Formula 1B, when $X_{22}$ is N($R_{26}$) and $X_{23}$ is N($R_{29}$), a2 is not 0.

In Formulae 1A and 1B, $R_{21}$ to $R_{29}$, $R_{41}$, $R_{42}$, $Q_1$ to $Q_3$, $Q_{11}$ to $Q_{13}$, and $Q_{21}$ to $Q_{23}$ may be each independently selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a pyridinyl group, a fluorenyl group, a dibenzofuranyl group, and a dibenzothiophenyl group; and a phenyl group, a pyridinyl group, a fluorenyl group, a dibenzofuranyl group, and a dibenzothiophenyl group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group.

According to another aspect of an exemplary embodiment, there is provided an organic light-emitting device including:

a first electrode;

a second electrode; and an organic layer disposed between the first electrode and the second electrode, wherein the organic layer includes an emission layer and at least one condensed cyclic compound of Formulae 1A or 1B.

BRIEF DESCRIPTION OF THE DRAWINGS

These and/or other aspects will become apparent and more readily appreciated from the following description of the embodiments, taken in conjunction with the accompanying drawings in which:

FIG. 1 is a schematic cross-sectional view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

According to an aspect, provided is a condensed cyclic compound represented by Formulae 1A or 1B below:

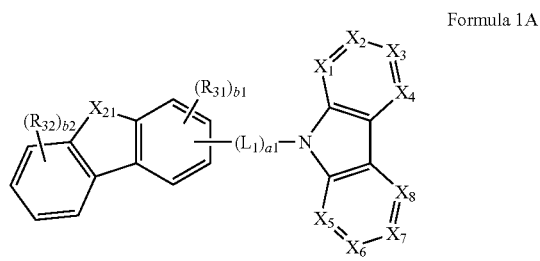

Formula 1A

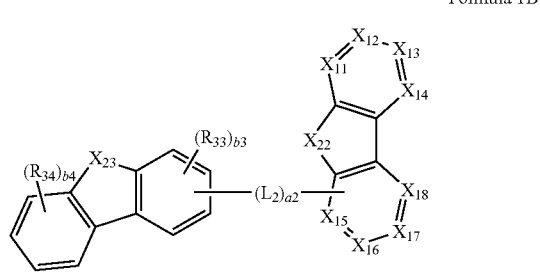

Formula 1B

In Formulae 1A or 1B, $X_1$ may be N or $C(R_1)$, $X_2$ may be N or $C(R_2)$, $X_3$ may be N or $C(R_3)$, $X_4$ may be N or $C(R_4)$, $X_5$ may be N or $C(R_5)$, $X_6$ may be N or $C(R_6)$, $X_7$ may be N or $C(R_7)$, $X_8$ may be N or $C(R_8)$, $X_{11}$ may be N or $C(R_{11})$, $X_{12}$ may be N or $C(R_{12})$, $X_{13}$ may be N or $C(R_{13})$, $X_{14}$ may be N or $C(R_{14})$, $X_{15}$ may be N, C, or $C(R_{15})$, $X_{16}$ may be N, C, or $C(R_{16})$, $X_{17}$ may be N, C, or $C(R_{17})$, and $X_{18}$ may be N, C, or $C(R_{18})$, and when $X_{15}$ is C, $X_{15}$ may be connected with *-$(L_2)_{a2}$-*', when $X_{16}$ is C, $X_{16}$ may be connected with *-$(L_2)_{a2}$-*', when $X_{17}$ is C, $X_{17}$ may be connected with *-$(L_2)_{a2}$-*', and when $X_{18}$ is C, $X_{18}$ may be connected with *-$(L_2)_{a2}$-*'.

For example, in Formulae 1A and 1B, $X_1$ may be $C(R_1)$, $X_2$ may be $C(R_2)$, $X_3$ may be $C(R_3)$, $X_4$ may be $C(R_4)$, $X_5$ may be $C(R_5)$, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, and $X_{14}$ may be $C(R_{14})$, but embodiments are not limited thereto.

In an embodiment, in Formula 1A, $X_1$ may be N, $X_2$ may be $C(R_2)$, $X_3$ may be N, $X_4$ may be $C(R_4)$, $X_5$ may be $C(R_5)$, $X_6$ may be $C(R_6)$, $X_7$ may be $C(R_7)$, and $X_8$ may be $C(R_8)$.

In an embodiment, in Formula 1A, $X_1$ may be $C(R_1)$, $X_2$ may be N, $X_3$ may be $C(R_3)$, $X_4$ may be N, $X_5$ may be $C(R_5)$, $X_6$ may be $C(R_6)$, $X_7$ may be $C(R_7)$, and $X_8$ may be $C(R_8)$.

In an embodiment, in Formula 1B, $X_{11}$ may be N, $X_{12}$ may be $C(R_{12})$, $X_{13}$ may be N, and $X_{14}$ may be $C(R_{14})$.

In an embodiment, in Formula 1B, $X_{11}$ may be $C(R_{11})$, $X_{12}$ may be N, $X_{13}$ may be $C(R_{13})$, and $X_{14}$ may be N.

In an embodiment, in Formulae 1A and 1B, $X_1$ may be N or $C(R_1)$, $X_2$ may be N or $C(R_2)$, $X_3$ may be N or $C(R_3)$, $X_4$ may be N or $C(R_4)$, $X_5$ may be N or $C(R_5)$, $X_6$ may be N or $C(R_6)$, $X_7$ may be N or $C(R_7)$, $X_8$ may be N or $C(R_8)$, $X_{11}$ may be N or $C(R_{11})$, $X_{12}$ may be N or $C(R_{12})$, $X_{13}$ may be N or $C(R_{13})$, and $X_{14}$ may be N or $C(R_{14})$. In Formula 1A, $R_1$, $R_2$, $R_4$, $R_5$, $R_6$, and $R_8$ may not be a cyano group, and in Formula 1B, $R_{11}$, $R_{12}$, and $R_{14}$ may not be a cyano group.

In Formulae 1A and 1B,
$X_{21}$ may be selected from O, S, Se, $C(R_{21})(R_{22})$, $Si(R_{21})(R_{22})$, and $N(R_{23})$,
$X_{22}$ may be selected from O, S, Se, $C(R_{24})(R_{25})$, $Si(R_{24})(R_{25})$, and $N(R_{26})$, and
$X_{23}$ may be selected from O, S, Se, $C(R_{27})(R_{28})$, $Si(R_{27})(R_{28})$, and $N(R_{29})$, wherein $R_{21}$ to $R_{29}$ may be understood by referring to the description provided herein.

For example, in Formulae 1A and 1B,
$X_{21}$ may be selected from O, S, $C(R_{21})(R_{22})$, and $N(R_{23})$;
$X_{22}$ may be selected from O, S, $C(R_{24})(R_{25})$, and $N(R_{26})$; and
$X_{23}$ may be selected from O, S, $C(R_{27})(R_{28})$, and $N(R_{29})$,
wherein $R_{21}$, $R_{22}$, $R_{24}$, $R_{25}$, $R_{27}$, and $R_{28}$ may be each independently selected from
a $C_1$-$C_{20}$ alkyl group and a $C_1$-$C_{20}$ alkoxy group;
a $C_1$-$C_{20}$ alkyl group and a $C_1$-$C_{20}$ alkoxy group, each substituted with at least one of a deuterium, —F and a cyano group;
a phenyl group, a pyridinyl group, a fluorenyl group, a dibenzofuranyl group, and a dibenzothiophenyl group; and
a phenyl group, a pyridinyl group, a fluorenyl group, a dibenzofuranyl group, and a dibenzothiophenyl group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group, and
wherein $R_{23}$, $R_{26}$, and $R_{29}$ may be each independently selected from a phenyl group, a pyridinyl group, a fluorenyl group, a dibenzofuranyl group, and a dibenzothiophenyl group; and a phenyl group, a pyridinyl group, a fluorenyl group, a dibenzofuranyl group, and a dibenzothiophenyl group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group.

In an embodiment, in Formulae 1A and 1B, $X_{21}$ may be selected from O, S, $C(R_{21})(R_{22})$, and $N(R_{23})$;

$X_{22}$ may be selected from O, S, $C(R_{24})(R_{25})$, and $N(R_{26})$; and $X_{23}$ may be selected from O, S, $C(R_{27})(R_{28})$, and $N(R_{29})$, wherein $R_{21}$, $R_{22}$, $R_{24}$, $R_{25}$, $R_{27}$, and $R_{28}$ may be each independently selected from a $C_1$-$C_{10}$ alkyl group, a $C_1$-$C_{10}$ alkoxy group, a phenyl group, a pyridinyl group, a fluorenyl group, a dibenzofuranyl group, and a dibenzothiophenyl group, and wherein $R_{23}$, $R_{26}$, and $R_{29}$ may be each independently selected from a phenyl group, a pyridinyl group, a fluorenyl group, a dibenzofuranyl group, and a dibenzothiophenyl group, but embodiments are not limited thereto.

In Formulae 1A and 1B, $L_1$ and $L_2$ may be each independently selected from a phenylene group, a pyridinylene group, a fluorenylene group, a dibenzofuranylene group, and a dibenzothiophenylene group;

a phenylene group, a pyridinylene group, a fluorenylene group, a dibenzofuranylene group, and a dibenzothiophenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —$Si(Q_1)(Q_2)(Q_3)$; and —$Si(R_{41})(R_{42})$—, —O—, —S— and —Se—.

In Formulae 1A and 1B, $Q_1$ to $Q_3$, $R_{41}$, and $R_{42}$ may be understood by referring to the description provided herein.

In Formula 1A, a1 may indicate the number of groups $L_1$, and may be an integer selected from 0 to 5. When a1 is 0, *-$(L_1)_{a1}$-*' is a single bond. When a1 is 2 or more, 2 or more groups $L_1$ may be identical to or different from each other. In an embodiment, a1 may be 0, 1, or 2. For example, a1 may be 0 or 1, but embodiments are not limited thereto.

In Formula 1B, a2 may indicate the number of groups $L_2$, and may be an integer selected from 0 to 5. When a2 is 0, *-$(L_2)_{a2}$-*' is a single bond. When a2 is 2 or more, 2 or more groups $L_2$ may be identical to or different from each other. In an embodiment, a2 may be 0, 1, or 2. For example, a2 may be 0 or 1, but embodiments are not limited thereto.

In an embodiment, in Formulae 1A and 1B, a1 and a2 may not be 0, and $L_1$ and $L_2$ may be selected from groups represented by Formulae 2-1 to 2-18 below:

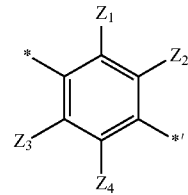

Formula 2-1

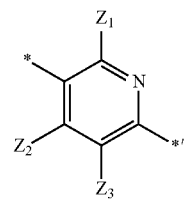

Formula 2-2

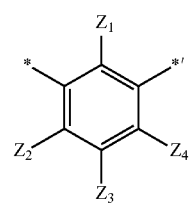

Formula 2-3

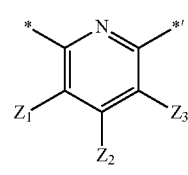

Formula 2-4

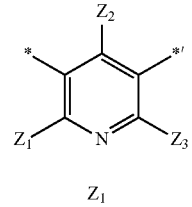

Formula 2-5

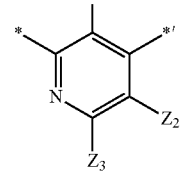

Formula 2-6

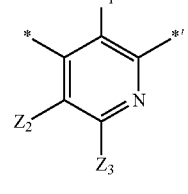

Formula 2-7

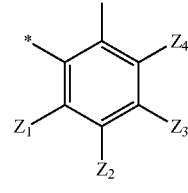

Formula 2-6

-continued

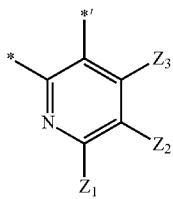
Formula 2-7

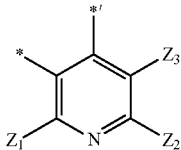
Formula 2-8

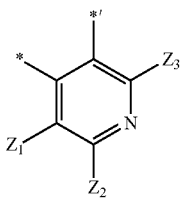
Formula 2-9

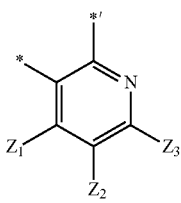
Formula 2-10

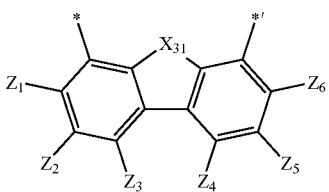
Formula 2-11

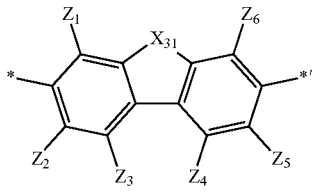
Formula 2-12

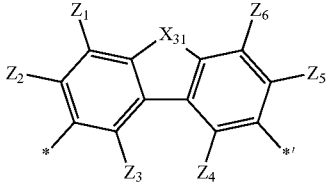
Formula 2-13

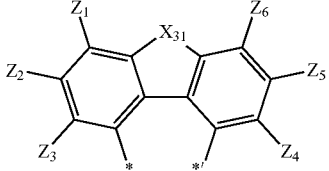
Formula 2-14

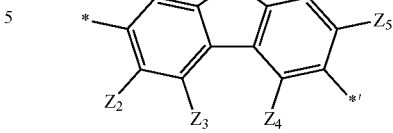
Formula 2-15

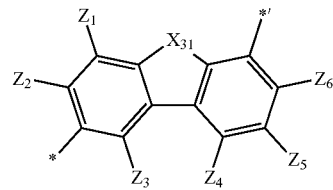
Formula 2-16

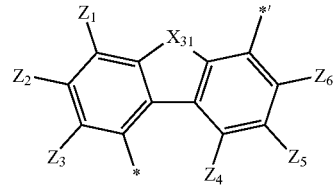
Formula 2-17

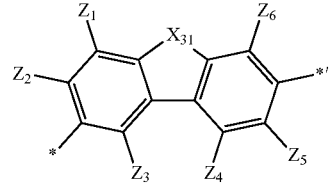
Formula 2-18

In Formulae 2-1 to 2-18, $X_{31}$ may be O, S, or $C(Z_7)(Z_8)$, $Z_1$ to $Z_8$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —Si($Q_1$)($Q_2$)($Q_3$), wherein $Q_1$ to $Q_3$ may be each independently selected from a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group.

For example, in Formulae 2-1 to 2-18, $Z_1$ to $Z_6$ may be each independently selected from a hydrogen, a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a pyridinyl group, a fluorenyl group, a dibenzofuranyl group, and a dibenzothiophenyl group, and $Z_7$ and $Z_8$ may be each independently selected from a $C_1$-$C_{10}$ alkyl group, a $C_1$-$C_{10}$ alkoxy group, a phenyl group, a pyridinyl group, a fluorenyl group, a dibenzofuranyl group, and a dibenzothiophenyl group, but embodiments are not limited thereto.

In another embodiment, groups $L_1$ in the number of a1 in Formula 1A may include at least one of the groups of Formulae 2-3 to 2-18 above, and groups $L_2$ in the number of a2 in Formula 1B may include at least one of the groups of Formulae 2-3 to 2-18 above.

In an embodiment, a1 and a2 may be 0; or a1 and a2 may be 1, and $L_1$ and $L_2$ may be the group of Formula 2-3 above, but embodiments are not limited thereto.

In Formulae 1A and 1B, $R_1$ to $R_8$, $R_{11}$ to $R_{18}$, and $R_{31}$ to $R_{34}$ may be each independently selected from a hydrogen, a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a pyridinyl group, a fluorenyl group, a dibenzofuranyl group, and a dibenzothiophenyl group;

a phenyl group, a pyridinyl group, a fluorenyl group, a dibenzofuranyl group, and a dibenzothiophenyl group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —Si($Q_{11}$)($Q_{12}$)($Q_{13}$), and —Si($Q_{21}$)($Q_{22}$)($Q_{23}$), wherein $Q_{11}$ to $Q_{13}$ and $Q_{21}$ to $Q_{23}$ may be understood by referring to the description provided herein.

In Formula 1A, b1 may indicate the number of groups $R_{31}$, and may be 1, 2, or 3. When b1 is 2 or more, 2 or more groups $R_{31}$ may be identical to or different from each other. In an embodiment, b1 may be 1 or 2. For example, b1 may be 1, but embodiments are not limited thereto.

In Formula 1A, b2 may indicate the number of groups $R_{32}$, and may be 1, 2, 3, or 4. When b2 is 2 or more, 2 or more groups $R_{32}$ may be identical to or different from each other. In an embodiment, b2 may be 1 or 2. For example, b2 may be 1, but embodiments are not limited thereto.

In Formula 1B, b3 may indicate the number of groups $R_{33}$, and may be 1, 2, or 3. When b3 is 2 or more, 2 or more groups $R_{33}$ may be identical to or different from each other. In an embodiment, b3 may be 1 or 2. For example, b3 may be 1, but embodiments are not limited thereto.

In Formula 1B, b4 may indicate the number of groups $R_{34}$, and may be 1, 2, 3, or 4. When b4 is 2 or more, 2 or more groups $R_{34}$ may be identical to or different from each other. In an embodiment, may be 1 or 2. For example, b4 may be 1, but embodiments are not limited thereto.

For example, in Formulae 1A and 1B, $R_1$ to $R_8$, $R_{11}$ to $R_{18}$, and $R_{31}$ to $R_{34}$ may be each independently selected from a hydrogen, a deuterium, —F, a hydroxyl group, a cyano group, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one of a deuterium, —F, a hydroxyl group, and a cyano group;

a phenyl group, a pyridinyl group, a fluorenyl group, a dibenzofuranyl group, and a dibenzothiophenyl group;

a phenyl group, a pyridinyl group, a fluorenyl group, a dibenzofuranyl group, and a dibenzothiophenyl group, each substituted with at least one of a deuterium, —F, a hydroxyl group, a cyano group, a $C_1$-$C_{10}$ alkyl group, a $C_1$-$C_{10}$ alkoxy group, a phenyl group, a pyridinyl group, a fluorenyl group, a dibenzofuranyl group, a dibenzothiophenyl group, and —Si($Q_{11}$)($Q_{12}$)($Q_{13}$); and —Si($Q_{21}$)($Q_{22}$)($Q_{23}$), wherein $Q_{11}$ to $Q_{13}$ and $Q_{21}$ to $Q_{23}$ may be each independently selected from a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group.

In Formula 1A, i) at least one of $X_3$ and $X_7$ may be C(CN), ii) at least one of groups $R_{31}$ in the number of b1 and groups $R_{32}$ in the number of b2 may be a cyano group, or iii) at least one of $X_3$ and $X_7$ may be C(CN) and at least one of groups $R_{31}$ in the number of b1 and groups $R_{32}$ in the number of b2 may be a cyano group.

In Formula 1B, i) at least one of $X_{13}$ and $X_{17}$ may be C(CN), ii) at least one of groups $R_{33}$ in the number of b3 and groups $R_{34}$ in the number of b4 may be a cyano group, or iii) at least one of $X_{13}$ and $X_{17}$ may be C(CN) and at least one of groups $R_{33}$ in the number of b3 and groups $R_{34}$ in the number of b4 may be a cyano group.

In an embodiment, in Formulae 1A and 1B, $R_1$, $R_2$, $R_4$, $R_5$, $R_6$, $R_8$, $R_{11}$, $R_{12}$, $R_{14}$, $R_{15}$, $R_{16}$, and $R_{18}$ may be each independently selected from a hydrogen, a deuterium, —F, a hydroxyl group, a $C_1$-$C_{10}$ alkyl group, a $C_1$-$C_{10}$ alkoxy group, a phenyl group, a pyridinyl group, a fluorenyl group, a dibenzofuranyl group, a dibenzothiophenyl group, and —Si($Q_{21}$)($Q_{22}$)($Q_{23}$), wherein $Q_{21}$ to $Q_{23}$ may be each independently selected from a $C_1$-$C_{10}$ alkyl group, a $C_1$-$C_{10}$ alkoxy group, a phenyl group, a pyridinyl group, a fluorenyl group, a dibenzofuranyl group, and a dibenzothiophenyl group.

In another embodiment, in Formulae 1A and 1B, $R_1$, $R_2$, $R_4$, $R_5$, $R_6$, $R_8$, $R_{11}$, $R_{12}$, $R_{14}$, $R_{15}$, $R_{16}$, and $R_{18}$ may be each independently selected from a hydrogen and —Si($Q_{21}$)($Q_{22}$)($Q_{23}$), wherein $Q_{21}$ to $Q_{23}$ may be each independently selected from a $C_1$-$C_{10}$ alkyl group, a $C_1$-$C_{10}$ alkoxy group, a phenyl group, a pyridinyl group, a fluorenyl group, a dibenzofuranyl group, and a dibenzothiophenyl group.

In an embodiment, in Formulae 1A and 1B, $R_1$, $R_2$, $R_4$, $R_5$, $R_6$, $R_8$, $R_{11}$, $R_{12}$, $R_{14}$, $R_{15}$, $R_{16}$, and $R_{18}$ may be a hydrogen.

In an embodiment, in Formulae 1A and 1B, $R_3$, $R_7$, $R_{13}$, and $R_{17}$ may be each independently selected from a hydrogen, a deuterium, —F, a hydroxyl group, a cyano group, a $C_1$-$C_{10}$ alkyl group, a $C_1$-$C_{10}$ alkoxy group, a phenyl group, a pyridinyl group, a fluorenyl group, a dibenzofuranyl group, a dibenzothiophenyl group, and —Si($Q_{21}$)($Q_{22}$)($Q_{23}$), wherein $Q_{21}$ to $Q_{23}$ may be each independently selected from a $C_1$-$C_{10}$ alkyl group, a $C_1$-$C_{10}$ alkoxy group, a phenyl group, a pyridinyl group, a fluorenyl group, a dibenzofuranyl group, and a dibenzothiophenyl group. At least one of $R_3$ and $R_7$ in Formula 1A may be a cyano group, and at least one of $R_{13}$ and $R_{17}$ in Formula 1B may be a cyano group.

In an embodiment, at least one of groups $R_{32}$ in the number of b2 in Formula 1A may be a cyano group.

In an embodiment, in Formulae 1A and 1B, $R_{31}$ to $R_{34}$ may be each independently selected from a hydrogen, a deuterium, —F, a hydroxyl group, a cyano group, a $C_1$-$C_{10}$ alkyl group, a $C_1$-$C_{10}$ alkoxy group, a phenyl group, a pyridinyl group, a fluorenyl group, a dibenzofuranyl group, a dibenzothiophenyl group, and —Si($Q_{21}$)($Q_{22}$)($Q_{23}$), wherein $Q_{21}$ to $Q_{23}$ may be each independently selected from a $C_1$-$C_{10}$ alkyl group, a $C_1$-$C_{10}$ alkoxy group, a phenyl group, a pyridinyl group, a fluorenyl group, a dibenzofuranyl group, and a dibenzothiophenyl group.

In an embodiment, in Formulae 1A and 1B, $R_{31}$ to $R_{34}$ may be each independently a hydrogen, a cyano group, and —Si($Q_{21}$)($Q_{22}$)($Q_{23}$), wherein $Q_{21}$ to $Q_{23}$ may be each independently selected from a $C_1$-$C_{10}$ alkyl group, a $C_1$-$C_{10}$ alkoxy group, a phenyl group, a pyridinyl group, a fluorenyl group, a dibenzofuranyl group, and a dibenzothiophenyl group.

For example, the condensed cyclic compound may be represented by one of Formulae 1A(1) to 1A(4) below:

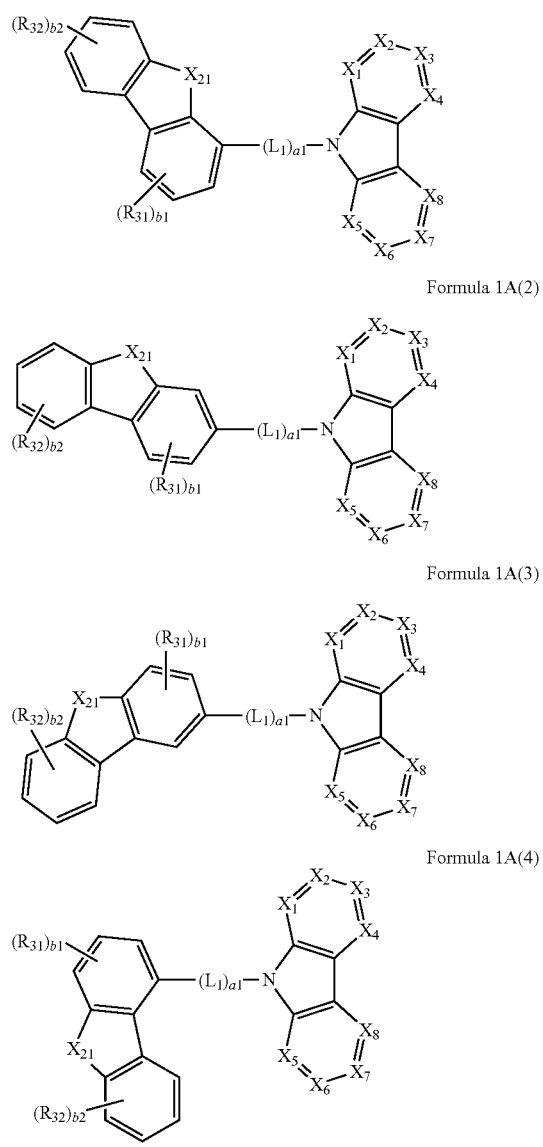

In Formulae 1A(1) to 1A(4), $X_1$ to $X_8$, $X_{21}$, $L_1$, a1, $R_{31}$, $R_{32}$, b1, and b2 may be understood by referring to the description provided herein.

For example, the condensed cyclic compound may be represented by one of Formulae 1A-A to 1A-D below:

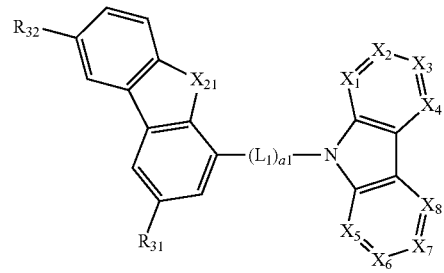

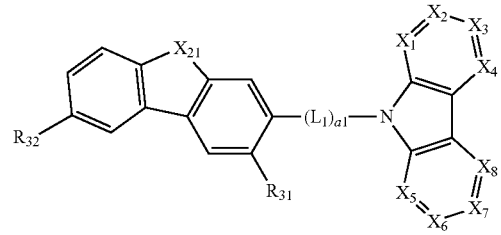

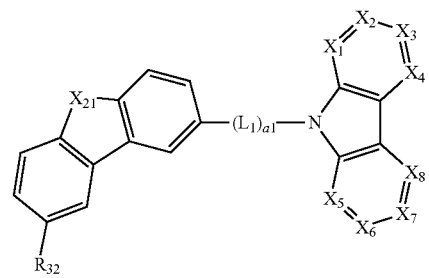

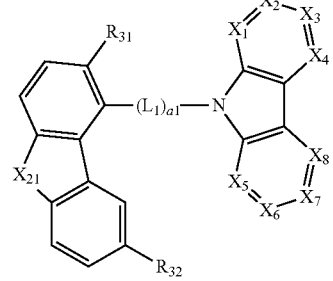

In Formulae 1A-A to 1A-D, $X_1$ to $X_8$, $X_{21}$, $L_1$, a1, $R_{31}$, and $R_{32}$ may be understood by referring to the description provided herein.

For example, in Formulae 1A-A to 1A-D, i) at least one of $X_3$ and $X_7$ may be C(CN), ii) at least one of $R_{31}$ and $R_{32}$ may be a cyano group, or iii) at least one of $X_3$ and $X_7$ may be C(CN) and at least one of $R_{31}$ and $R_{32}$ may be a cyano group.

For example, the condensed cyclic compound may be represented by one of Formulae 1B(1) to 1B(16) below:

Formula 1B(1)
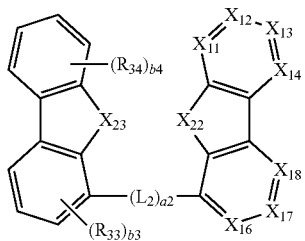
Formula 1B(2)
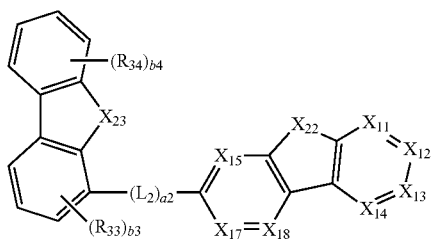
Formula 1B(3)
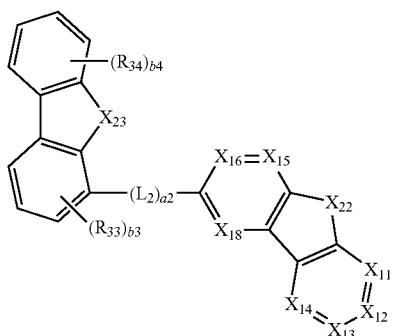
Formula 1B(4)
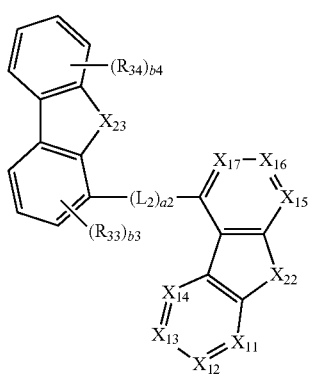
Formula 1B(5)
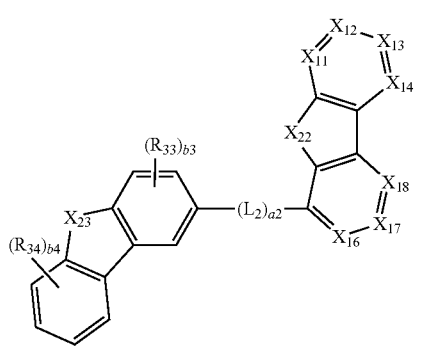
Formula 1B(6)
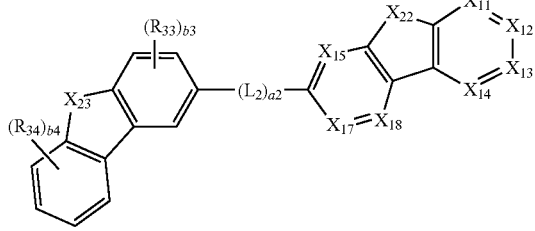
Formula 1B(7)
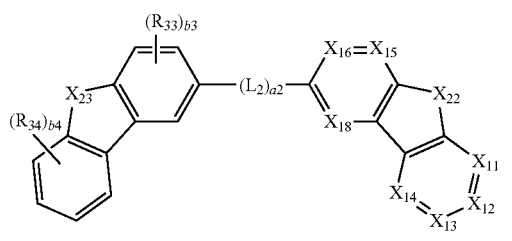
Formula 1B(8)
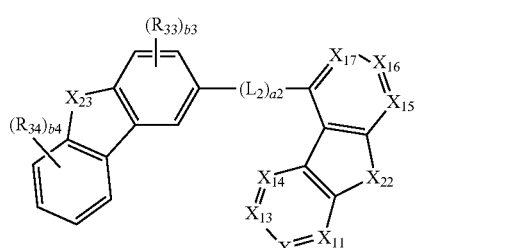
Formula 1B(9)
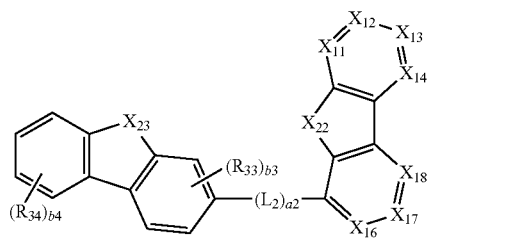
Formula 1B(10)
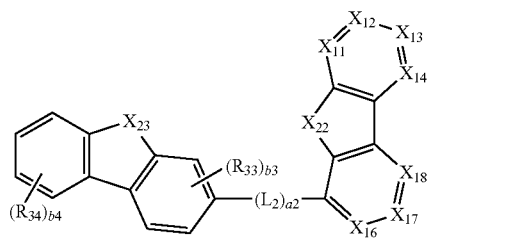
Formula 1B(11)
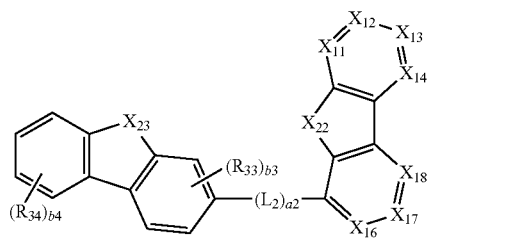

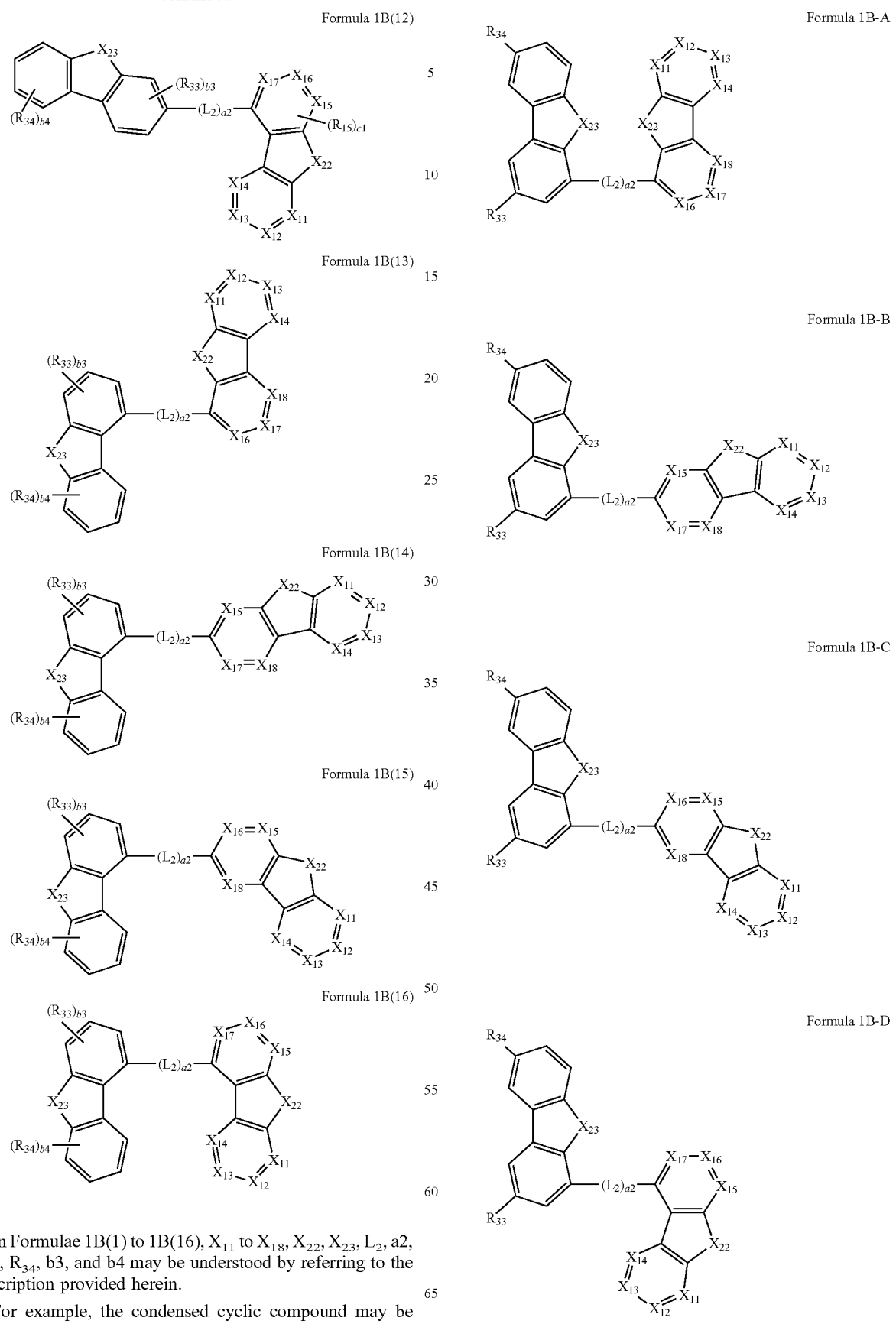
In Formulae 1B(1) to 1B(16), $X_{11}$ to $X_{18}$, $X_{22}$, $X_{23}$, $L_2$, a2, $R_{33}$, $R_{34}$, b3, and b4 may be understood by referring to the description provided herein.
For example, the condensed cyclic compound may be represented by one of Formulae 1B-A to 1B-P below:

Formula 1B-E
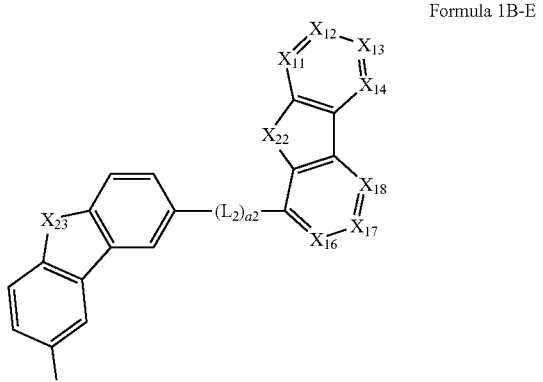
Formula 1B-F
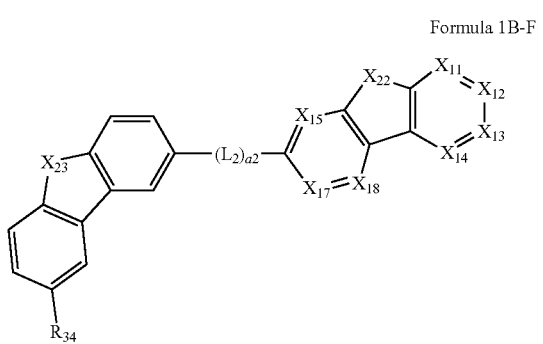
Formula 1B-G
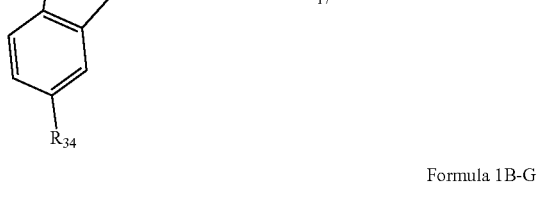
Formula 1B-H
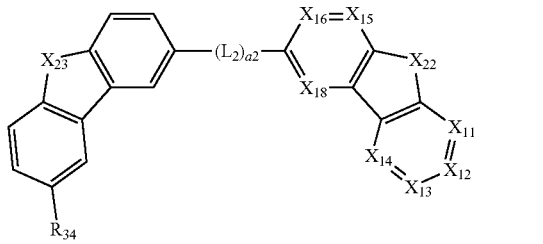
Formula 1B-I
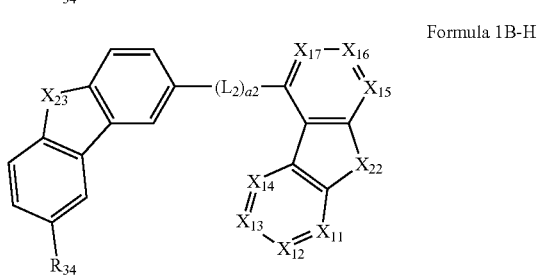
Formula 1B-J
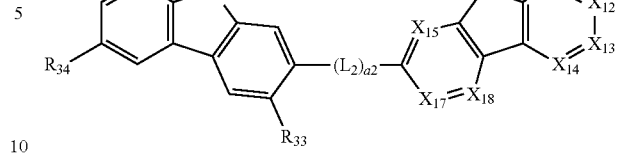
Formula 1B-K
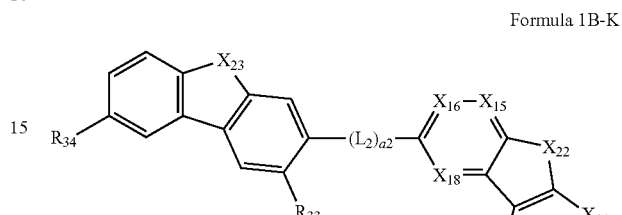
Formula 1B-L
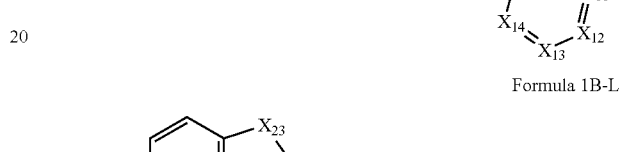
Formula 1B-M
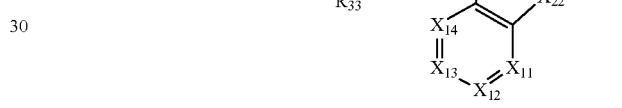
Formula 1B-N
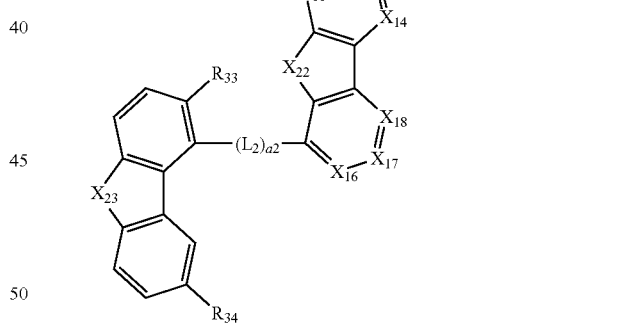

-continued

Formula 1B-O

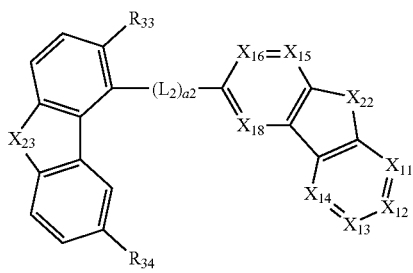

Formula 1B-P

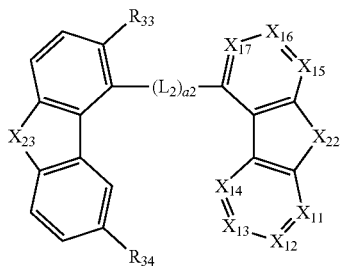

In Formulae 1B-A to 1B-P, $X_{11}$ to $X_{18}$, $X_{22}$, $X_{23}$, $L_2$, a2, $R_{33}$, and $R_{34}$ may be understood by referring to the description provided herein.

For example, in Formulae 1B-A to 1B-P, i) at least one of $X_{13}$ and $X_{17}$ may be C(CN), ii) at least one of $R_{33}$ and $R_{34}$ may be a cyano group, or iii) at least one of $X_{13}$ and $X_{17}$ may be C(CN) and at least one of $R_{33}$ and $R_{34}$ may be a cyano group.

For example, the condensed cyclic compound may be represented by one of Formulae 1A-1 to 1A-4 below:

Formula 1A-1

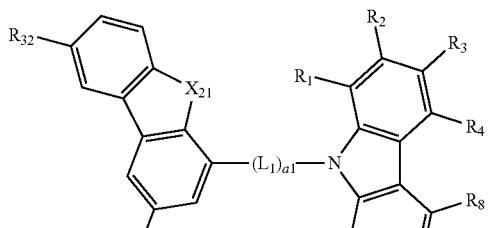

Formula 1A-2

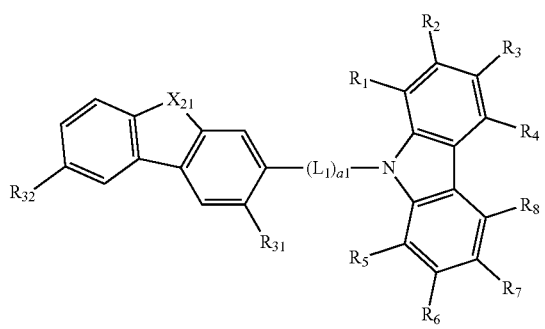

Formula 1A-3

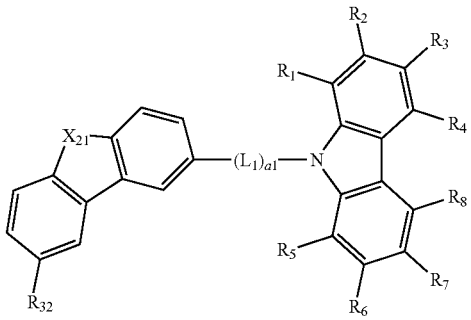

Formula 1A-4

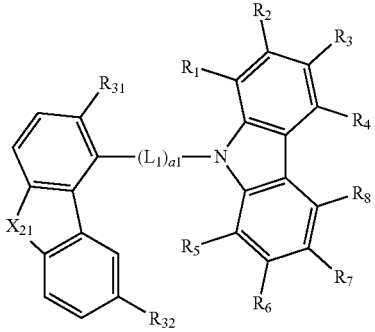

In Formulae 1A-1 to 1A-4, $X_{21}$, $L_1$, a1, $R_1$ to $R_8$, $R_{31}$, and $R_{32}$ may be understood by referring to the description provided herein.

For example, in Formulae 1A-1 to 1A-4, $X_{21}$ may be selected from O, S, C($R_{21}$)($R_{22}$), and N($R_{23}$), $R_{21}$ and $R_{22}$ may be each independently selected from a $C_1$-$C_{10}$ alkyl group and a $C_1$-$C_{10}$ alkoxy group;

a $C_1$-$C_{20}$ alkyl group and a $C_1$-$C_{20}$ alkoxy group, each substituted with at least one of a deuterium, —F, and a cyano group;

a phenyl group, a pyridinyl group, a fluorenyl group, a dibenzofuranyl group, and a dibenzothiophenyl group; and a phenyl group, a pyridinyl group, a fluorenyl group, a dibenzofuranyl group, and a dibenzothiophenyl group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group, $R_{23}$ may be selected from a phenyl group, a pyridinyl group, a fluorenyl group, a dibenzofuranyl group, and a dibenzothiophenyl group; and a phenyl group, a pyridinyl group, a fluorenyl group, a dibenzofuranyl group, and a dibenzothiophenyl group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group, $L_1$ may be represented by Formula 2-3,

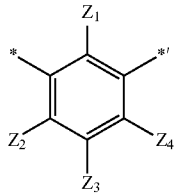

Formula 2-3 a1 may be 0 or 1, $R_1$, $R_2$, $R_4$, $R_5$, $R_6$, and $R_8$ may be each independently selected from a hydrogen, a deuterium, —F, a hydroxyl group, a $C_1$-$C_{10}$ alkyl group, a $C_1$-$C_{10}$ alkoxy group, a phenyl group, a pyridinyl group, a fluorenyl group, a dibenzofuranyl group, a dibenzothiophenyl group, and —Si($Q_{21}$)($Q_{22}$)($Q_{23}$), $R_3$, $R_7$, $R_{31}$, and $R_{32}$ may be each independently selected from a hydrogen, a deuterium, —F, a hydroxyl group, a cyano group, a $C_1$-$C_{10}$ alkyl group, a $C_1$-$C_{10}$ alkoxy group, a phenyl group, a pyridinyl group, a fluorenyl group, a dibenzofuranyl group, a dibenzothiophenyl group, and —Si($Q_{21}$)($Q_{22}$)($Q_{23}$), and $Q_{21}$ to $Q_{23}$ may be each independently selected from a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group.

In Formulae 1A-1, 1A-2, and 1A-4, at least one of $R_3$, $R_7$, $R_{31}$, and $R_{32}$ may be a cyano group, and in Formula 1A-3, at least one of $R_3$, $R_7$, and $R_{32}$ may be a cyano group.

For example, in Formulae 1A-1 to 1A-4, at least one of $R_3$ and $R_7$ may be a cyano group, but embodiments are not limited thereto.

For example, the condensed cyclic compound may be represented by one of Formulae 1B-1 to 1B-4 below:

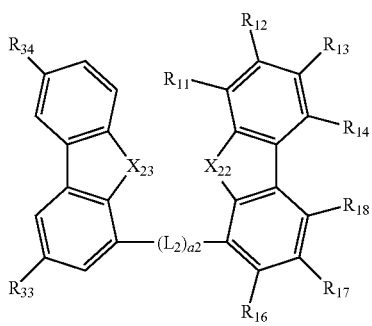

Formula 1B-1

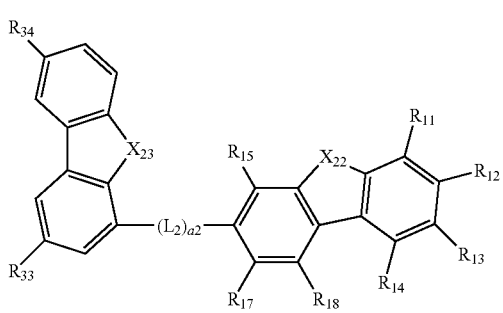

Formula 1B-2

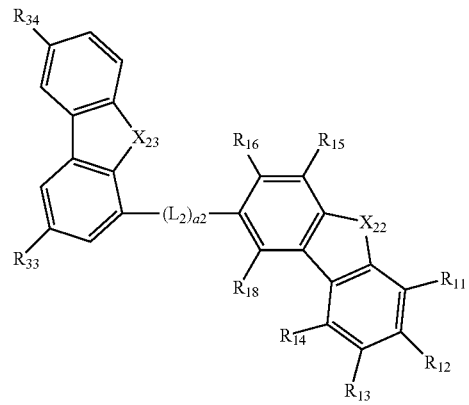

Formula 1B-3

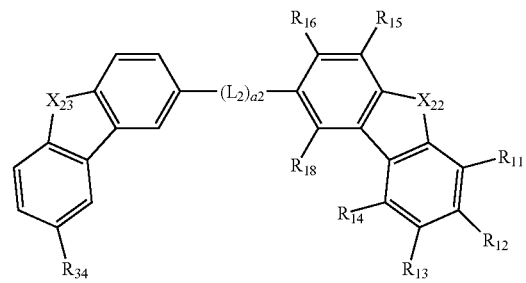

Formula 1B-4

In Formulae 1B-1 to 1B-4, $X_{22}$, $X_{23}$, $L_2$, a2, $R_{11}$ to $R_{18}$, $R_{33}$, and $R_{34}$ may be understood by referring to the description provided herein.

For example, in Formulae 1B-1 to 1B-4, $X_{22}$ may be selected from O, S, C($R_{24}$)($R_{25}$), and N($R_{26}$), $X_{23}$ may be selected from O, S, C($R_{27}$)($R_{28}$), and N($R_{29}$), $R_{24}$, $R_{25}$, $R_{27}$, and $R_{28}$ may be each independently selected from a $C_1$-$C_{10}$ alkyl group and a $C_1$-$C_{10}$ alkoxy group;

a $C_1$-$C_{20}$ alkyl group and a $C_1$-$C_{20}$ alkoxy group, each substituted with at least one of a deuterium, —F, and a cyano group;

a phenyl group, a pyridinyl group, a fluorenyl group, a dibenzofuranyl group, and a dibenzothiophenyl group; and a phenyl group, a pyridinyl group, a fluorenyl group, a dibenzofuranyl group, and a dibenzothiophenyl group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group, $R_{26}$ and $R_{29}$ may be each independently selected from a phenyl group, a pyridinyl group, a fluorenyl group, a dibenzofuranyl group, and a dibenzothiophenyl group; and a phenyl group, a pyridinyl group, a fluorenyl group, a dibenzofuranyl group, and a dibenzothiophenyl group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group, $L_2$ may be represented by Formula 2-3 below,

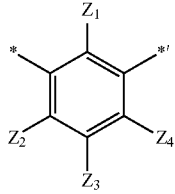

Formula 2-3 a2 may be 0 or 1, $R_{11}$, $R_{12}$, $R_{14}$, $R_{15}$, $R_{16}$, and $R_{18}$ may be each independently selected from a hydrogen, a deuterium, —F, a hydroxyl group, a $C_1$-$C_{10}$ alkyl group, a $C_1$-$C_{10}$ alkoxy group, a phenyl group, a pyridinyl group, a fluorenyl group, a dibenzofuranyl group, a dibenzothiophenyl group, and —Si($Q_{21}$)($Q_{22}$)($Q_{23}$), $R_{13}$, $R_{17}$, $R_{33}$, and $R_{34}$ may be each independently selected from a hydrogen, a deuterium, —F, a hydroxyl group, a cyano group, a $C_1$-$C_{10}$ alkyl group, a $C_1$-$C_{10}$ alkoxy group, a phenyl group, a pyridinyl group, a fluorenyl group, a dibenzofuranyl group, a dibenzothiophenyl group, and —Si($Q_{21}$)($Q_{22}$)($Q_{23}$), $Q_{21}$ to $Q_{23}$ may be each independently selected from a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group, and at least one of $R_{13}$, $R_{17}$, $R_{33}$, and $R_{34}$ in Formulae 1B-1 and 1B-2 may be a cyano group, at least one of $R_{13}$, $R_{33}$, and $R_{34}$ in Formula 1B-3 may be a cyano group, and at least one of $R_{13}$ and $R_{34}$ in Formula 1B-4 may be a cyano group.

In an embodiment, the condensed cyclic compound of Formulae 1A or 1B may be one of Compounds 1 to 72 below, but is not limited thereto:

1

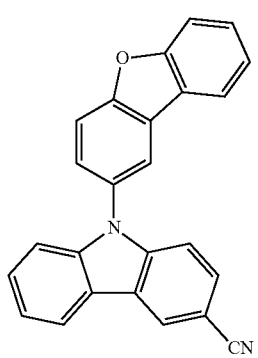

2

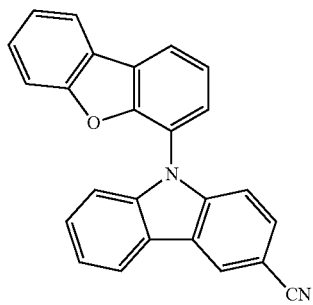

3

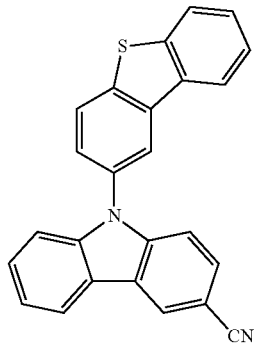

4

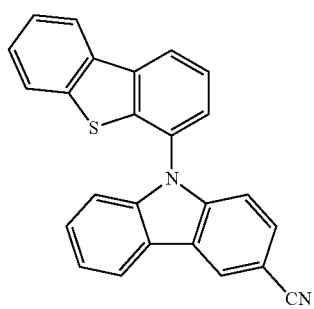

5

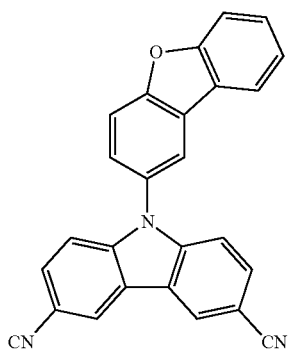

6

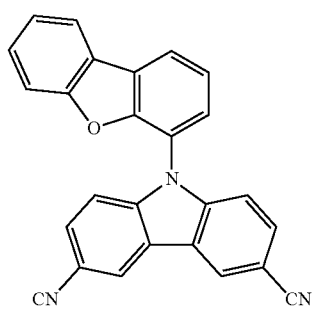

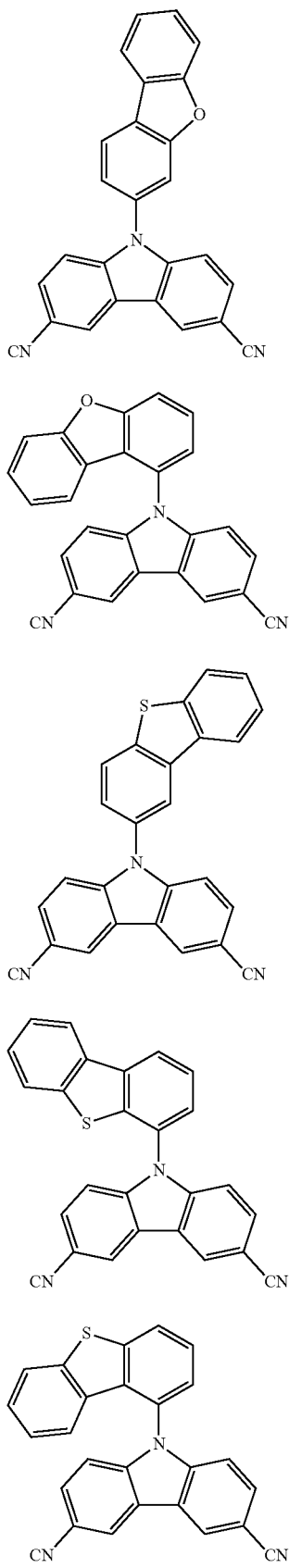
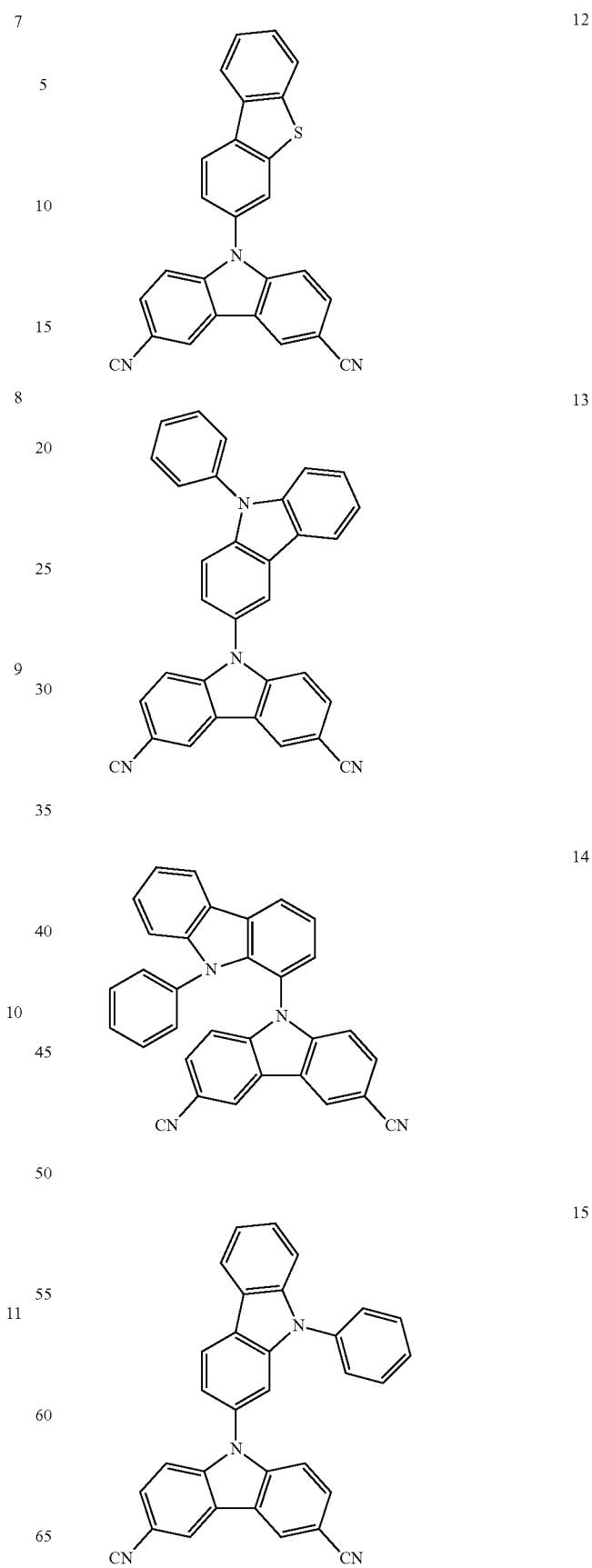

16
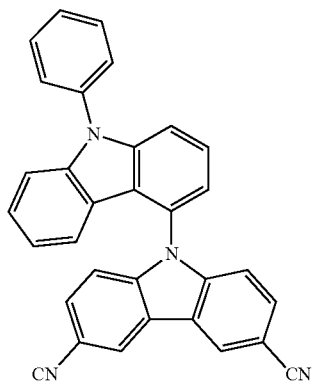
17
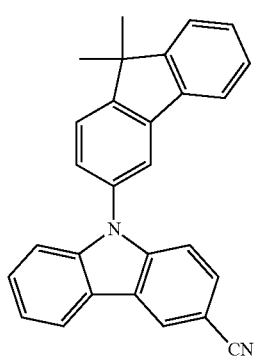
18
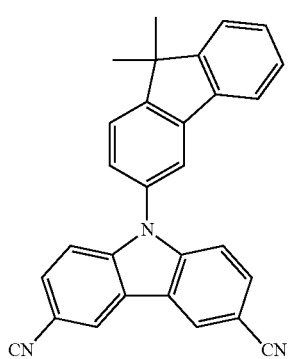
19
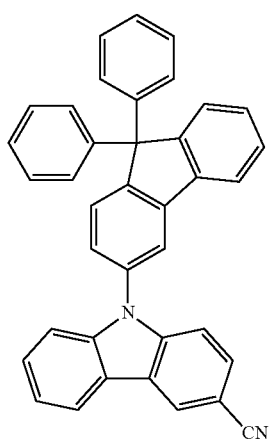
20
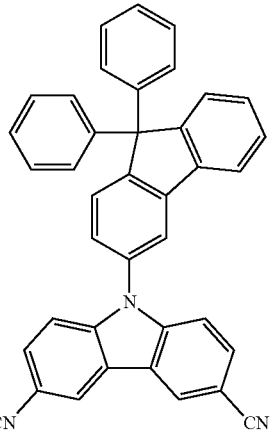
21
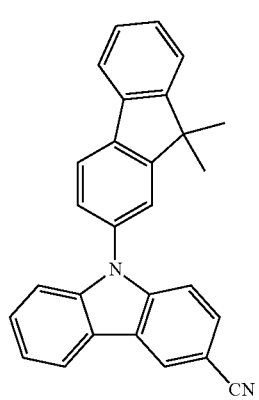
22
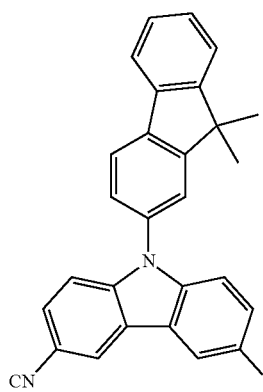
23
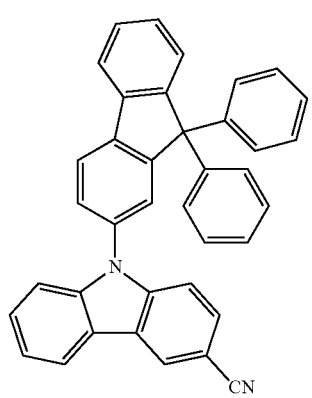

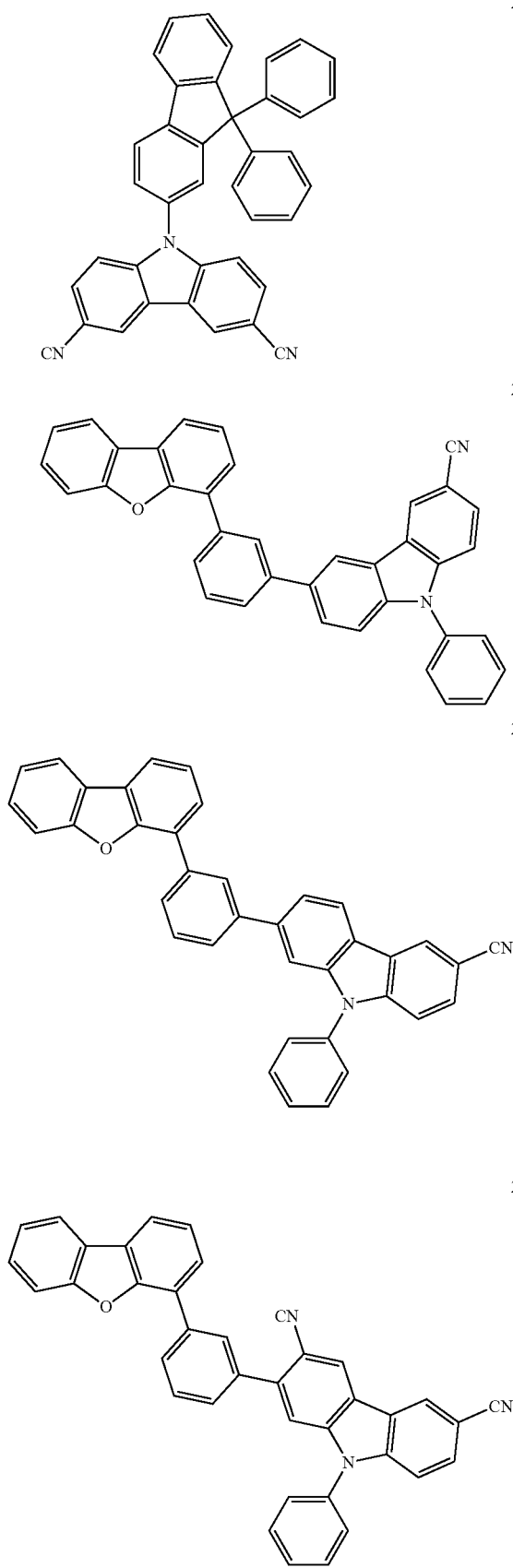

-continued
33
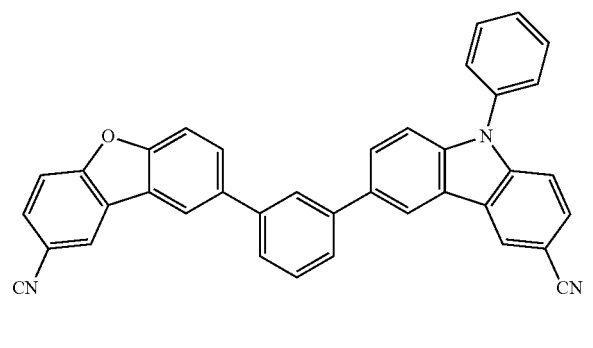
34
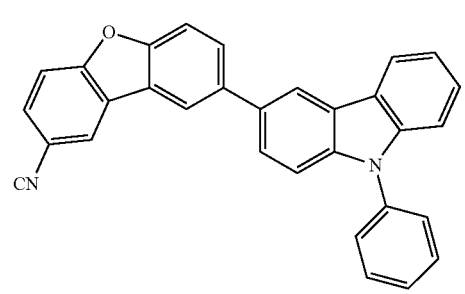
35
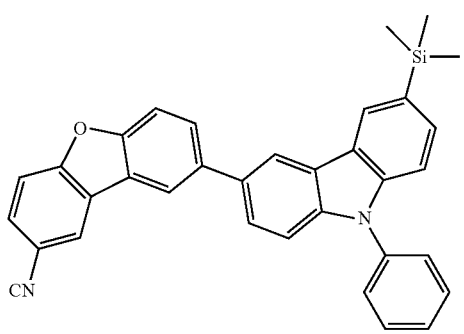
36
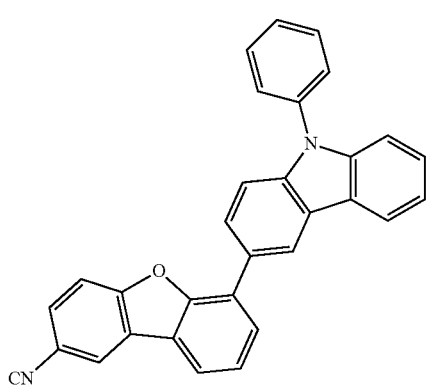
37
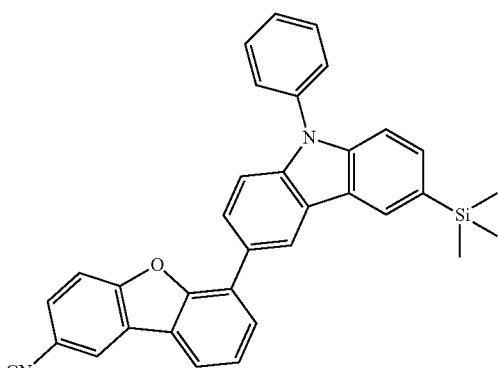
38
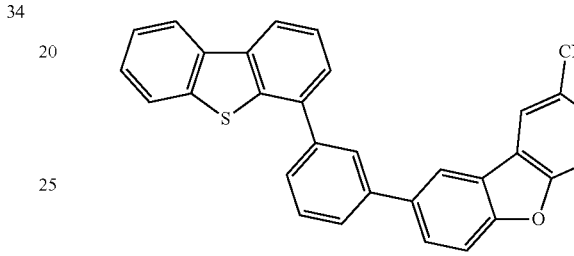
39
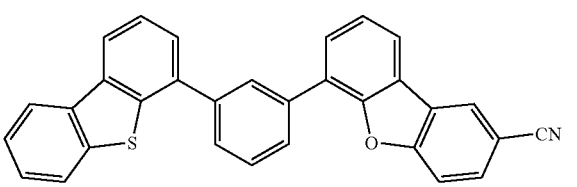
40
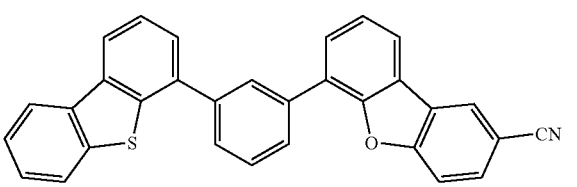
41
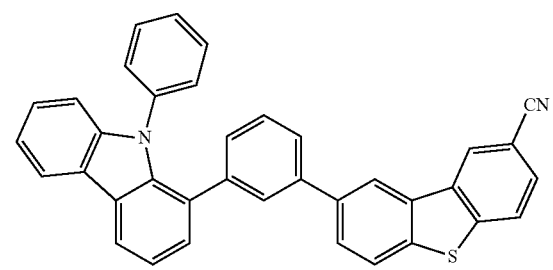

42
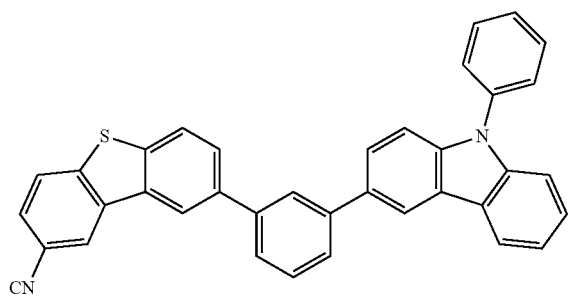
43
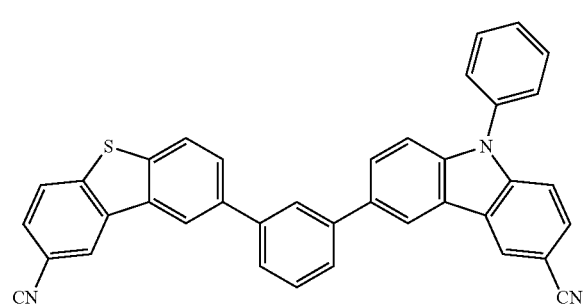
44
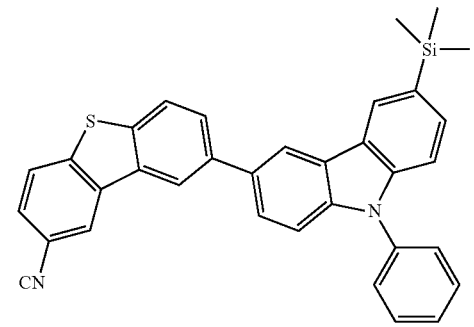
45
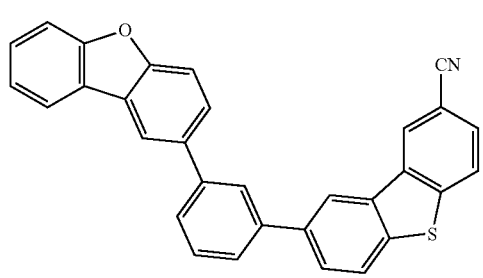
46
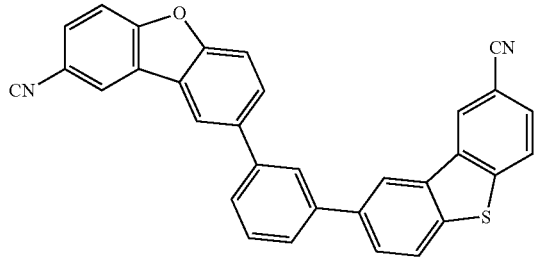
47
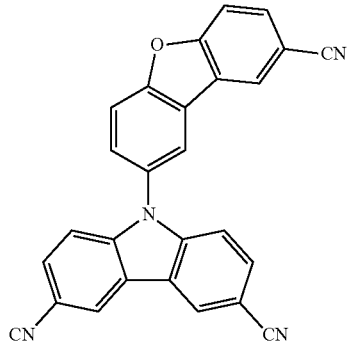
48
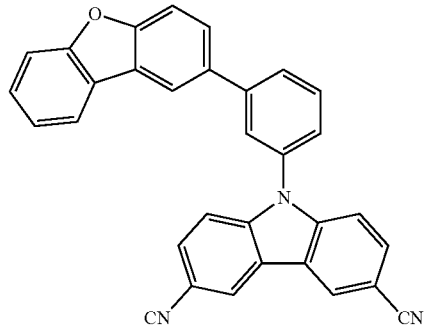
49
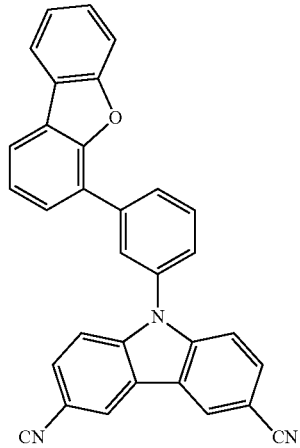
50

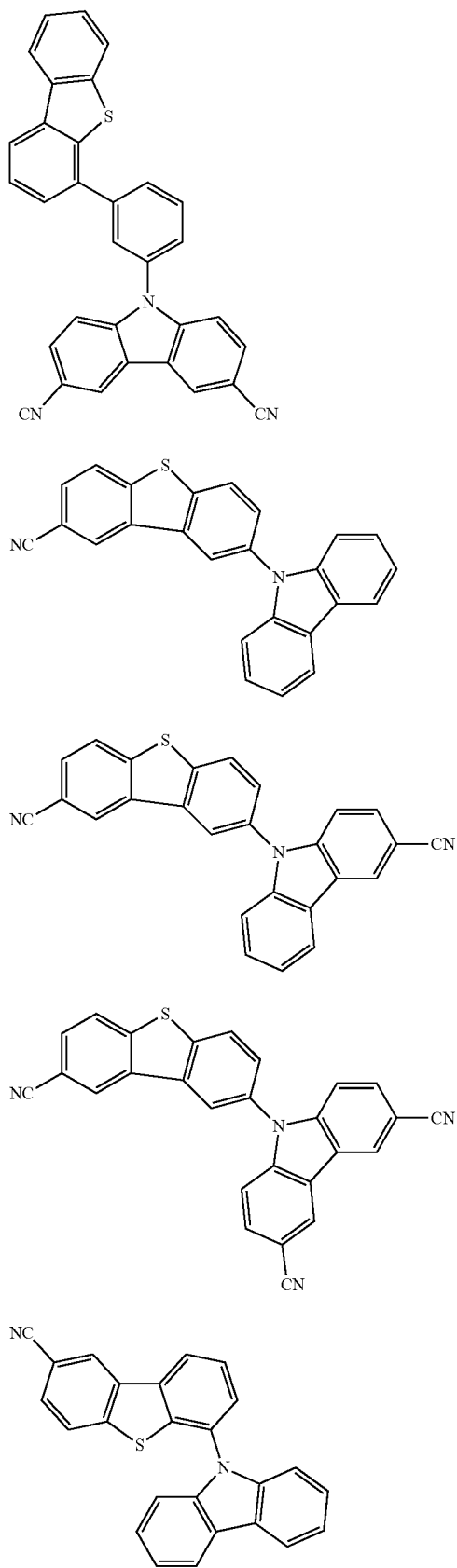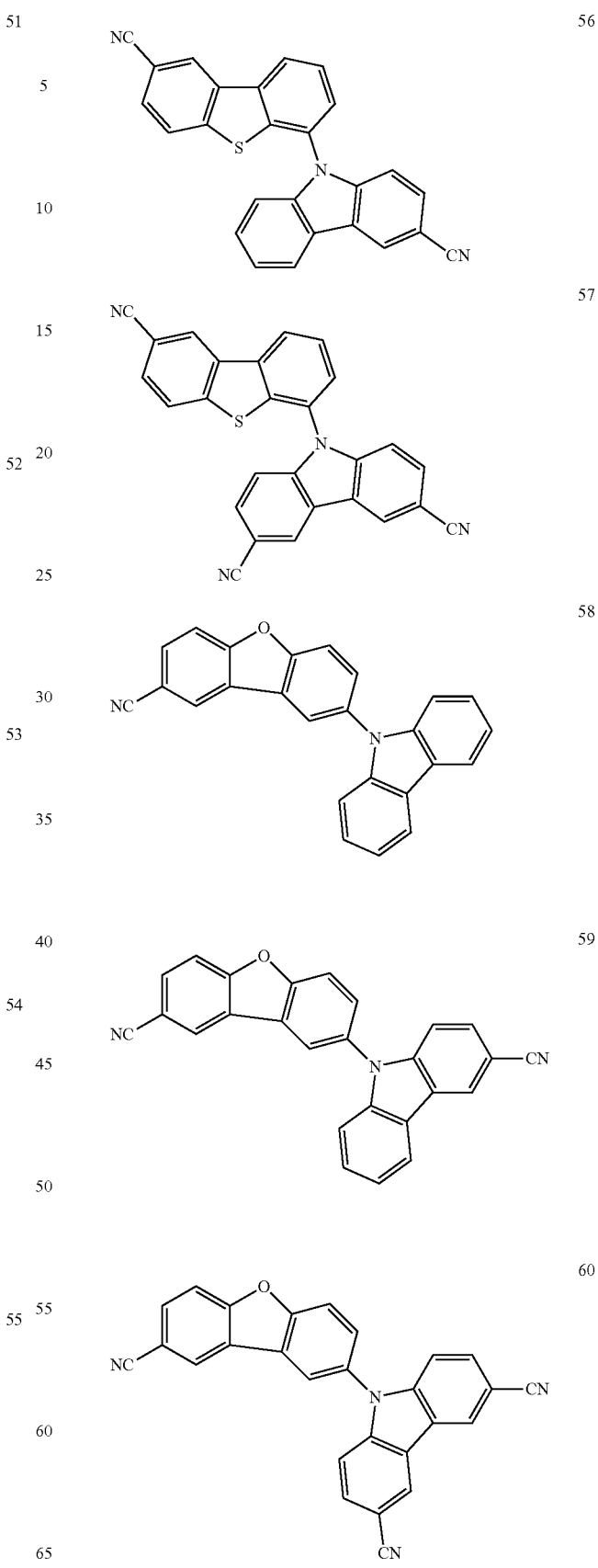

-continued
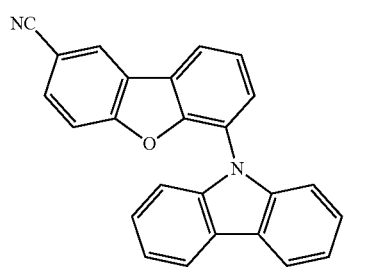
61
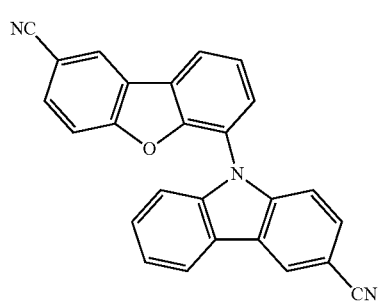
62
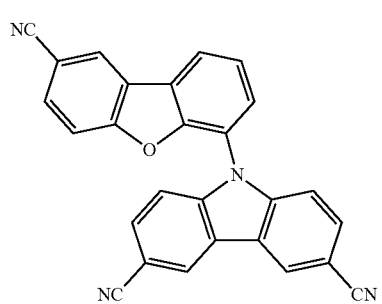
63
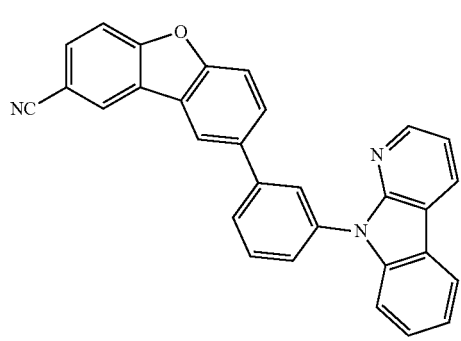
64
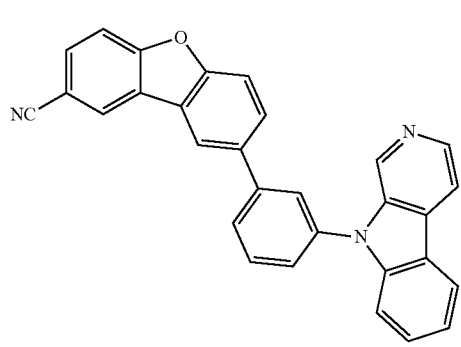
65
-continued
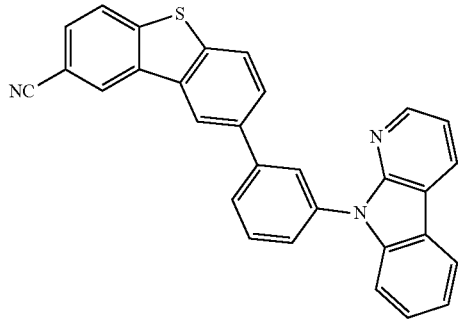
66
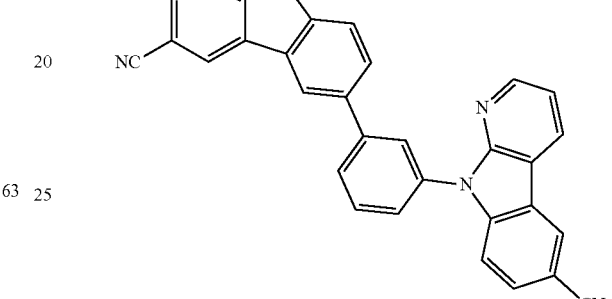
67
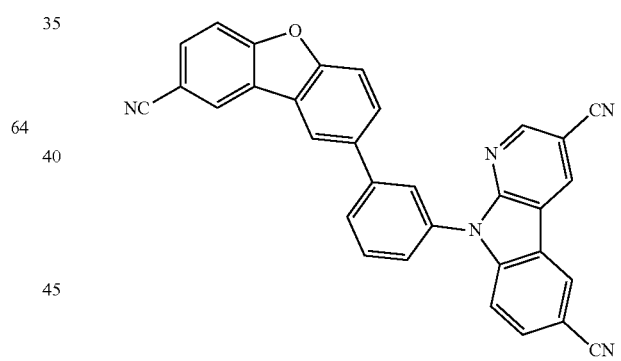
68
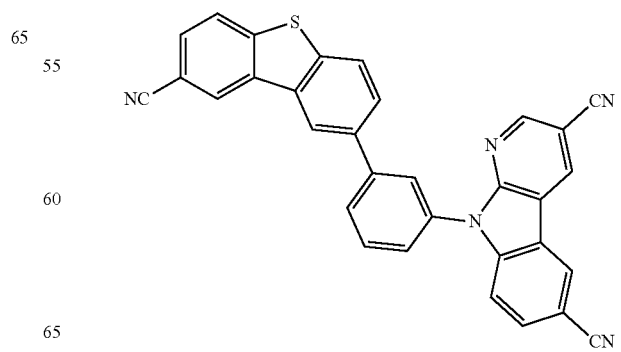
69

-continued

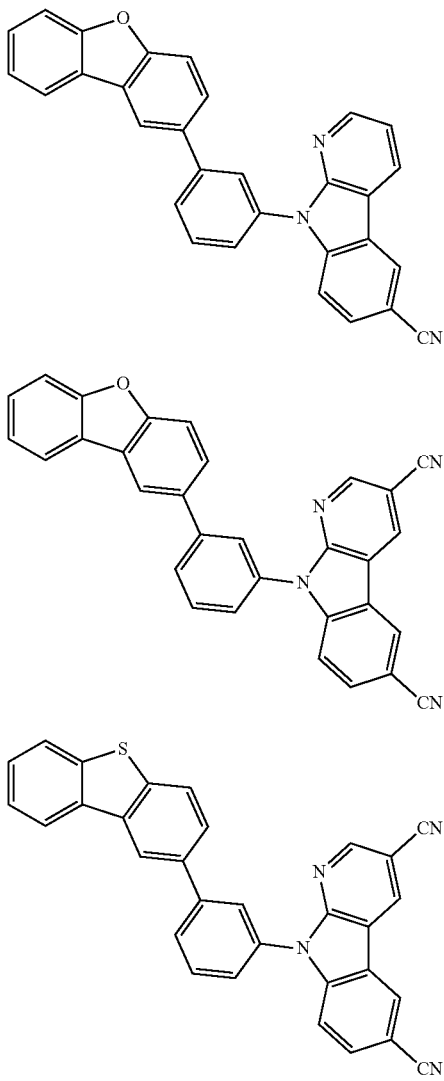

In Formulae 1A and 1B, $L_1$ and $L_2$ may be each independently a single bond (in the case where a1 and a2 are 0), or may be each independently selected from a phenylene group, a pyridinylene group, a fluorenylene group, a dibenzofuranylene group, a dibenzothiophenylene group, and derivatives thereof. In this regard, the condensed cyclic compound of Formulae 1A or 1B may have a high triplet energy level.

In Formula 1B, when $X_{22}$ is $N(R_{26})$ and $X_{23}$ is $N(R_{29})$, a2 is not 0. That is, in Formula 1B, when $X_{22}$ is $N(R_{26})$ and $X_{23}$ is $N(R_{29})$, $*\text{-}(L_2)_{a2}\text{-}*'$ is not a single bond. In this regard, the condensed cyclic compound of Formula 1B may have a high triplet energy level.

Furthermore, the condensed cyclic compound of Formulae 1A or 1B, excludes "a substituted or unsubstituted carbazolyl group" from the list of $R_1$ to $R_8$, $R_{11}$ to $R_{18}$, and $R_{31}$ to $R_{34}$, and in addition, does not include "a substituted or unsubstituted carbazolyl group" in the list of $L_1$ and $L_2$. That is, the condensed cyclic compound of Formulae 1A or 1B is considered to have 2 carbazole rings at the most. Therefore, the condensed cyclic compound of Formulae 1A or 1B may have an appropriate triplet ($T_1$) energy level, as a material for forming an organic light-emitting device, e.g., a host included in an emission layer.

Moreover, in Formula 1A, i) at least one of $X_3$ and $X_7$ may be C(CN), ii) at least one of groups $R_{31}$ in the number of b1 and groups $R_{32}$ in the number of b2 may be a cyano group, or iii) at least one of $X_3$ and $X_7$ may be C(CN) and at least one of groups $R_{31}$ in the number of b1 and groups $R_{32}$ in the number of b2 may be a cyano group. In Formula 1B, i) at least one of $X_{13}$ and $X_{17}$ may be C(CN), ii) at least one of groups $R_{33}$ in the number of b3 and groups $R_{34}$ in the number of b4 a cyano group, or iii) at least one of $X_{13}$ and $X_{17}$ may be C(CN) and at least one of groups $R_{33}$ in the number of b3 and groups $R_{34}$ in the number of b4 may be a cyano group. In this regard, the condensed cyclic compound of Formulae 1A or 1B may have excellent thermal resistance.

The condensed cyclic compound of Formulae 1A or 1B may have a molecular weight in a range from about 350 to about 650, and in this regard, may have excellent thermal stability. For example, the condensed cyclic compound of Formulae 1A or 1B may have a higher decomposition temperature than a sublimation temperature under vacuum pressure in a range from about $10^{-8}$ torr to about $10^{-3}$ torr. In this regard, an organic light-emitting including the condensed cyclic compound may have long lifespan.

For example, regarding Compounds 1 to 16 and A to C, a highest occupied molecular orbital (HOMO) energy level, a lowest unoccupied molecular orbital (LUMO) energy level, a $T_1$ energy level, and a singlet ($S_1$) energy level are calculated using the Gaussian program, and results of the calculation are shown in Table 1 below:

TABLE 1

| | HOMO (eV) | LUMO (eV) | $T_1$ (eV) | $S_1$ (eV) |
|---|---|---|---|---|
| Compound 1 | −5.795 | −1.462 | 3.124 | 3.539 |
| Compound 2 | −5.8 | −1.453 | 3.12 | 3.527 |
| Compound 3 | −5.781 | −1.463 | 3.113 | 3.422 |
| Compound 4 | −5.859 | −1.457 | 3.118 | 3.522 |
| Compound 5 | −6.221 | −1.688 | 3.082 | 3.631 |
| Compound 6 | −6.224 | −1.695 | 3.088 | 3.602 |
| Compound 7 | −6.188 | −1.736 | 3.078 | 3.643 |
| Compound 8 | −6.303 | −1.708 | 3.088 | 3.655 |
| Compound 9 | −6.188 | −1.687 | 3.08 | 3.474 |
| Compound 10 | −6.279 | −1.692 | 3.09 | 3.537 |
| Compound 11 | −6.204 | −1.744 | 3.06 | 3.508 |
| Compound 12 | −6.343 | −1.704 | 3.149 | 3.697 |
| Compound 13 | −5.904 | −1.494 | 3.081 | 3.29 |
| Compound 14 | −6.013 | −1.577 | 3.089 | 3.345 |
| Compound 15 | −5.977 | −1.538 | 3.078 | 3.287 |
| Compound 16 | −5.946 | −1.509 | 3.09 | 3.319 |
| Compound A | −5.588 | −1.989 | 2.8 | 3.032 |
| Compound B | −5.266 | −1.473 | 2.542 | 3.245 |
| Compound C | −5.537 | −1.288 | 2.99 | 3.245 |

Compound A

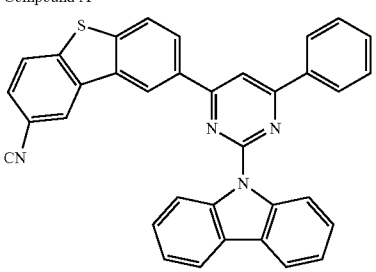

TABLE 1-continued

| | HOMO (eV) | LUMO (eV) | $T_1$ (eV) | $S_1$ (eV) |
|---|---|---|---|---|
| CompoundB | | | | |
| Compound C | | | | |

Referring to Table 1 above, it is confirmed that Compounds 1 to 16 have higher $T_1$ energy levels than those of Compounds A to C.

A method of synthesizing the condensed cyclic compound of Formulae 1A or 1B may be understood by one of ordinary skill in the art based on Synthesis Examples described below.

Therefore, the condensed cyclic compound of Formulae 1A or 1B may be suitable for forming an organic layer included in an organic light-emitting device, and for example, may be used as a host in an emission layer included in the organic layer. According to another aspect, an organic light-emitting device may include a first electrode;
a second electrode; and
an organic layer disposed between the first electrode and the second electrode, wherein the organic layer includes an emission layer and at least one condensed cyclic compound of Formulae 1A or 1B.

The organic light-emitting device may include an organic layer including the condensed cyclic compound of Formulae 1A or 1B, and accordingly, may have low driving voltage, high efficiency, high luminance, high quantum efficiency, and long lifespan.

The condensed cyclic compound of Formulae 1A or 1B may be used between a pair of electrodes of the organic light-emitting device. For example, the condensed cyclic compound of Formulae 1A or 1B may be included in at least one of an emission layer, a hole transport region (including, for example, at least one of a hole injection layer, a hole transport layer, and an electron blocking layer), which is disposed between the first electrode and the emission layer, and an electron transport region (including, for example, at least one of a hole blocking layer, an electron transport layer, and an electron injection layer), which is disposed between the emission layer and the second electrode. For example, the condensed cyclic compound of Formulae 1A or 1B may be included in the emission layer. Here, the emission layer may further include a dopant, and the condensed cyclic compound of Formulae 1A or 1B included in the emission layer may act as a host. The emission layer may be a green emission layer emitting green light or a blue emission layer emitting blue light. The dopant may be a phosphorescent dopant.

The expression "(an organic layer) includes at least one of the condensed cyclic compound" as used herein may be applicable when "(an organic layer) includes one condensed cyclic compound of Formulae 1A or 1B or two or more different condensed cyclic compounds of Formulae 1A or 1B".

For example, the organic layer may include, as the condensed cyclic compound, only Compound 1. In this regard, Compound 1 may be situated in the emission layer of the organic light-emitting device. Alternatively, the organic layer may include, as the condensed cyclic compound, Compounds 1 and 2. In this regard, Compounds 1 and 2 may be situated either an identical layer (for example, Compound 1 and Compound 2 all may be situated in an emission layer), or different layers.

The first electrode may be an anode, which is a hole injection electrode, and the second electrode may be a cathode, which is an electron injection electrode. Alternatively, the first electrode may be a cathode, which is an electron injection electrode, and the second electrode may be anode, which is a hole injection electrode.

For example, the first electrode may be an anode, the second electrode may be a cathode, and the organic layer may include i) a hole transport region that is disposed between the first electrode and the emission layer, wherein the hole transport layer includes at least one of a hole injection layer (HIL), a hole transport layer (HTL), and an electron blocking layer (EBL); and ii) an electron transport region that is disposed between the emission layer and the second electrode, wherein the electron transport layer includes at least one of a hole blocking layer (HBL), an electron transport layer (ETL), and an electron injection layer (EIL).

The term "organic layer" as used herein refers to a single layer and/or a plurality of layers disposed between the first electrode and the second electrode of the organic light-emitting device. A material included in the "organic layer" may include not only an organic compound, but also a metal-containing organometallic complex.

FIG. 1 is a schematic cross-sectional view of an organic light-emitting device 10 according to an embodiment. Hereinafter, the structure of an organic light-emitting device according to an embodiment and a method of manufacturing an organic light-emitting device according to an embodiment will be described in connection with FIG. 1. The organic light-emitting device 10 includes a first electrode 11, an organic layer 15, and a second electrode 19 that are sequentially stacked in the stated order.

A substrate may be additionally disposed under the first electrode 11 or on top of the second electrode 19. For use as the substrate, any substrate that is used in a typical organic light-emitting device may be used. The substrate may be a glass substrate or a transparent plastic substrate, each of which has excellent mechanical strength, thermal stability, transparency, surface smoothness, ease of handling, and water-proofness.

The first electrode 11 may be formed by, for example, depositing or sputtering a material for forming the first electrode 11 on top of the substrate. When the first electrode 11 is an anode, a material for forming the first electrode 11 may be selected from materials having a high work function to facilitate hole injection. The first electrode 11 may be a reflective electrode, a semi-transmissive electrode, or a transmissive electrode. The material for forming the first electrode 11 may be an indium tin oxide (ITO), indium zinc oxide (IZO), tin oxide ($SnO_2$), or zinc oxide (ZnO). Alternatively, the material for forming the first electrode 11 may be metal, such as magnesium (Mg), aluminum (Al), aluminum-lithium (Al—Li), calcium (Ca), magnesium-indium (Mg—In), and magnesium-silver (Mg—Ag).

The first electrode 11 may have a single-layer structure or a multi-layer structure including a plurality of layers. For example, the first electrode 11 may have a triple-layered structure of ITO/Ag/ITO, but the structure of the first electrode 11 is not limited thereto.

An organic layer 15 may be disposed on top of the first electrode 11.

The organic layer 15 may include a hole transport region; an emission layer; and an electron transport region.

The hole transport region may be disposed between the first electrode 11 and the emission layer.

The hole transport region may include at least one of a HIL, a HTL, and EBL, and a buffer layer.

The hole transport region may only include a HIL, or only include a HTL. Alternatively, the hole transport region may have a structure of HIL/HTL or a structure of HIL/HTL/EBL, each of which layers are sequentially stacked in the stated order from the first electrode 11.

When the hole transport region includes a HIL, the HIL may be formed on top of the first electrode 11 by using various methods, such as vacuum deposition, spin coating, casting, and a Langmuir-Blodgett (LB) method.

When the HIL is formed by vacuum deposition, deposition conditions may vary according to a compound used to form the HIL, a structure of the HIL, and thermal characteristics of the HIL. For example, the deposition conditions may include a deposition temperature of about 100° C. to about 500° C., a vacuum pressure of about $10^{-8}$ torr to about $10^{-3}$ torr, and a deposition rate of about 0.01 Angstroms per second (Å/sec) to about 100 Å/sec, but are not limited thereto.

When the HIL is formed by spin coating, spin coating conditions may vary according to a compound used to form the HIL, a structure of the HIL, and thermal characteristics of the HIL. For example, the spin coating conditions include a coating speed of about 2,000 revolutions per minute (rpm) to about 5,000 rpm, and a temperature at which a heat treatment is performed may be from about 80° C. to about 200° C., but are not limited thereto.

Conditions for forming a HTL and an EBL may be understood by referring to conditions for forming the HIL.

The hole transport region may include, for example, m-MTDATA, TDATA, 2-TNATA, NPB, β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (PANI/PSS), or at least one of a compound represented by Formula 201 below and a compound represented by Formula 202 below:

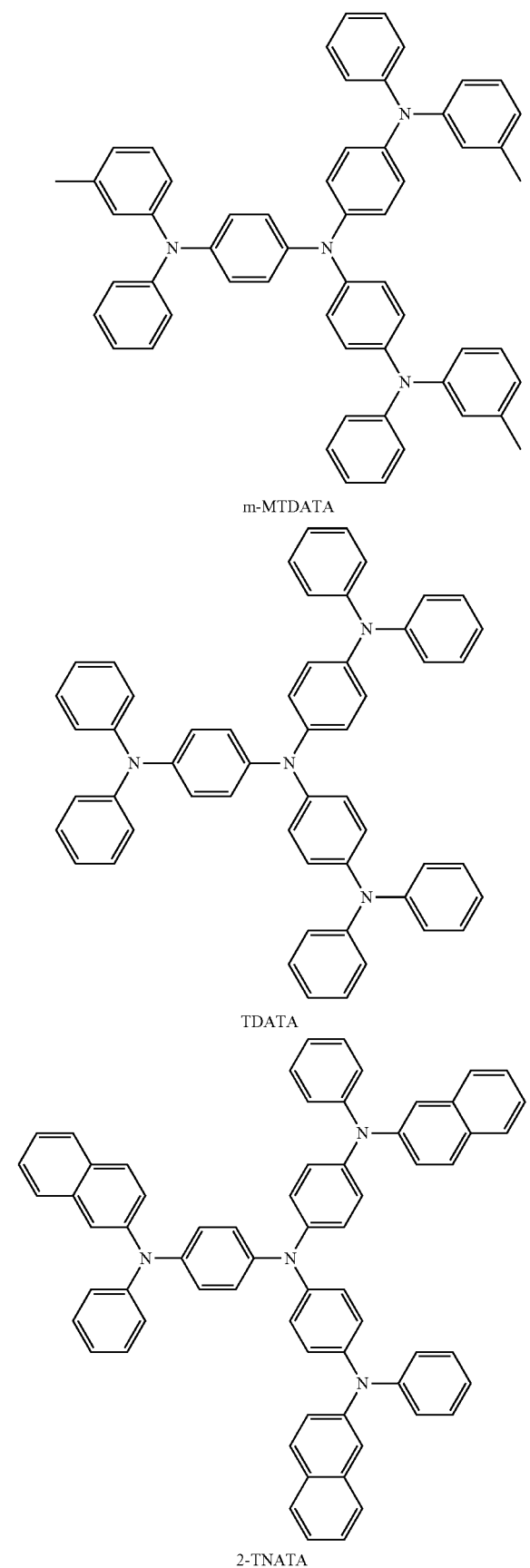

m-MTDATA

TDATA

2-TNATA

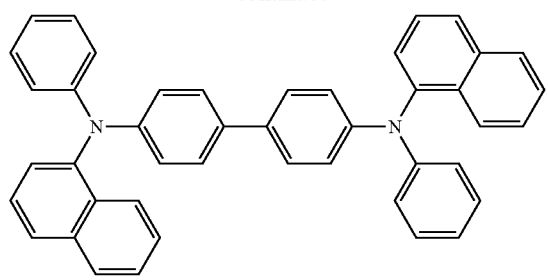
NPB
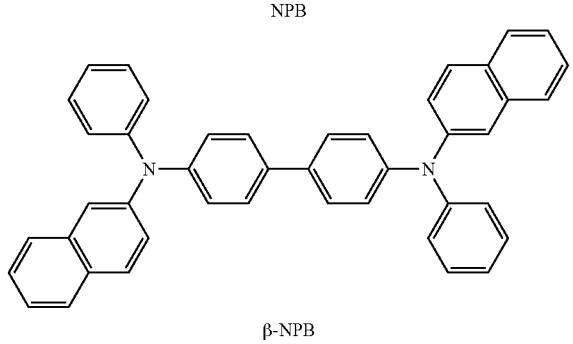
β-NPB
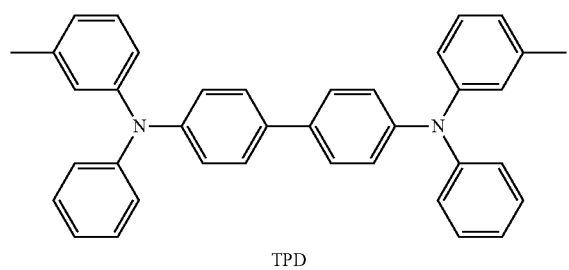
TPD
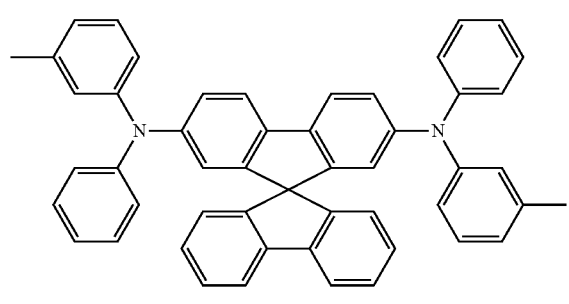
Spiro-TPD
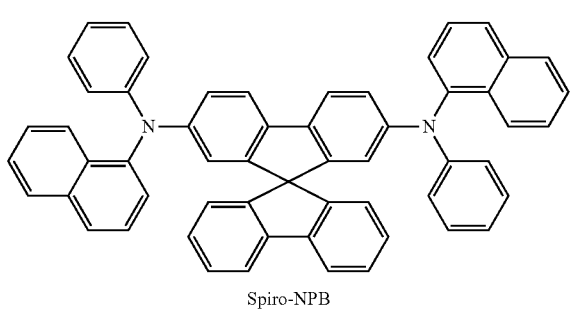
Spiro-NPB
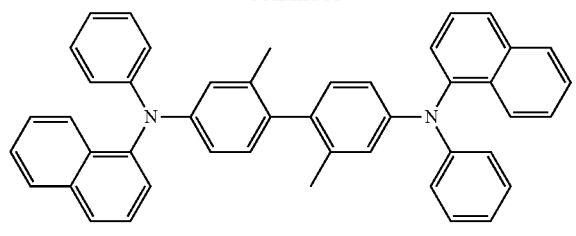
methylated NPB
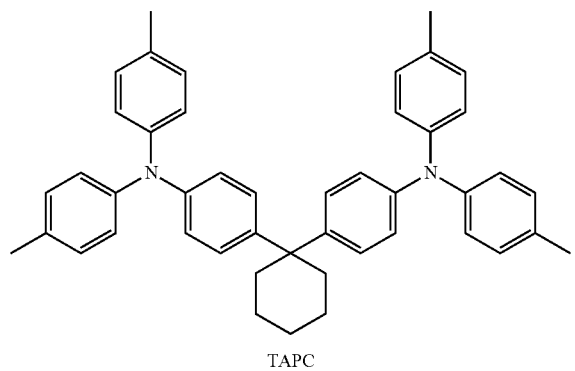
TAPC
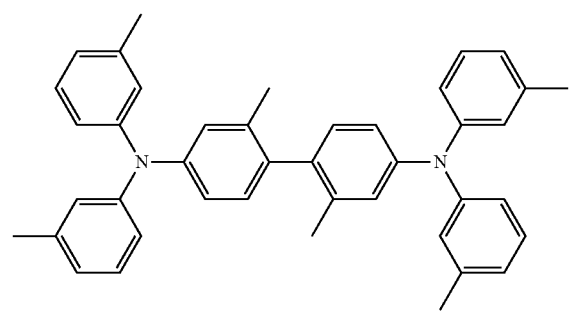
HMTPD
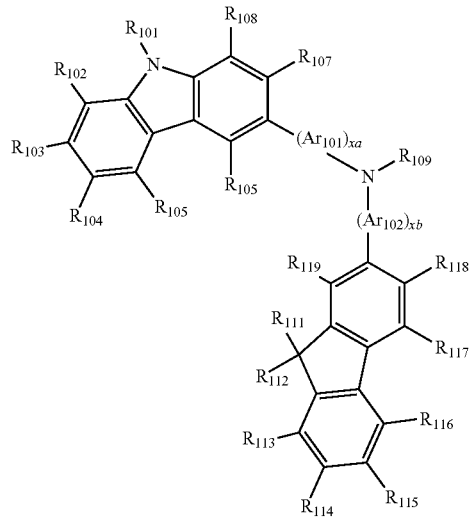
Formula 201

Formula 202

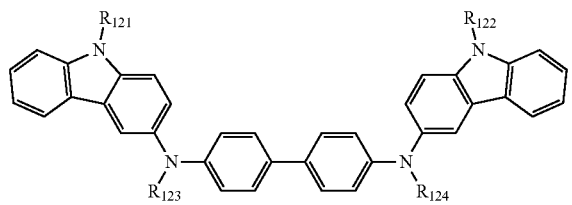

In Formula 201, $Ar_{101}$ and $Ar_{102}$ may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may be each independently an integer selected from 0 to 5, or may be 0, 1, or 2. For example, in Formula 201, xa may be 1 and xb may be 0, but are not limited thereto.

In Formulae 201 and 202, $R_{101}$ to $R_{108}$, $R_{111}$ to $R_{119}$, and $R_{121}$ to $R_{124}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, and a hexyl group) and a $C_1$-$C_{10}$ alkoxy group (for example, a methoxy group, an ethoxy group, a propoxy group, a butoxy group, and a pentoxy group);

a $C_1$-$C_{10}$ alkyl group and a $C_1$-$C_{10}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments are not limited thereto.

In Formula 201, $R_{109}$ may be selected from a phenyl group, a naphthyl group, an anthracenyl group, and a pyridinyl group; and a phenyl group, a naphthyl group, an anthracenyl group, and a pyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group.

In an embodiment, the compound of Formula 201 may be represented by Formula 201A below, but is not limited thereto:

Formula 201A

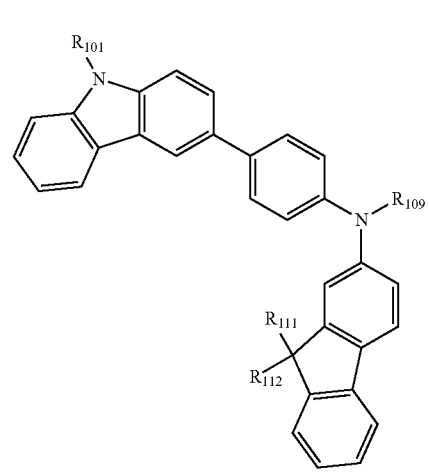

In Formula 201A, $R_{101}$, $R_{111}$, $R_{112}$, and $R_{109}$ may be understood by referring to the description provided herein.

For example, the compound of Formula 201 and the compound of Formula 202 may include Compounds HT1 to HT20 below, but are not limited thereto:

HT1
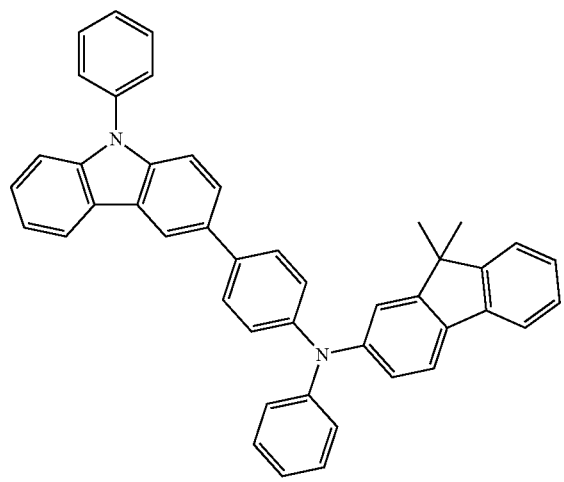
HT2
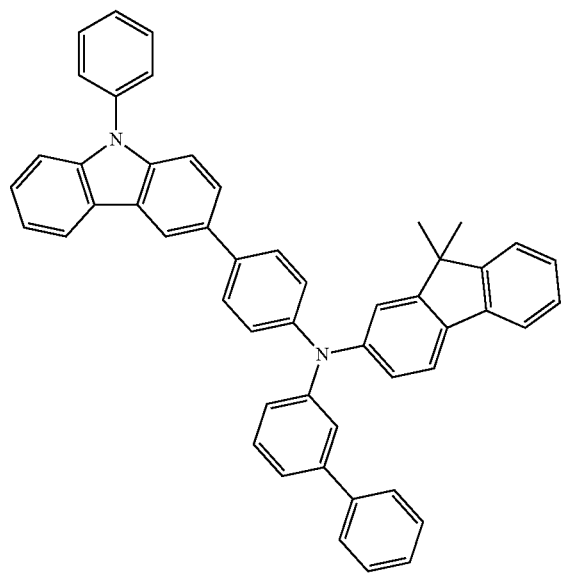
HT3
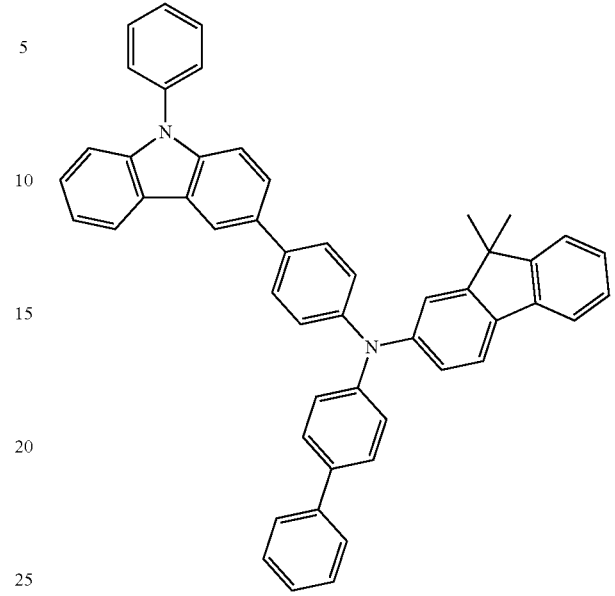
HT4
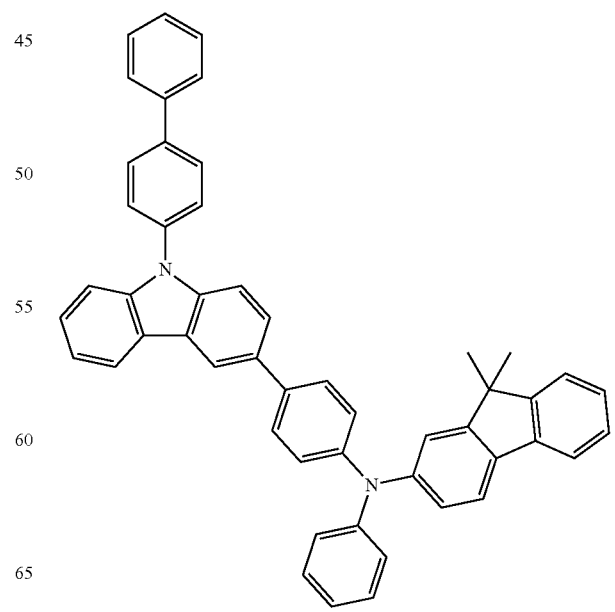

HT5
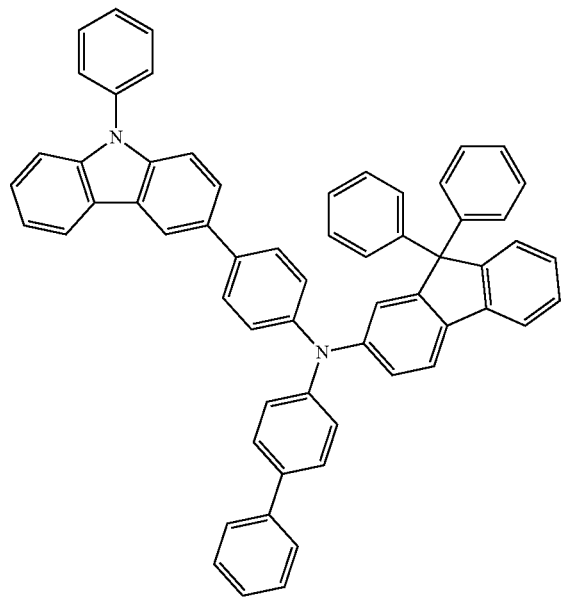
HT7
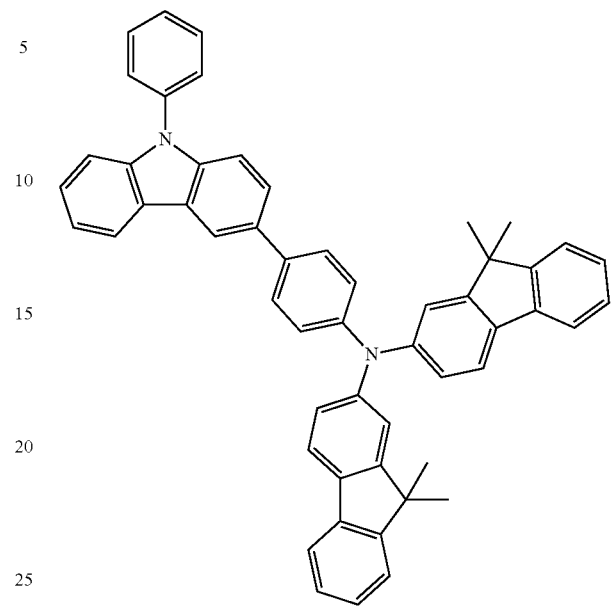
HT8
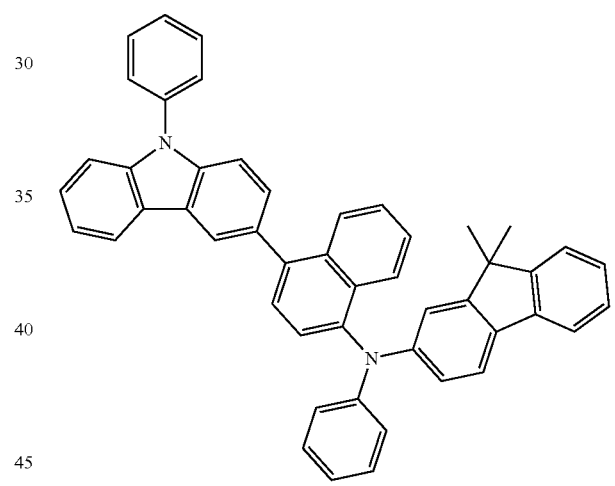
HT6
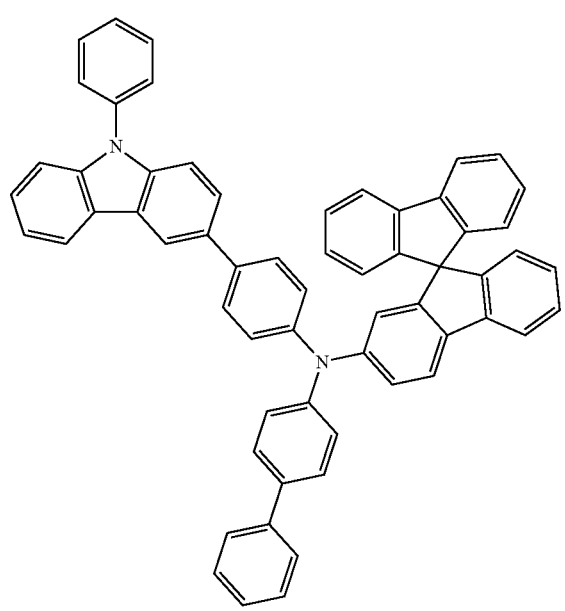
HT9
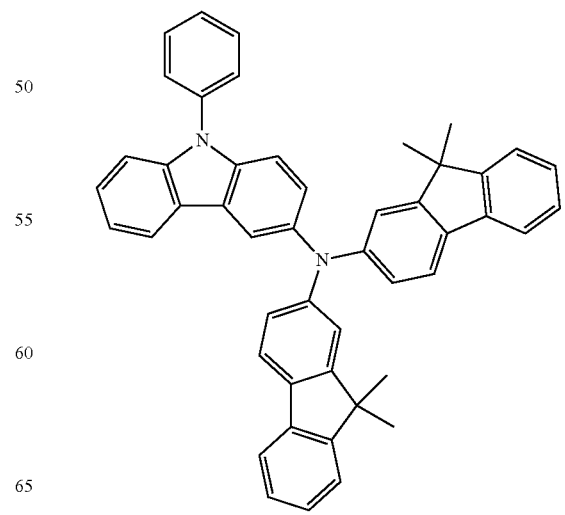

HT10
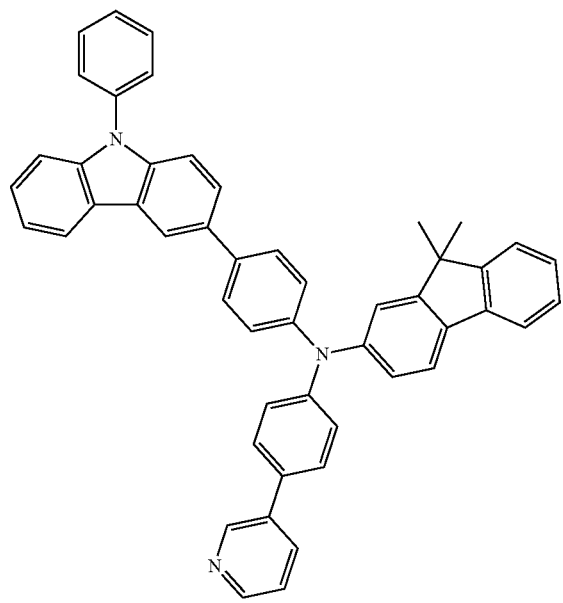
HT11
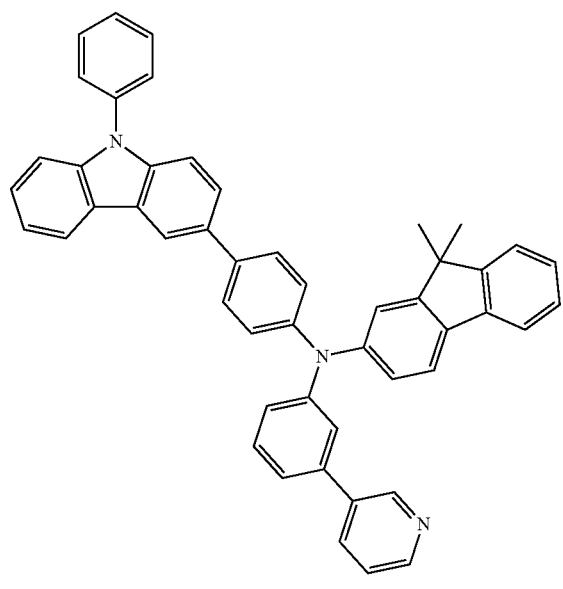
HT12
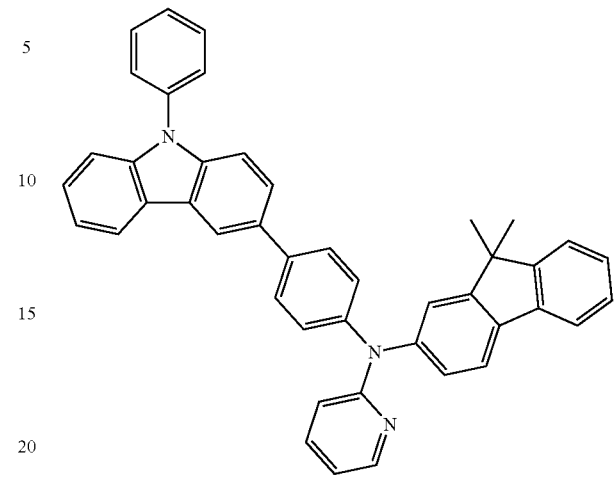
HT13
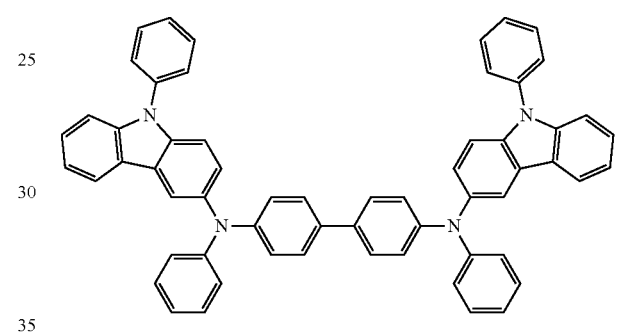
HT14
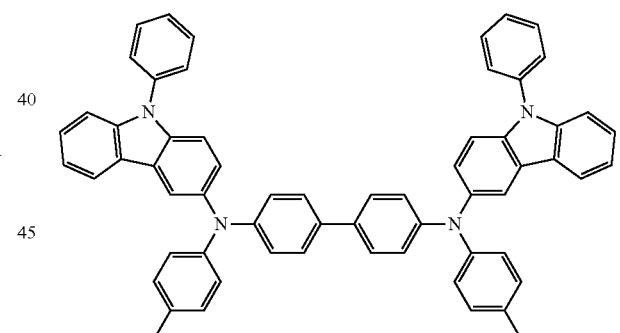
HT15
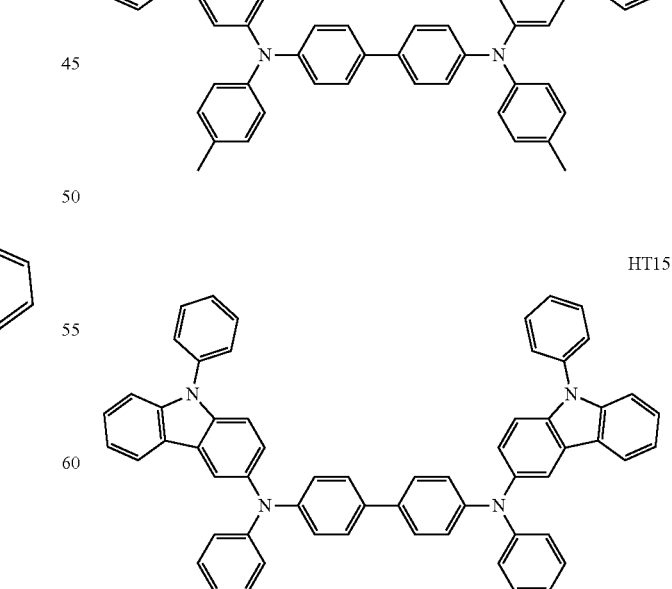

HT16

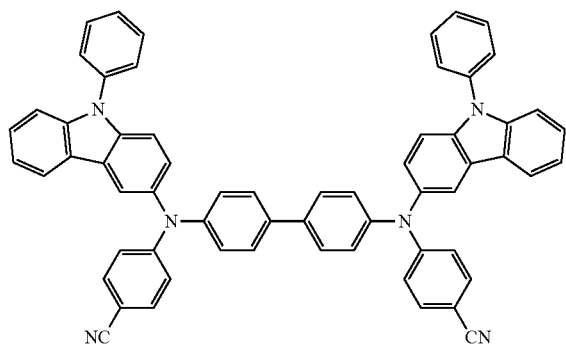

HT20

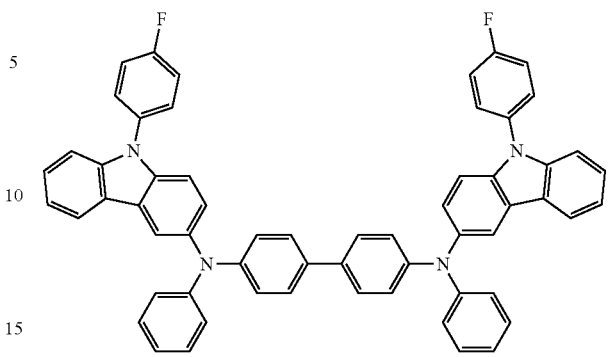

HT17

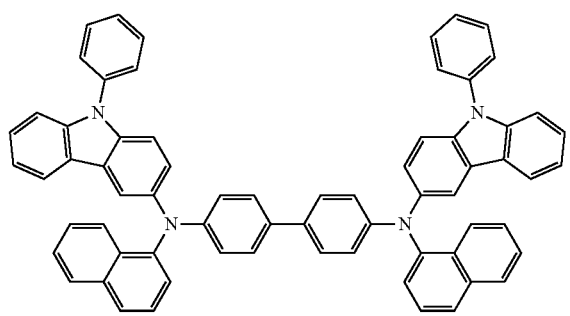

A thickness of the hole transport region may be from about 100 Å to about 10,000 Å, e.g., about 100 Å to about 1,000 Å. When the hole transport region includes both an HIL and an HTL, a thickness of the HIL may be from about 100 Å to about 10,000 Å, e.g., about 100 Å to about 1,000 Å, and a thickness of the HTL may be from about 50 Å to about 2,000 Å, e.g., about 100 Å to about 1,500 Å. When the thicknesses of the hole transport region, the HIL, and the HTL are within these ranges, satisfactory hole transporting characteristics may be obtained without a substantial increase in driving voltage.

In addition to the materials described above, the hole transport region may further include a charge-generation material for the improvement of conductive characteristics. The charge-generation material may be homogeneously or non-homogeneously dispersed in the hole transport region.

The charge-generation material may be, e.g., a p-dopant. The p-dopant may be one of a quinone derivative, a metal oxide, and a cyano group-containing compound, but is not limited thereto. Non-limiting examples of the p-dopant are a quinone derivative such as tetracyanoquinonedimethane (TCNQ) or 2,3,5,6-tetrafluoro-tetracyano-1,4-benzoquinonedimethane (F4-TCNQ); a metal oxide such as a tungsten oxide or a molybdenum oxide; and a cyano group-containing compound such as Compounds HT-D1 and HP-1 below, but are not limited thereto:

HT18

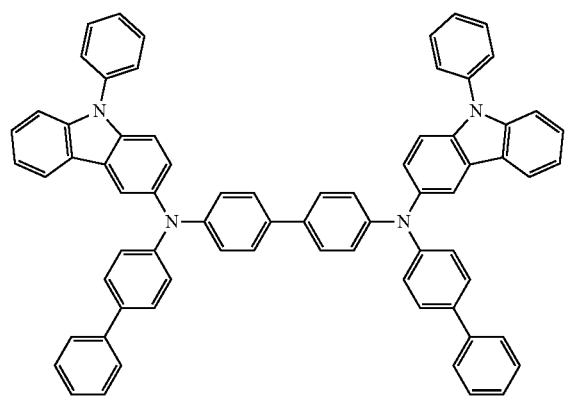

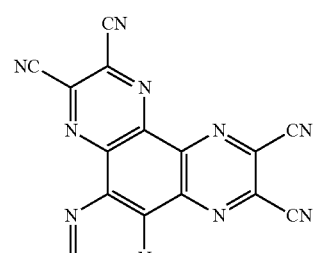

Compound HT-D1

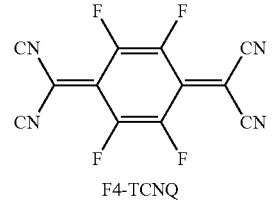

F4-TCNQ

HT19

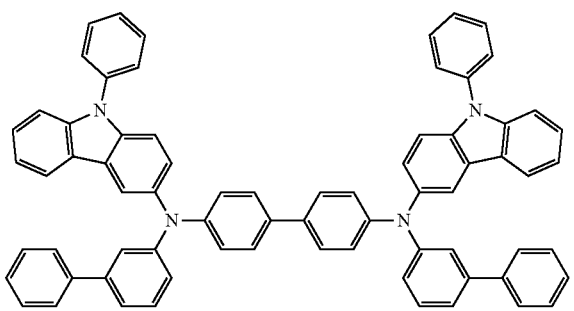

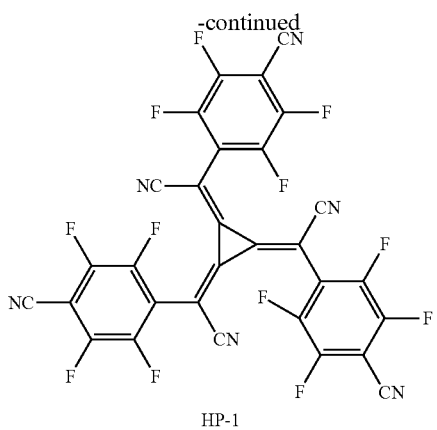

HP-1

The hole transport region may further include a buffer layer.

The buffer layer may compensate for an optical resonance distance of light according to a wavelength of the light emitted from the emission layer, and thus may improve light-emission efficiency.

The emission layer (EML) may be formed on top of the hole transport region by using various methods, such as vacuum deposition, spin coating, casting, and an LB method. When the EML is formed by vacuum deposition and spin coating, the deposition and spin coating conditions may vary according to a compound that is used to form the EML, but in general, the deposition and spin coating conditions may be determined by referring to those applied to form the HIL.

The hole transport region may further include an EBL. The EBL may include a known material, for example, mCP below, but is not limited thereto.

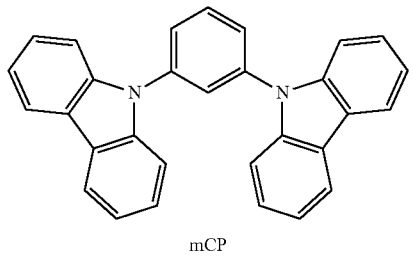 [SMILES: c1cc(-n2c3ccccc3c3ccccc32)cc(-n2c3ccccc3c3ccccc32)c1]

mCP

When the organic light-emitting device 10 is a full-color organic light-emitting device, the EML may be patterned into a red EML, a green EML, and a blue EML. Alternatively, the EML may have a structure of a red EML, a green EML, and/or a blue EML, each of which layers are sequentially stacked in this stated order, and accordingly, the EML may have a structure capable of emitting white light.

The EML may include the condensed cyclic compound of Formulae 1A or 1B. The EML may further include a dopant. The dopant may include at least one of a phosphorescent dopant and a fluorescent dopant.

For example, the host included in the EML may include the condensed cyclic compound of Formulae 1A or 1B.

The dopant included in the EML may be a fluorescent dopant that emits light according to a fluorescence emission mechanism, or may be a phosphorescent dopant that emits light according to a phosphorescence emission mechanism.

In an embodiment, the dopant included in the EML may be a phosphorescent dopant, and the phosphorescent dopant may include an organometallic compound represented by Formula 81 below:

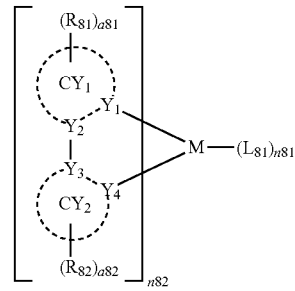

Formula 81

In Formula 81,

M may be selected from iridium (Ir), platinum (Pt), osmium (Os), titanium (Ti), zirconium (Zr), hafnium (Hf), europium (Eu), terbium (Tb), and thulium (Tm), $Y_1$ to $Y_4$ may be each independently carbon (C) or nitrogen (N), $Y_1$ and $Y_2$ may be linked with each other by a single bond or a double bond, and $Y_3$ and $Y_4$ may be linked with each other by a single bond or a double bond, $CY_1$ and $CY_2$ may be each independently selected from a benzene, a naphthalene, a fluorene, a spiro-fluorene, an indene, a pyrrole, a thiophene, a furan, an imidazole, a pyrazole, a thiazole, an isothiazole, an oxazole, an isoxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzoxazole, an isobenzoxazole, a triazole, a tetrazole, an oxadiazole, a triazine, a dibenzofuran, and a dibenzothiophene, wherein $CY_1$ and $CY_2$ may be optionally additionally linked with each other by an organic linking group, $R_{81}$ and $R_{82}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, and —$B(Q_6)(Q_7)$ (wherein, $Q_1$ to $Q_7$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group and a monovalent non-aromatic condensed heteropolycyclic group), a81 and a82 may be each independently an integer selected from 1 to 5, n81 may be an integer selected from 0 to 4, n82 may be 1, 2, or 3, and $L_{81}$ may be a monovalent organic ligand, a divalent organic ligand, or a trivalent organic ligand.

The phosphorescent dopant may include at least one of Compounds PD1 to PD78, and CIM02 below, but is not limited thereto:

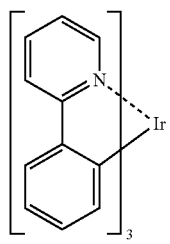

PD1

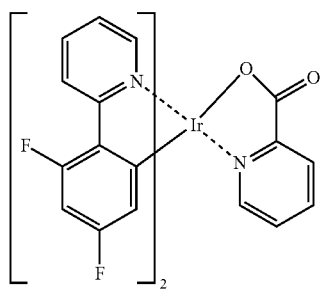

PD2

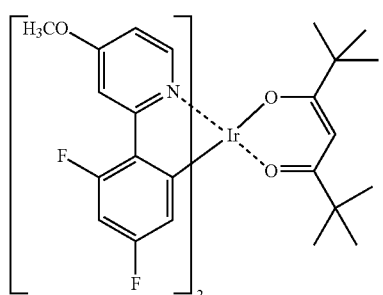

PD3

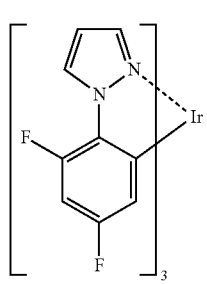

PD4

-continued

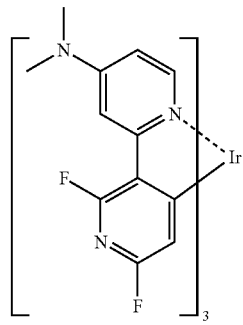

PD5

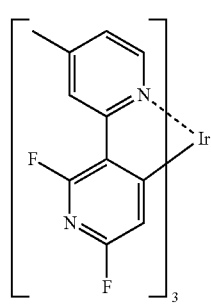

PD6

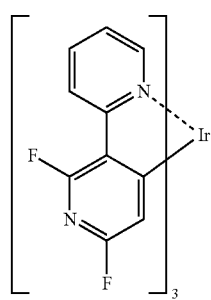

PD7

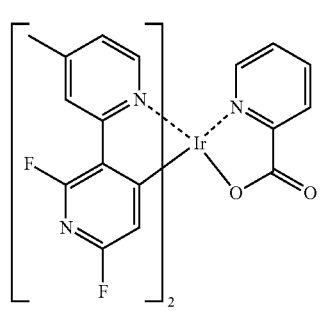

PD8

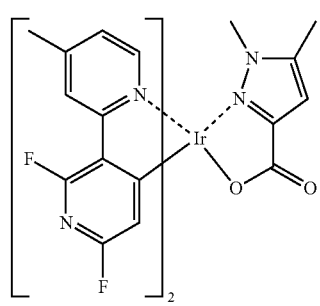

PD9

-continued
PD10
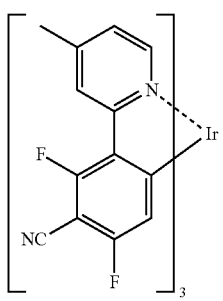
PD11
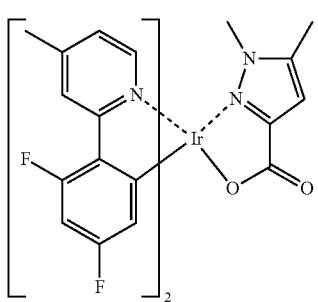
PD12
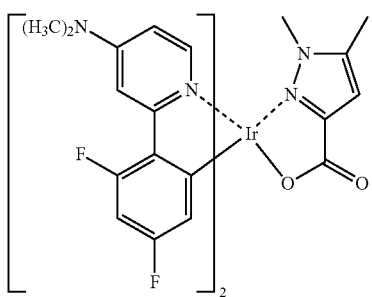
PD13
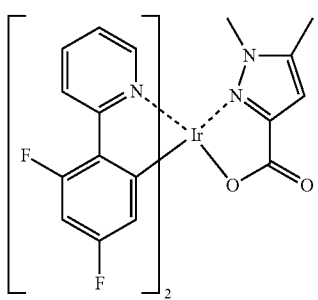
PD14
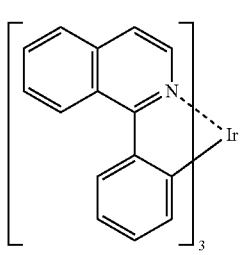
-continued
PD15
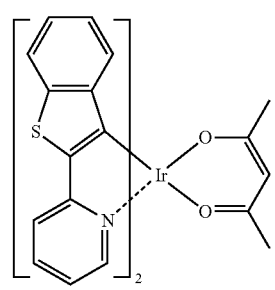
PD16
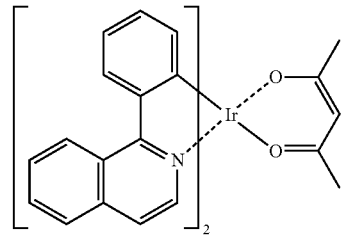
PD17
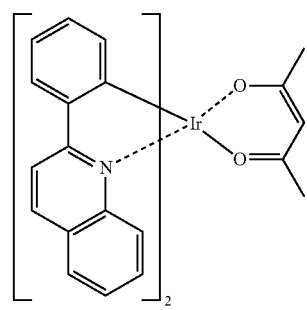
PD18
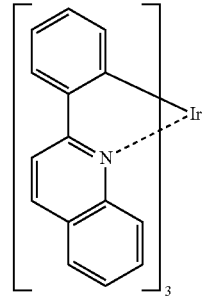
PD19
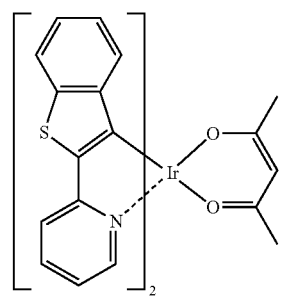

PD20 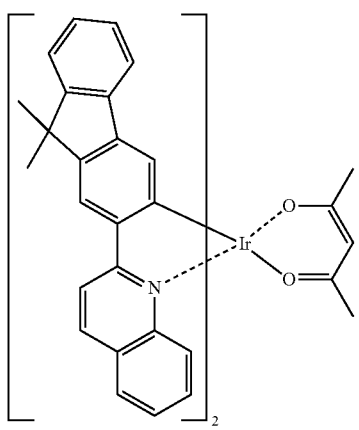
PD21 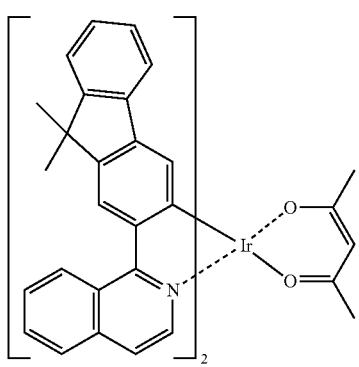
PD22 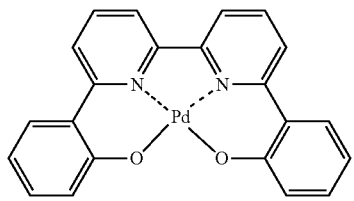
PD23 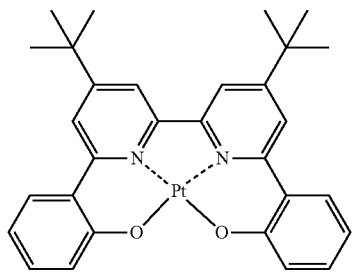
PD24 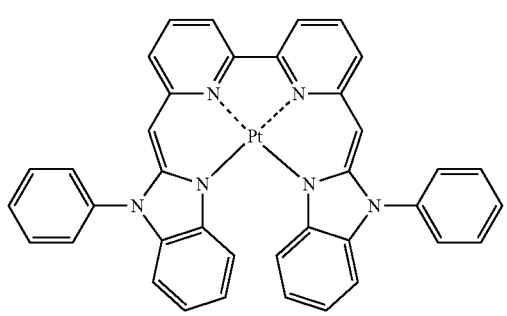
PD25 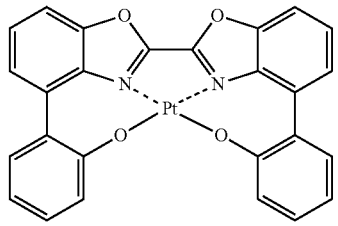
PD26 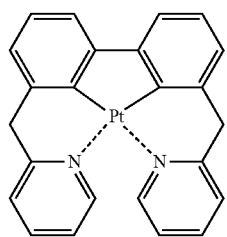
PD27 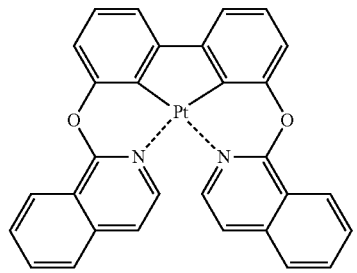
PD28 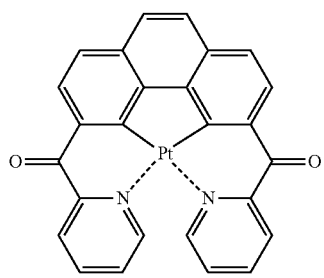
PD29 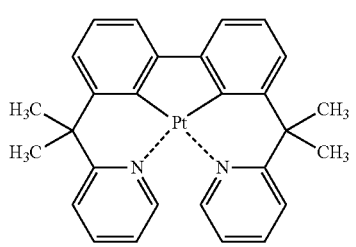
PD30 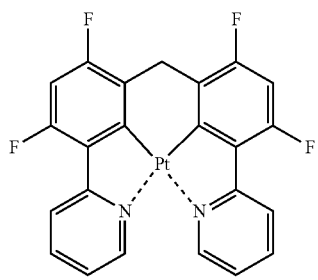

-continued
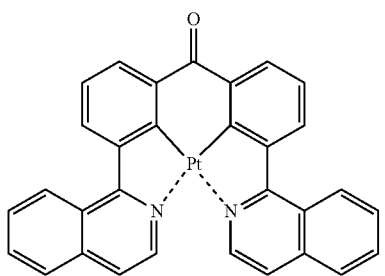
PD31
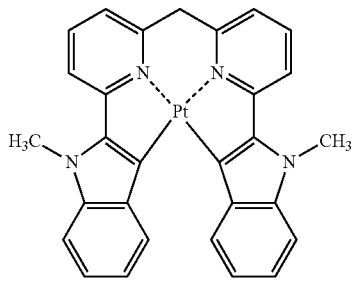
PD32
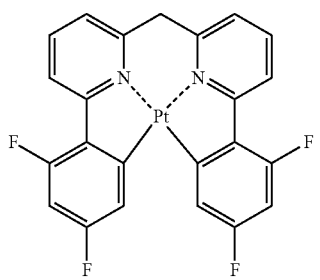
PD33
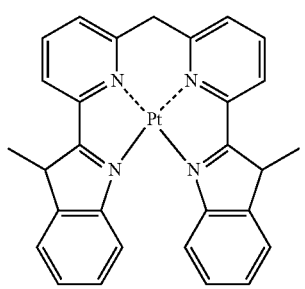
PD34
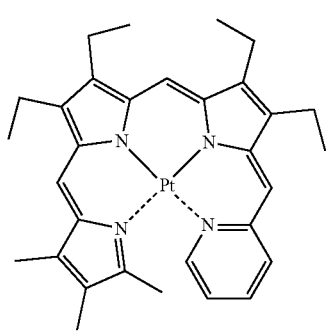
PD35
-continued
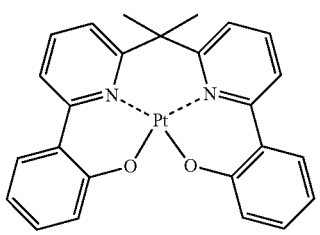
PD36
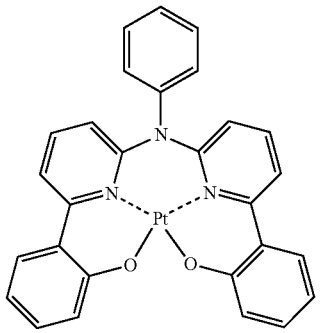
PD37
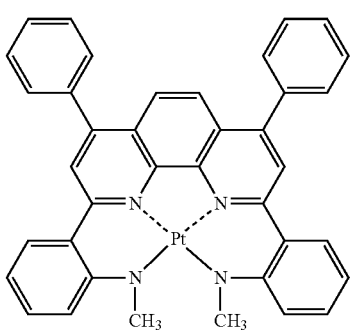
PD38
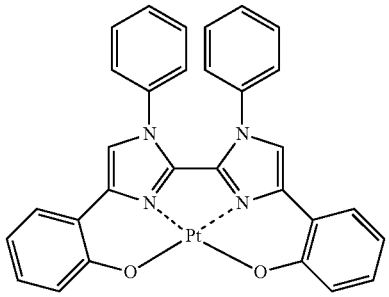
PD39
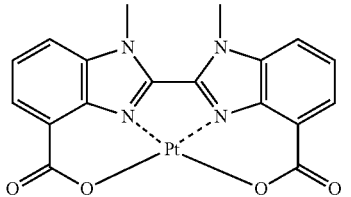
PD40
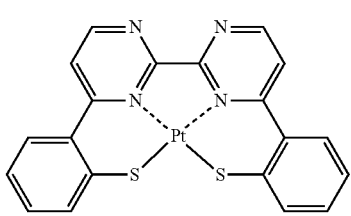
PD41

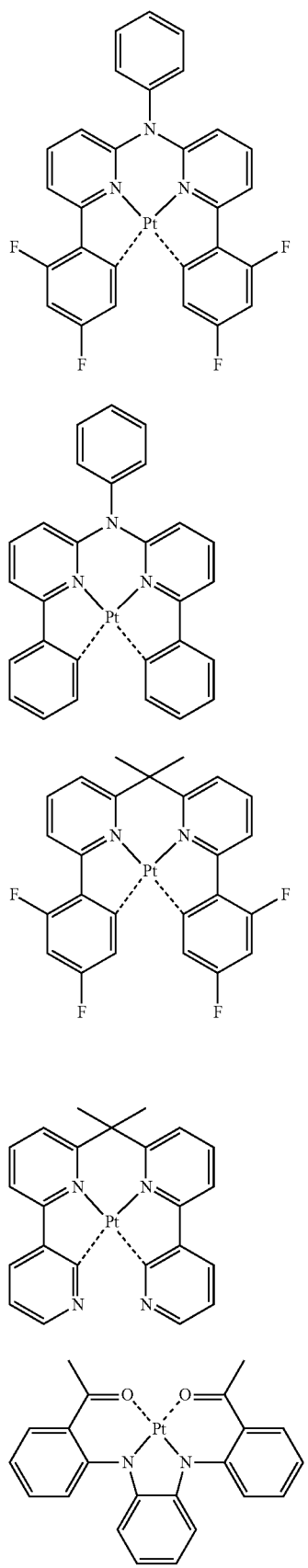

PD53 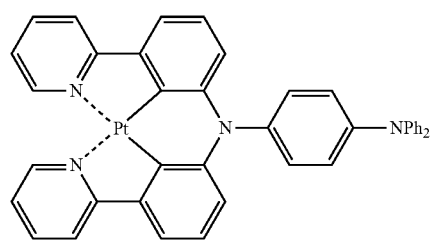
PD54 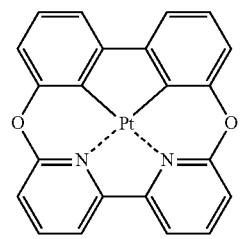
PD55 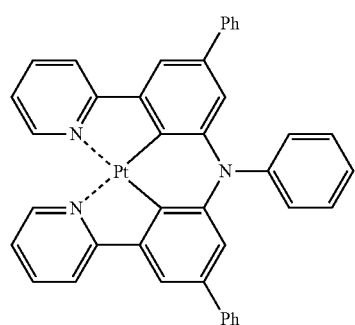
PD56 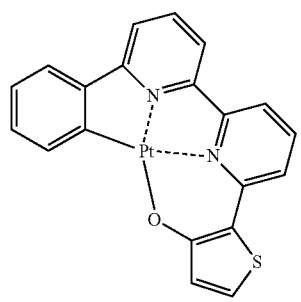
PD57 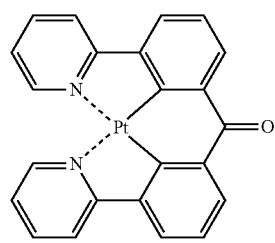
PD58 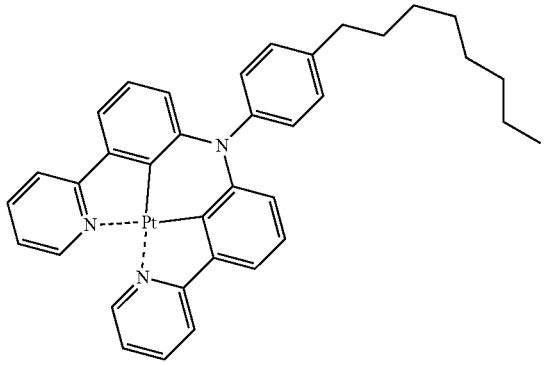
PD59 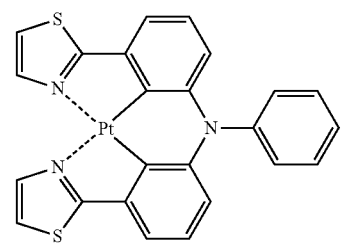
PD60 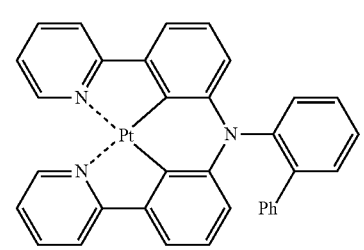
PD61 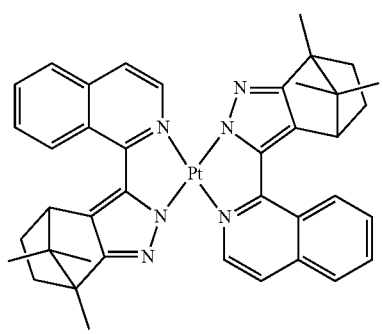
PD62 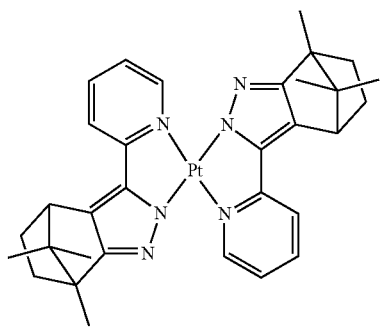

-continued
PD63
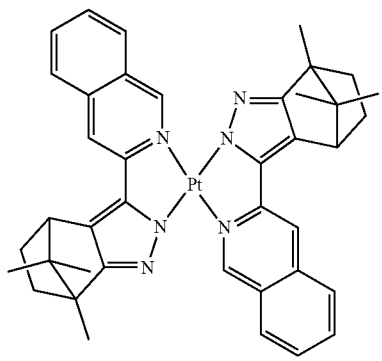
PD64
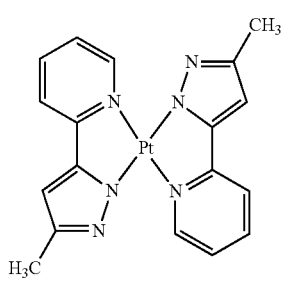
PD65
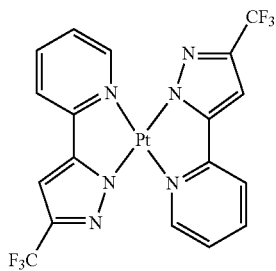
PD66
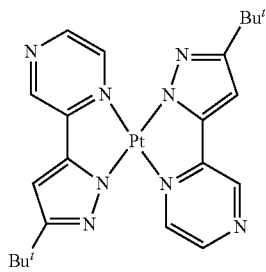
PD67
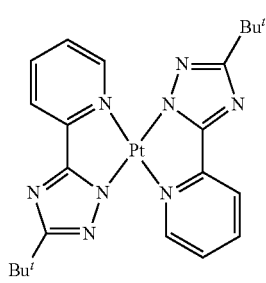
-continued
PD68
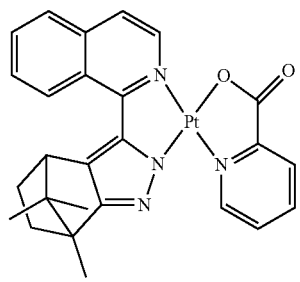
PD69
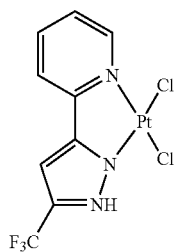
PD70
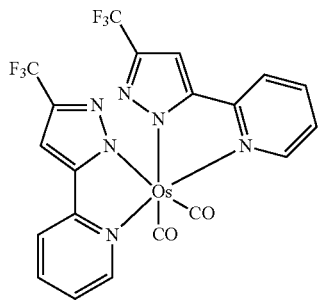
PD71
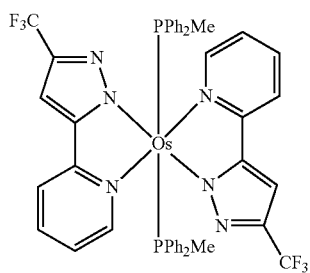
PD72
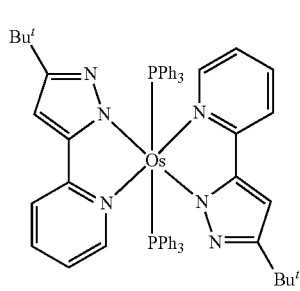

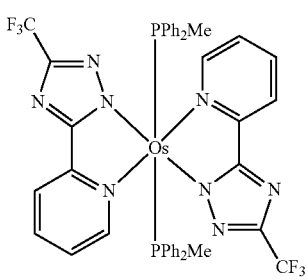
PD73

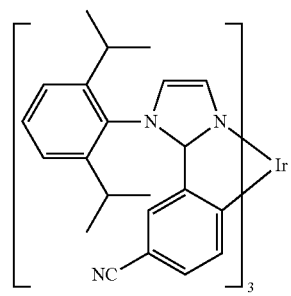
PD74

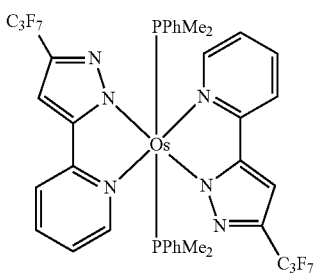
PD75

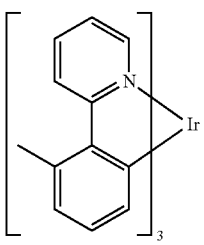
PD76

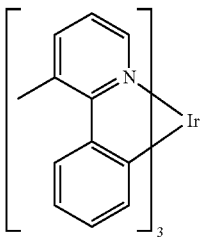
PD77

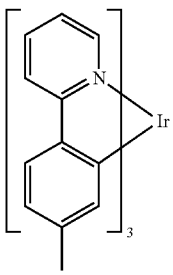
PD78

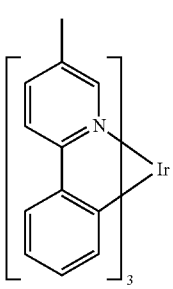

CIM02

Alternatively, the phosphorescent dopant may include PtOEP below:

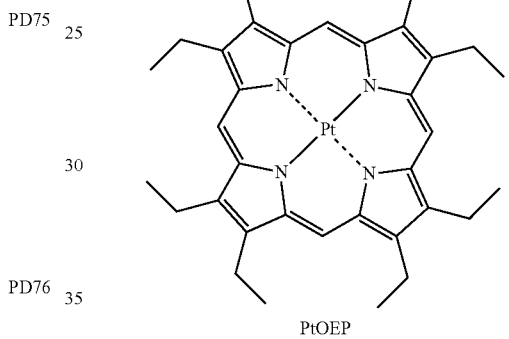

PtOEP

When the EML includes a host and a dopant, an amount of the dopant may be from about 0.01 to about 15 parts by weight, based on 100 parts by weight of the host, but is not limited thereto.

A thickness of the EML may be from about 100 Å to about 1,000 Å, e.g., about 200 Å to about 600 Å. When the thickness of the emission layer is within these ranges, excellent emission characteristics may be obtained without a substantial increase in driving voltage.

Next, the electron transport region may be disposed on the EML.

The electron transport region may include at least one of an HBL, an ETL, and an EIL.

For example, the electron transport region may have a structure of HBL/ETL/EIL or a structure of ETL/EIL, but the structure is not limited thereto. The ETL may have a single-layer structure or a multi-layer structure including a plurality of layers.

Conditions for forming an HBL, an ETL, and an EIL in the electron transport region may be understood by referring to conditions for forming the HIL.

When the electron transport region includes an HBL, the HBL may include, for example, at least one of BCP, Bphen, and Compound PBH021 below, but is not limited thereto:

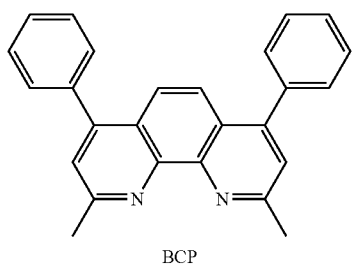
BCP

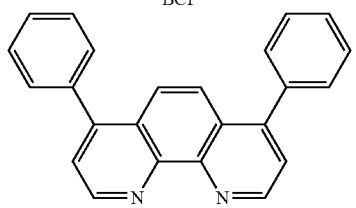
Bphen

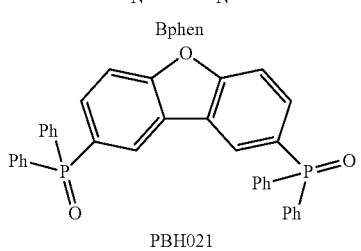
PBH021

A thickness of the HBL may be from about 20 Å to about 1,000 Å, e.g., about 30 Å to about 300 Å. When the thickness of the HBL is within these ranges, excellent hole blocking characteristics may be obtained without a substantial increase in driving voltage.

The ETL may further include at least one of BCP and Bphen above and $Alq_3$, Balq, TAZ, and NTAZ below:

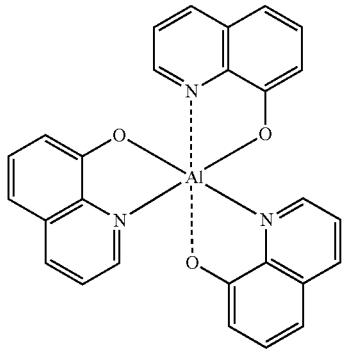
$Alq_3$

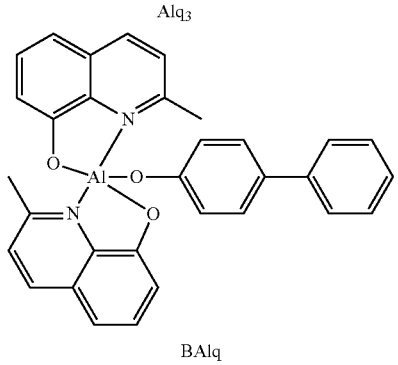
BAlq

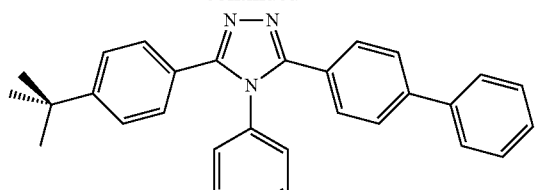
TAZ

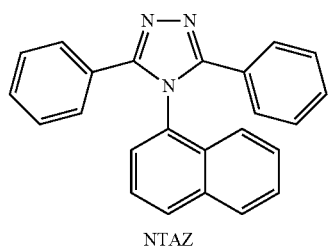
NTAZ

Alternatively, the ETL may include at least one of Compounds ET1, ET2, and ET3 below, but is not limited thereto:

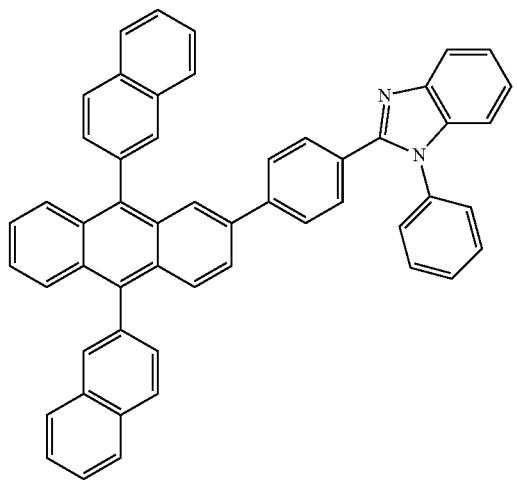
ET1

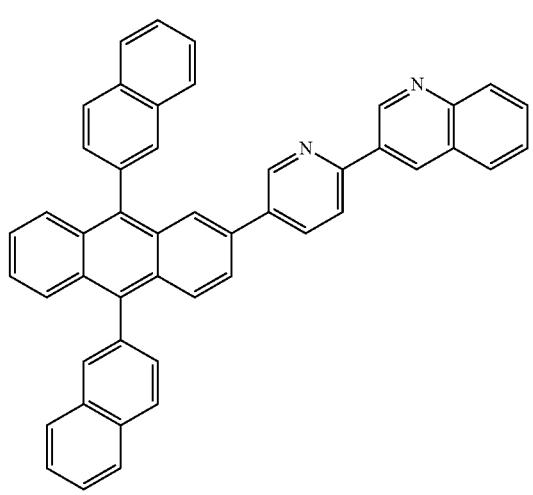
ET2

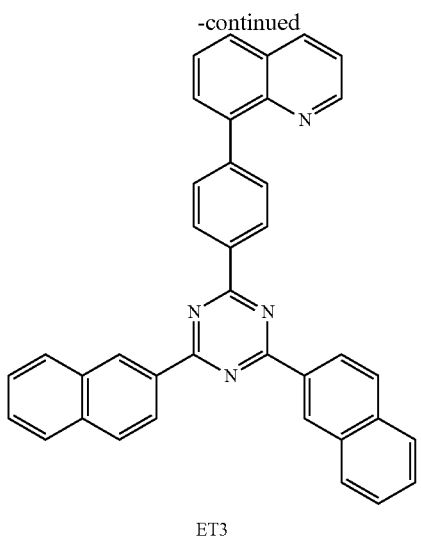

ET3

A thickness of the ETL may be from about 100 Å to about 1,000 Å, e.g., about 150 Å to about 500 Å. When the thickness of the ETL is within these ranges, excellent electron transporting characteristics may be obtained without a substantial increase in driving voltage.

In addition to the materials described above, the ETL may further include a metal-containing material.

The metal-containing material may include a Li complex. The Li complex may include, for example, Compound ET-D1 (e.g., lithium quinolate (LiQ) or ET-D2 below:

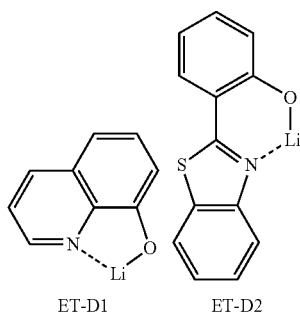

ET-D1          ET-D2

The electron transport region may include an EIL that facilitates electron injection from the second electrode 19.

The EIL may include at least one selected from LiF, NaCl, CsF, $Li_2O$, and BaO.

A thickness of the EIL may be from about 1 Å to about 100 Å, e.g., about 3 Å to about 90 Å. When the thickness of the EIL is within these ranges, satisfactory electron injecting characteristics may be obtained without a substantial increase in driving voltage.

The second electrode 19 may be disposed on top of the organic layer 15. The second electrode 19 may be a cathode. A material for forming the second electrode 19 may be a material having a low work function, such as a metal, an alloy, an electrically conductive compound, or a mixture thereof. Detailed examples of the material for forming the second electrode 19 may include lithium (Li), magnesium (Mg), aluminum (Al), aluminum-lithium (Al—Li), calcium (Ca), magnesium-indium (Mg—In), and magnesium-silver (Mg—Ag). Alternatively, the material for forming the second electrode 19 may be ITO or IZO. The second electrode 19 may be a semi-reflective electrode or a transmissive electrode.

Hereinbefore, the organic light-emitting device has been described with reference to FIG. 1, but is not limited thereto.

A $C_1$-$C_{60}$ alkyl group as used herein refers to a linear or branched aliphatic hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —$OA_{101}$ (wherein $A_{101}$ is the $C_1$-$C_{60}$ alkyl group). Detailed examples thereof are a methoxy group, an ethoxy group, and an isopropyloxy group.

A $C_2$-$C_{60}$ alkenyl group as used herein refers to a hydrocarbon aliphatic group formed by including at least one carbon double bond in the middle or at the terminal of the $C_2$-$C_{60}$ alkyl group as defined above. Detailed examples thereof are an ethenyl group, a propenyl group, and a butenyl group. A $C_2$-$C_{60}$ alkenylene group as used herein refers to a divalent group having the same structure as the $C_2$-$C_{60}$ alkenyl group.

A $C_2$-$C_{60}$ alkynyl group as used herein refers to a hydrocarbon group formed by including at least one carbon triple bond in the middle or at the terminal of the $C_2$-$C_{60}$ alkyl group. Detailed examples thereof are an ethynyl group and a propynyl group. A $C_2$-$C_{60}$ alkynylene group as used herein refers to a divalent group having the same structure as the $C_2$-$C_{60}$ alkynyl group.

A $C_3$-$C_{10}$ cycloalkyl group as used herein refers to a monovalent hydrocarbon monocyclic group having 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as the $C_3$-$C_{10}$ cycloalkyl group.

A $C_1$-$C_{10}$ heterocycloalkyl group as used herein refers to a monovalent monocyclic group having at least one heteroatom selected from N, O, P, and S as a ring-forming atom and 1 to 10 carbon atoms. Detailed examples thereof are a tetrahydrofuranyl group and a tetrahydrothiophenyl group. A $C_1$-$C_{10}$ heterocycloalkylene group as used herein refers to a divalent group having the same structure as the $C_1$-$C_{10}$ heterocycloalkyl group.

A $C_3$-$C_{10}$ cycloalkenyl group as used herein refers to a monovalent monocyclic group that has 3 to 10 carbon atoms and at least one double bond in the ring thereof, and which is not aromatic. Detailed examples thereof are a cyclopentenyl group, a cyclohexenyl group, and a cycloheptenyl group. A $C_3$-$C_{10}$ cycloalkenylene group as used herein refers to a divalent group having the same structure as the $C_3$-$C_{10}$ cycloalkenyl group.

A $C_1$-$C_{10}$ heterocycloalkenyl group as used herein refers to a monovalent monocyclic group that has at least one heteroatom selected from N, O, Si, P, and S as a ring-forming atom, 1 to 10 carbon atoms, and at least one double bond in its ring. Detailed examples of the $C_1$-$C_{10}$ heterocycloalkenyl group are a 2,3-dihydrofuranyl group and a 2,3-dihydrothiophenyl group. A $C_1$-$C_{10}$ heterocycloalkenylene group as used herein refers to a divalent group having the same structure as the $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group as used herein refers to a monovalent group having a carbocyclic aromatic system that has at least one heteroatom selected from N, O, P, and S as a ring-forming atom, and 1 to 60 carbon atoms. A $C_1$-$C_{60}$ heteroarylene group as used herein refers to a divalent group having a carbocyclic aromatic system that has at least one heteroatom selected from N, O, P, and S as a ring-forming atom, and 1 to 60 carbon atoms. Detailed examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

A monovalent non-aromatic condensed polycyclic group (e.g., a group having 8 to 60 carbon atoms) as used herein refers to a monovalent group that has two or more rings condensed to each other, has carbon atoms only as a ring-forming atom, and which is non-aromatic in the entire molecular structure. A detailed example of the monovalent non-aromatic condensed polycyclic group is a fluorenyl group. A divalent non-aromatic condensed polycyclic group as used herein refers to a divalent group having the same structure as the monovalent non-aromatic condensed polycyclic group.

A monovalent non-aromatic condensed heteropolycyclic group (e.g., a group having 1 to 60 carbon atoms) as used herein refers to a monovalent group that has two or more rings condensed to each other, has heteroatoms as a ring-forming atom selected from N, O, P, and S in addition to C, and which is non-aromatic in the entire molecular structure. A detailed example of the monovalent non-aromatic condensed heteropolycyclic group is a carbazolyl group. A divalent non-aromatic condensed heteropolycyclic group as used herein refers to a divalent group having the same structure as the monovalent non-aromatic condensed heteropolycyclic group.

At least one of substituents of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group (wherein the monovalent non-aromatic condensed heteropolycyclic group excludes a carbazolyl group), and —$Si(Q_{31})(Q_{32})(Q_{33})$, wherein $Q_1$ to $Q_3$, $Q_{11}$ to $Q_{13}$, $Q_{21}$ to $Q_{23}$, and $Q_{31}$ to $Q_{33}$ may be each independently selected from a hydrogen, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group (wherein the monovalent non-aromatic condensed heteropolycyclic group excludes a carbazolyl group).

The term "a biphenyl group" as used herein refers to "a phenyl group substituted with a phenyl group".

Hereinafter, the organic light-emitting device according to embodiments is described in detail with reference to Synthesis Example and Examples. The wording "B was used instead of A" used in describing Synthesis Examples means that a molar equivalent of A was identical to a molar equivalent of B.

EXAMPLE

Synthesis Example 1: Synthesis of Compound 5

10 g (46 mmol) of 3,6-dicyanocarbazole, 13.9 g of 2-bromodibenzo[b,d]furan, 8.8 g of CuI, 15.9 g of $K_2CO_3$, and 2.5 g of 1,10-phenanthroline were added to a 250 mL two-necked flask, and 100 mL of dimethylformamide (DMF) was added thereto. The mixture was stirred at a temperature of 150° C. for 28 hours, and the resulting solution was cooled and filtered using a celite pad. The filtrate obtained therefrom was evaporated in vacuum. The resulting product was purified using silica gel column including methylene chloride (MC)/Hexane solvent as a developing solution, and refined by recrystallization in the presence of MC/Acetone, thereby obtaining 9.5 g (yield=54%) of Compound 5.

Mass: calc. 383.11. found [M+H$^+$] 384.12.

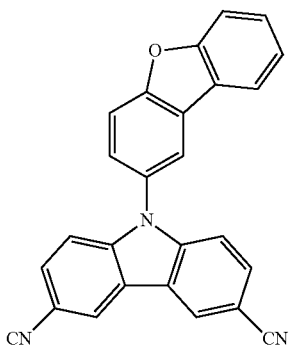

Synthesis Example 2: Synthesis of Compound 9

Compound 9 was synthesized in the same manner as in Synthesis Example 1, except that 13.1 g of 2-bromodibenzo[b,d]thiophene was used instead of 2-bromodibenzo[b,d]furan.
Mass: calc. 399.08. found [M+H$^+$] 400.08.

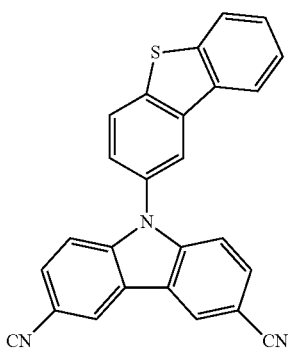

Synthesis Example 3: Synthesis of Compound 13

Compound 13 was synthesized in the same manner as in Synthesis Example 1, except that 17.0 g of 3-bromo-9-phenyl-9H-carbazole was used instead of 2-bromodibenzo[b,d]furan.
Mass: calc. 458.15. found [M+H$^+$] 459.16.

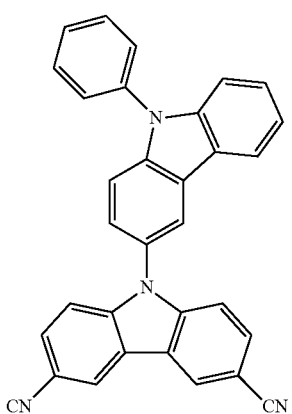

Synthesis Example 4: Synthesis of Compound 18

Compound 18 was synthesized in the same manner as in Synthesis Example 1, except that 3-bromo-9,9-dimethyl-9H-fluorene was used instead of 2-bromodibenzo[b,d]furan.
Mass: calc. 409.16. found [M+H$^+$] 410.17.

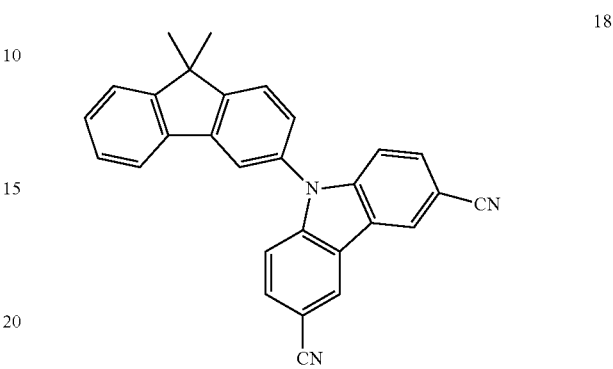

Synthesis Example 5: Synthesis of Compound 49

Compound 49 was synthesized in the same manner as in Synthesis Example 1, except that 17.0 g of 2-(3-bromophenyl)dibenzo[b,d]furan was used instead of 2-bromodibenzo[b,d]furan.
Mass: calc. 459.14. found [M+H$^+$] 460.15.

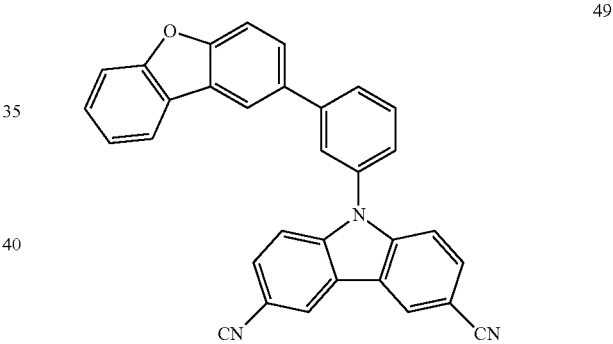

Synthesis Example 6: Synthesis of Compound 60

Compound 60 was synthesized in the same manner as in Synthesis Example 1, except that 14.4 g of 8-bromodibenzo[b,d]furan-2-carbonitrile was used instead of 2-bromodibenzo[b,d]furan.
Mass: calc. 408.10. found [M+H$^+$] 409.11.

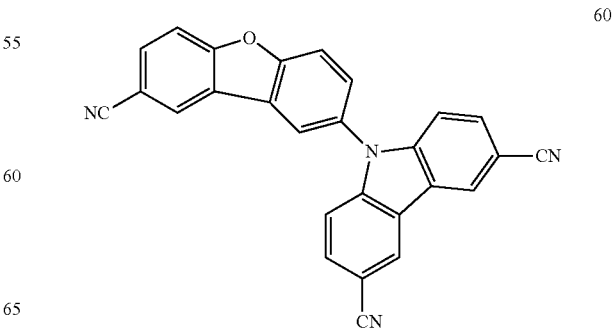

Synthesis Example 7: Synthesis of Compound 64

Compound 64 was synthesized in the same manner as in Synthesis Example 1, except that Intermediate A and 7.5 g of 9H-pyrido[2,3-b]indole (α-carboline) was used instead of 2-bromodibenzo[b,d]furan and 3,6-dicyanocarbazole, respectively.

Mass: calc. 435.14. found [M+H$^+$] 436.15.

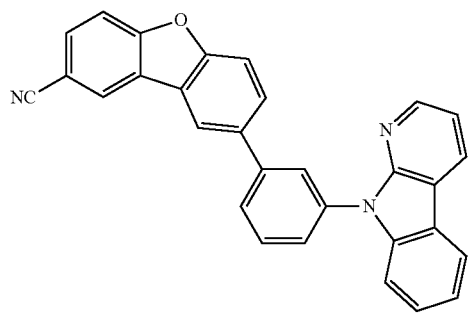

64

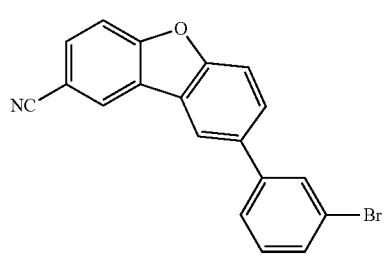

Intermediate A

Evaluation Example 1: Evaluation of HOMO, LUMO and T$_1$ Energy Levels

According to methods described in Table 2 below, HOMO, LUMO and T$_1$ energy levels of Compounds 9 and 18 were evaluated, and results are shown in Table 3 below.

TABLE 2

| | |
|---|---|
| HOMO energy level evaluation | Cyclic voltammetry (CV) (electrolyte: 0.1M Bu$_4$NClO$_4$/solvent: CH$_2$Cl$_2$/ electrode: 3 electrode system (working electrode: GC, standard electrode: Ag/AgCl, auxiliary electrode: Pt)) is used to draw a potential (V) - current (A) graph regarding each compound. Based on reduction onset values of the graph, HOMO energy levels for each compound are calculated. |
| LUMO energy level evaluation | Each compound is diluted with CHCl$_3$ to a concentration of 1 × 10$^{-5}$ M, and Shimadzu UV-350 Spectrometer is used to measure UV absorption spectrum of each compound at room temperature. LUMO energy levels for each compound are calculated using optical band gap (Eg) values of the edge of the absorption spectrum. |
| T$_1$ energy level evaluation | A mixture of toluene and each compound (prepared by dissolving 1 milligram (mg) of each compound in 3 cubic centimeters (cc) of toluene) is added to a quartz cell, and liquid nitrogen (77 Kelvins (K)) is added thereto to obtain photoluminence spectrum using a photoluminence measuring device. In comparison with typical photoluminence spectrum at room temperature, peaks that are observed only at low temperatures are analyzed to calculate T$_1$ energy levels of each compound. |

TABLE 3

| Compound No. | HOMO (eV) (found) | LUMO (eV) (found) | T$_1$ energy level (eV) |
|---|---|---|---|
| 9 | −6.25 | −2.76 | 2.99 |
| 18 | −6.01 | −2.54 | 2.81 |

Referring to Table 3 above, it was confirmed that each compound had appropriate electric characteristics to be used as a material for forming the organic light-emitting device.

Example 1

A glass substrate on which an ITO electrode (i.e., a first electrode or an anode) was formed to a thickness of 1,500 Angstroms (Å) was ultrasonically washed with distilled water. After the washing using distilled water was completed, the glass substrate was ultrasonically washed with isopropyl alcohol, acetone, and methanol and dried. The glass substrate was transported to a plasma washing machine to be cleaned for 5 minutes, and then, transported to a vacuum evaporator.

Compounds HT3 and HP-1 were co-deposited on the ITO electrode of the glass substrate to form an HIL having a thickness of 100 Å. Compound HT3 was deposited on the HIL to form an HTL having a thickness of 1,300 Å. mCP was disposed on the HTL to form an EBL having a thickness of 150 Å, thereby forming a hole transport region.

Compound 9 as a host and CIM02 (10 percent by weight (wt %)) as a dopant were co-deposited on the hole transport region to form an EML having a thickness of 300 Å.

PBH021 was deposited on the EML to form an HBL having a thickness of 100 Å. Compounds ET3 and Liq were vacuum co-deposited on the EBL to form an ETL having a thickness of 250 Å. Liq was deposited on the ETL to form an EIL having a thickness of 5 Å, and Al was deposited on the EIL to form a second electrode (i.e., a cathode) having a thickness of 1,000 Å, thereby forming an organic light-emitting device.

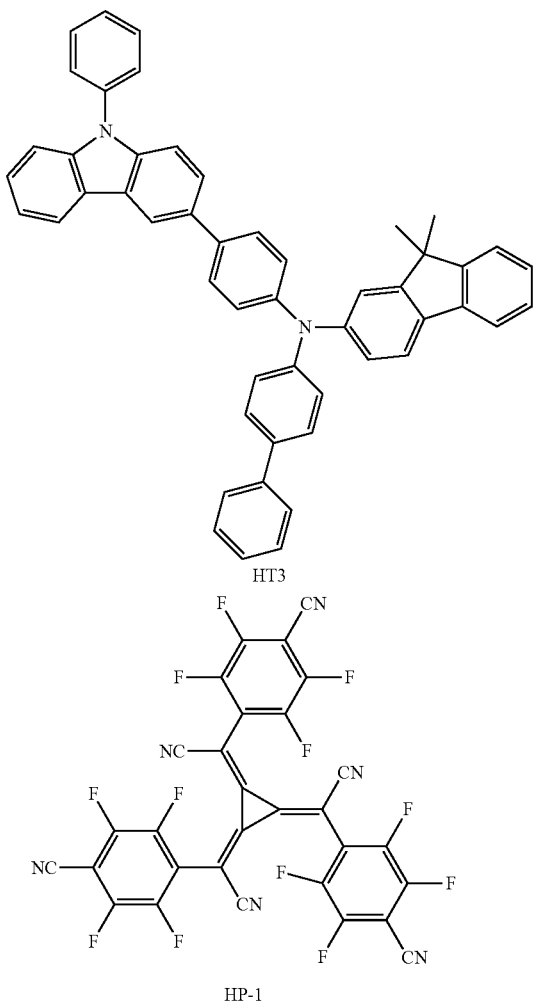

HT3

HP-1

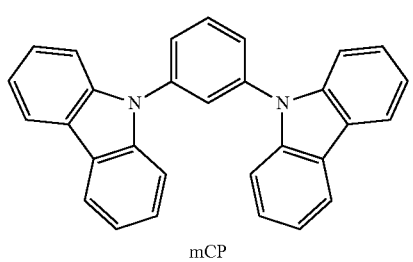

mCP

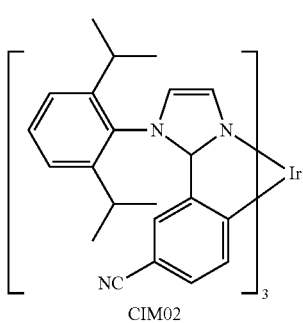

CIM02

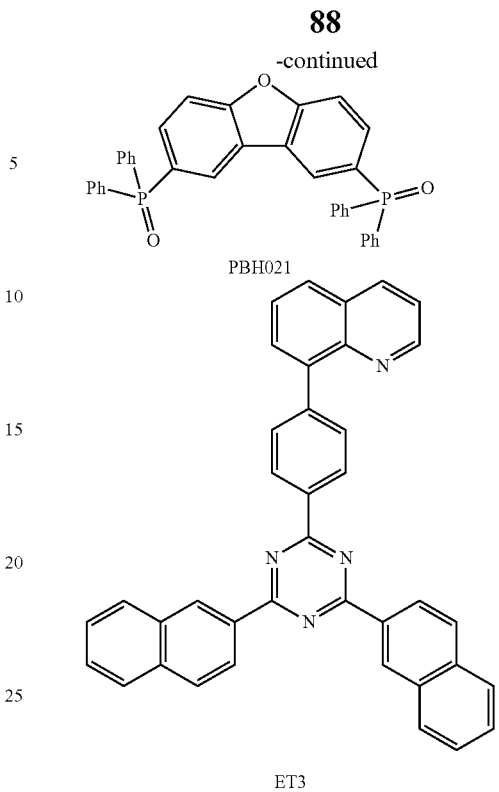

PBH021

ET3

Examples 2 and 3 and Comparative Examples 1 to 4

Organic light-emitting devices were manufactured in the same manner as in Example 1, except that in forming the EML, compounds listed in Table 4 below were used as a host, respectively, instead of Compound 9.

Evaluation Example 4: Evaluation of Characteristics of Organic Light-Emitting Device The organic light-emitting devices of Examples 1 to 3 and Comparative Examples 1 to 4 were evaluated in terms of driving voltage, efficiency, electric power, quantum efficiency and lifespan, by using a current-voltage measuring device (Keithley 2400) and a luminance meter (Minolta Cs-1000A), and results are shown in Table 4 below. In Table 4, $T_{95}$ (at 500 candelas per meter ($cd/m^2$)) refers to lifespan data measured when luminance of the organic light-emitting device reached 95% with respect to initial luminance 100%.

TABLE 4

| | Host | Driving voltage (V) | Efficiency (cd/A) | Electric power (lm/W) | Quantum efficiency (%) | $T_{95}$ (hr) |
|---|---|---|---|---|---|---|
| Example 1 | Compound 9 | 5.2 | 32.3 | 19.5 | 17.2 | 32.3 |
| Example 2 | Compound 13 | 5.4 | 30.4 | 17.7 | 16.2 | 30.4 |
| Example 3 | Compound 18 | 5.3 | 34.3 | 20.3 | 18.2 | 34.3 |
| Comparative Example 1 | Compound A | 6.8 | 11.2 | 5.2 | 6.0 | 11.2 |
| Comparative Example 2 | Compound B | 8.3 | 13.4 | 5.1 | 7.1 | 13.4 |

TABLE 4-continued

| | Host | Driving voltage (V) | Efficiency (cd/A) | Electric power (lm/W) | Quantum efficiency (%) | T95 (hr) |
|---|---|---|---|---|---|---|
| Comparative Example 3 | Compound C | 6.1 | 18.4 | 9.6 | 9.8 | 18.4 |
| Comparative Example 4 | Compound D | 7.3 | 29.2 | 12.6 | 15.5 | 29.2 |

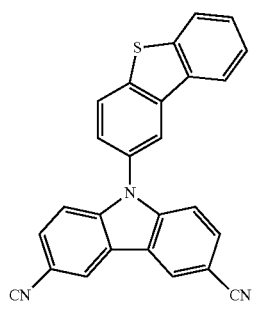

9

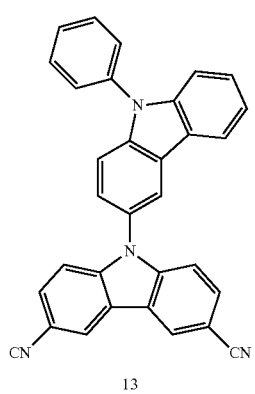

13

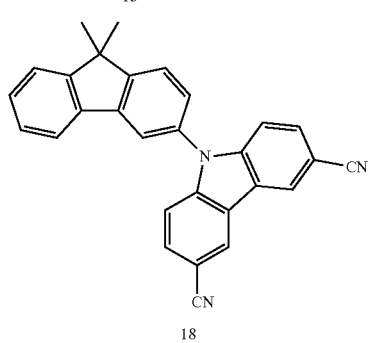

18

Compound A

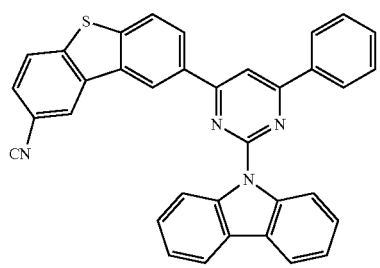

TABLE 4-continued

| | Host | Driving voltage (V) | Efficiency (cd/A) | Electric power (lm/W) | Quantum efficiency (%) | T95 (hr) |
|---|---|---|---|---|---|---|

Compound B

Compound C

Compound D

Referring to Table 4 above, it was confirmed that the organic light-emitting devices of Examples 1 to 3 had excellent characteristics, such as low driving voltage, high efficiency, high electric power, high quantum efficiency, and long lifespan, as compared with those parameters of the organic light-emitting devices of Comparative Examples 1 to 4.

As described above, according to the one or more of the above embodiments of the present disclosure, a condensed cyclic compound has excellent electrical characteristics and thermal stability, and accordingly, an organic light-emitting device including the condensed cyclic compound has low driving voltage, high efficiency, high electric power, high quantum efficiency, and long lifespan characteristics.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present disclosure have been described with reference to the figures, it will be understood by those of ordinary skill in the art that various changes in form and details may be made therein without departing from the spirit and scope of the present disclosure as defined by the following claims.

What is claimed is:
1. A condensed cyclic compound represented by Formulae 1A or 1B:

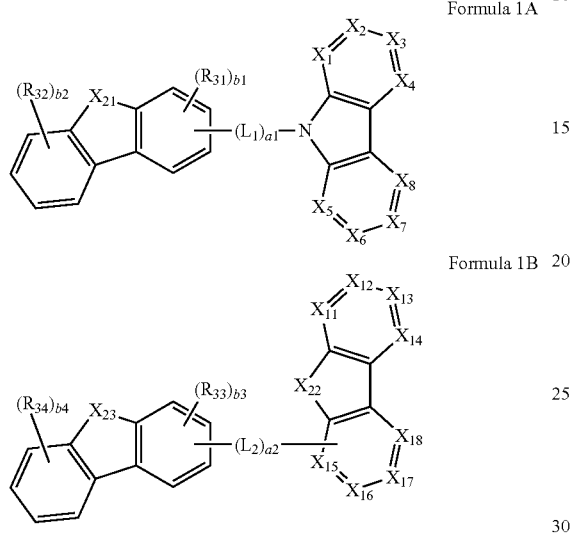

Formula 1A

Formula 1B wherein in Formulae 1A and 1B,
$X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$, $X_8$ is N or $C(R_8)$, $X_{11}$ is N or $C(R_{11})$, $X_{12}$ is N or $C(R_{12})$, $X_{13}$ is N or $C(R_{13})$, $X_{14}$ is N or $C(R_{14})$, $X_{15}$ is N, C or $C(R_{15})$, $X_{16}$ is N, C or $C(R_{16})$, $X_{17}$ is N, C, or $C(R_{17})$, and $X_{18}$ is N, C, or $C(R_{18})$, and when $X_{15}$ is C, $X_{15}$ is connected with *-$(L_2)_{a2}$-*', when $X_{16}$ is C, $X_{16}$ is connected with *-$(L_2)_{a2}$-*', when $X_{17}$ is C, $X_{17}$ is connected with *-$(L_2)_{a2}$-*', and when $X_{18}$ is C, $X_{18}$ is connected with *-$(L_2)_{a2}$-*',
$X_{21}$ is selected from O, S, Se, $C(R_{21})(R_{22})$, $Si(R_{21})(R_{22})$, and $N(R_{23})$,
$X_{22}$ is selected from O, S, Se, $C(R_{24})(R_{25})$, $Si(R_{24})(R_{25})$, and $N(R_{26})$,
$X_{23}$ is selected from O, S, Se, $C(R_{27})(R_{28})$, and $Si(R_{27})(R_{28})$,
$L_1$ and $L_2$ are each independently selected from
a phenylene group, a pyridinylene group, a fluorenylene group, a dibenzofuranylene group, and a dibenzothiophenylene group;
a phenylene group, a pyridinylene group, a fluorenylene group, a dibenzofuranylene group, and a dibenzothiophenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —Si($Q_1$)($Q_2$)($Q_3$); and
—Si($R_{41}$)($R_{42}$)—, —O—, —S—, and —Se—,
wherein a1 and a2 are each independently an integer selected from 0 to 5, and when a1 is 2 or more, 2 or more groups $L_1$ are identical to or different from each other, and when a2 is 2 or more, 2 or more groups $L_2$ are identical to or different from each other,
provided that when a1 is 1, $L_1$ is selected from
a phenylene group, a fluorenylene group, a dibenzofuranylene group, and a dibenzothiophenylene group;
a phenylene group, a fluorenylene group, a dibenzofuranylene group, and a dibenzothiophenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —Si($Q_1$)($Q_2$)($Q_3$);
$R_1$ to $R_8$, $R_{11}$ to $R_{18}$, and $R_{31}$ to $R_{34}$ are each independently selected from
a hydrogen, a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;
a $C_1$-$C_{20}$ alkyl group and a $C_1$-$C_{20}$ alkoxy group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;
a phenyl group, a pyridinyl group, a fluorenyl group, a dibenzofuranyl group, and a dibenzothiophenyl group;
a phenyl group, a pyridinyl group, a fluorenyl group, a dibenzofuranyl group, and a dibenzothiophenyl group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —Si($Q_{11}$)($Q_{12}$)($Q_{13}$); and
—Si($Q_{21}$)($Q_{22}$)($Q_{23}$), and
b1 and b3 are each independently 1, 2, or 3, and b2 and b4 are each independently 1, 2, 3, or 4, and when b1 is 2 or more, 2 or more groups $R_{31}$ are identical to or different from each other, when b2 is 2 or more, 2 or more groups $R_{32}$ are identical to or different from each other, when b3 is 2 or more, 2 or more groups $R_{33}$ are identical to or different from each other, and when b4 is 2 or more, 2 or more groups $R_{34}$ are identical to or different from each other,
in Formula 1A, i) at least one of $X_3$ and $X_7$ is C(CN), ii) at least one of groups $R_{31}$(s) in the number of b1 and groups $R_{32}$ in the number of b2 is a cyano group, or iii) at least one of $X_3$ and $X_7$ is C(CN) and at least one of groups $R_{31}$ in the number of b1 and groups $R_{32}$ in the number of b2 is a cyano group,
in Formula 1B, i) at least one of $X_{13}$ and $X_{17}$ is C(CN), ii) at least one of groups $R_{33}$ in the number of b3 and groups $R_{34}$ in the number of b4 is a cyano group, or iii))

at least one $X_{13}$ and $X_{17}$ is C(CN) and at least one of groups $R_{33}$ in the number of b3 and groups $R_{34}$ in the number of b4 is a cyano group, $R_{21}$ to $R_{29}$, $R_{41}$, $R_{42}$, $Q_1$ to $Q_3$, $Q_{11}$ to $Q_{13}$, and $Q_{21}$ to $Q_{23}$ are each independently selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a pyridinyl group, a fluorenyl group, a dibenzofuranyl group, and a dibenzothiophenyl group; and a phenyl group, a pyridinyl group, a fluorenyl group, a dibenzofuranyl group, and a dibenzothiophenyl group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group.

2. The condensed cyclic compound of claim 1, wherein in Formulae 1A, $X_1$ is $C(R_1)$, $X_2$ is $C(R_2)$, $X_3$ is $C(R_3)$, $X_4$ is $C(R_4)$, $X_5$ is $C(R_5)$, $X_6$ is $C(R_6)$, $X_7$ is $C(R_7)$, $X_8$ is $C(R_8)$, $X_{11}$ is $C(R_{11})$, $X_{12}$ is $C(R_{12})$, $X_{13}$ is $C(R_{13})$, and $X_{14}$ is $C(R_{14})$.

3. The condensed cyclic compound of claim 1, wherein $R_1$, $R_2$, $R_4$, $R_5$, $R_6$, and $R_8$ in Formula 1A are not a cyano group, and $R_{11}$, $R_{12}$, and $R_{14}$ in Formula 1B are not a cyano group.

4. The condensed cyclic compound of claim 1, wherein in Formula 1B, $X_{21}$ is selected from O, S, $C(R_{21})(R_{22})$, and $N(R_{23})$, $X_{22}$ is selected from O, S, $C(R_{24})(R_{25})$, and $N(R_{26})$, $X_{23}$ is selected from O, S, and $C(R_{27})(R_{28})$, $R_{21}$, $R_{22}$, $R_{24}$, $R_{25}$, $R_{27}$, and $R_{28}$ are each independently selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one of a deuterium, —F, and a cyano group;

a phenyl group, a pyridinyl group, a fluorenyl group, a dibenzofuranyl group, and a dibenzothiophenyl group; and a phenyl group, a pyridinyl group, a fluorenyl group, a dibenzofuranyl group, and a dibenzothiophenyl group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group, and $R_{23}$, $R_{26}$, and $R_{29}$ are each independently selected from a phenyl group, a pyridinyl group, a fluorenyl group, a dibenzofuranyl group, and a dibenzothiophenyl group; and a phenyl group, a pyridinyl group, a fluorenyl group, a dibenzofuranyl group, and a dibenzothiophenyl group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group.

5. The condensed cyclic compound of claim 1, wherein a1 and a2 are not 0.

6. The condensed cyclic compound of claim 1, wherein a1 and a2 are not 0, $L_1$ and $L_2$ are selected from groups represented by Formulae 2-1 to 2-18, groups $L_1$ in the number of a1 in Formula 1A comprises at least one of the groups of Formulae 2-3 to 2-18, and groups $L_2$ in the number of a2 in Formula 1B comprises at least one of the groups of Formulae 2-3 to 2-18

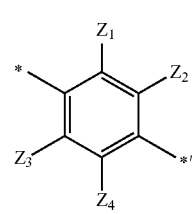

Formula 2-1

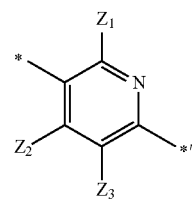

Formula 2-2

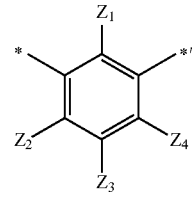

Formula 2-3

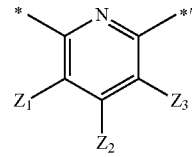

Formula 2-4

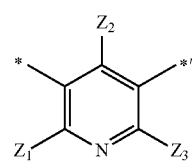

Formula 2-5

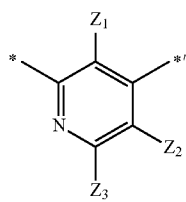
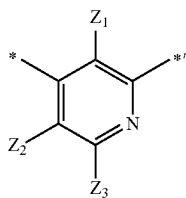
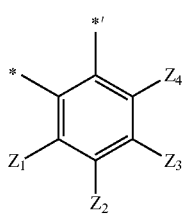
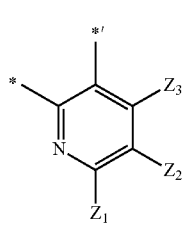
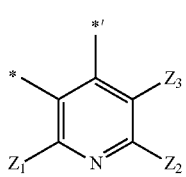
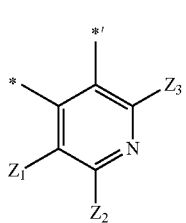
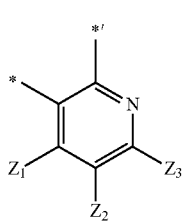
Formula 2-6
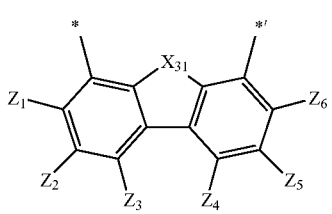
Formula 2-7
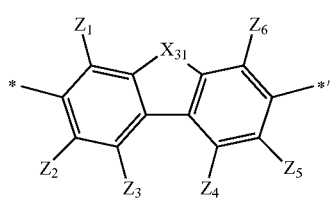
Formula 2-8
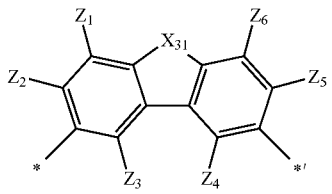
Formula 2-9
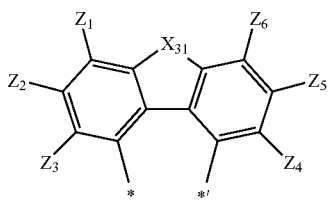
Formula 2-10
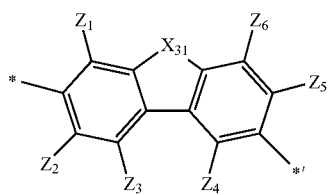
Formula 2-11
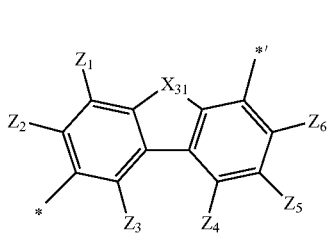
Formula 2-12
Formula 2-13
Formula 2-14
Formula 2-15
Formula 2-16
Formula 2-17
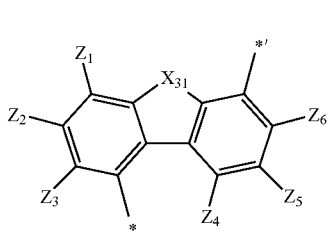

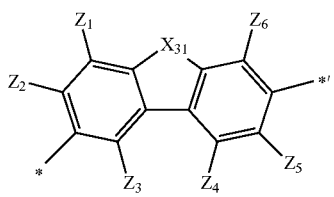

Formula 2-18 wherein in Formulae 2-1 to 2-18, $X_{31}$ is O, S, or $C(Z_7)(Z_8)$, and $Z_1$ to $Z_8$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —Si($Q_1$)($Q_2$)($Q_3$), wherein $Q_1$ to $Q_3$ are each independently selected from a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group.

7. The condensed cyclic compound of claim 6, wherein a1 and b1 are 1, and $L_1$ and $L_2$ are represented by Formula 2-3.

8. The condensed cyclic compound of claim 1, wherein $R_1$ to $R_8$, $R_{11}$ to $R_{18}$, and $R_{31}$ to $R_{34}$ are each independently selected from a hydrogen, a deuterium, —F, a hydroxyl group, a cyano group, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one of a deuterium, —F, a hydroxyl group and a cyano group;

a phenyl group, a pyridinyl group, a fluorenyl group, a dibenzofuranyl group, and a dibenzothiophenyl group;

a phenyl group, a pyridinyl group, a fluorenyl group, a dibenzofuranyl group, and a dibenzothiophenyl group, each substituted with at least one of a deuterium, —F, a hydroxyl group, cyano group, a $C_1$-$C_{10}$ alkyl group, a $C_1$-$C_{10}$ alkoxy group, a phenyl group, a pyridinyl group, a fluorenyl group, a dibenzofuranyl group, a dibenzothiophenyl group, and —Si($Q_{11}$)($Q_{12}$)($Q_{13}$); and —Si($Q_{21}$)($Q_{22}$)($Q_{23}$), wherein $Q_{11}$ to $Q_{13}$ and $Q_{21}$ to $Q_{23}$ are each independently selected from a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group.

9. The condensed cyclic compound of claim 1, represented by one of Formulae 1A(1) to 1A(4):

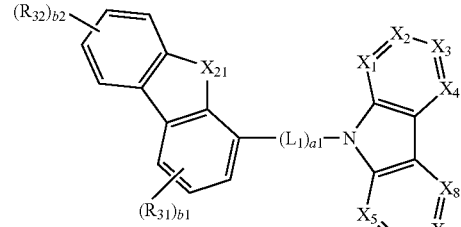

Formula 1A(1)

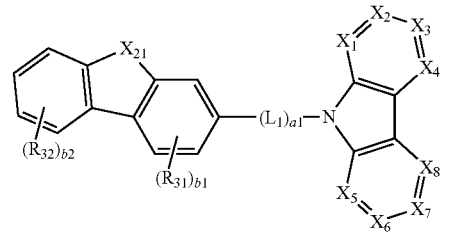

Formula 1A(2)

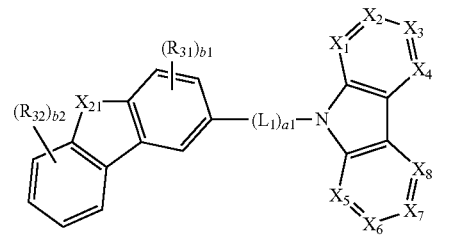

Formula 1A(3)

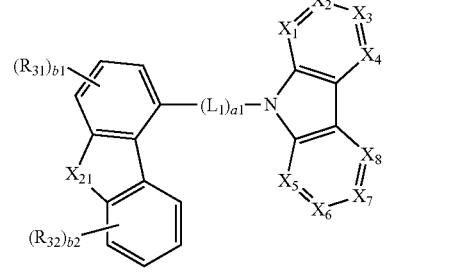

Formula 1A(4)

wherein, in Formulae 1A(1) to 1A(4), $X_1$ to $X_8$, $X_{21}$, $L_1$, a1, $R_{31}$, $R_{32}$, b1, and b2 are the same as in claim 1.

10. The condensed cyclic compound of claim 1, represented by one of Formulae 1A-A to 1A-D:

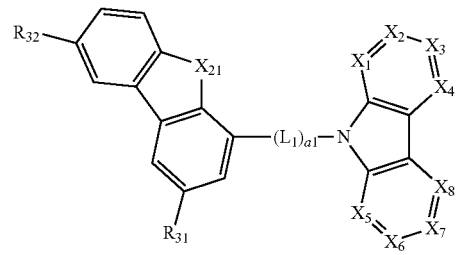

Formula 1A-A

Formula 1A-B
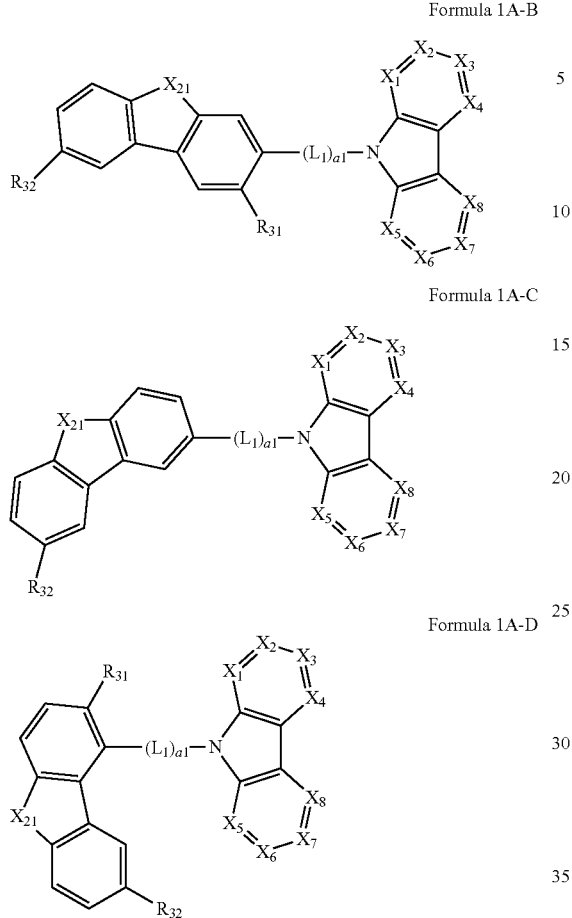
Formula 1A-C
Formula 1A-D
wherein, in Formulae 1A-A to 1A-D, $X_1$ to $X_8$, $X_{21}$, $L_1$, a1, $R_{31}$, and $R_{32}$ are the same as in claim 1.
11. The condensed cyclic compound of claim 1, represented by one of Formulae 1B(1) to 1B(16):
Formula 1B(1)
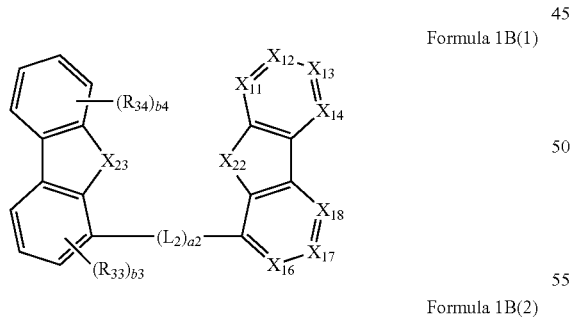
Formula 1B(2)
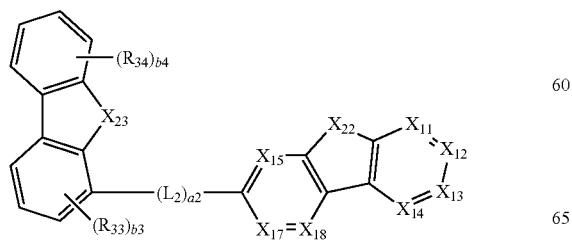
Formula 1B(3)
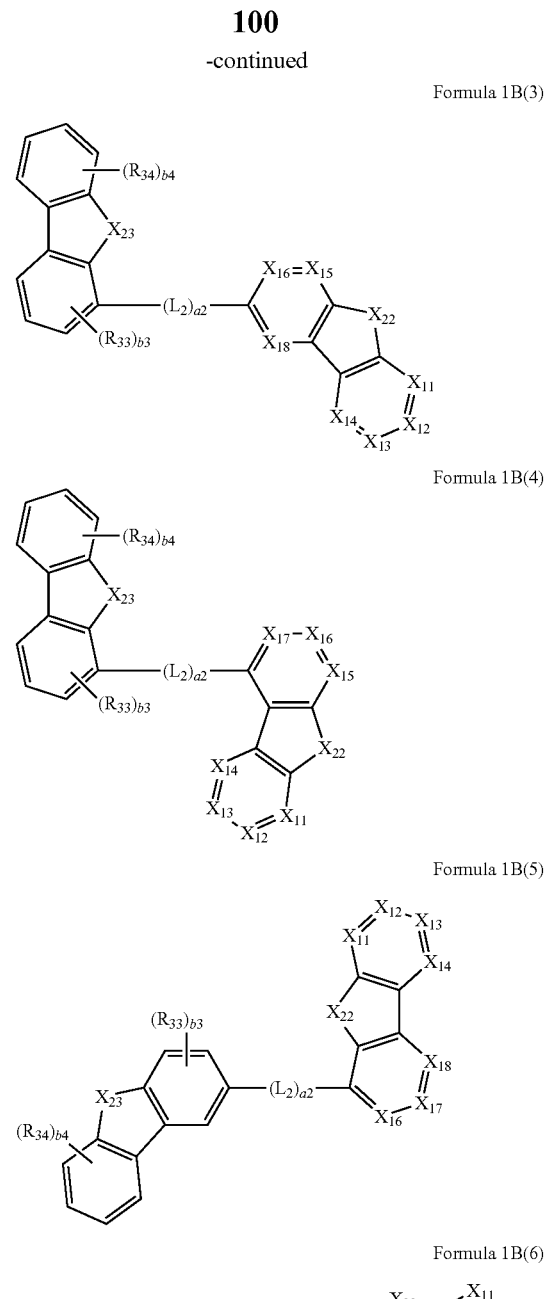
Formula 1B(4)
Formula 1B(5)
Formula 1B(6)
Formula 1B(7)
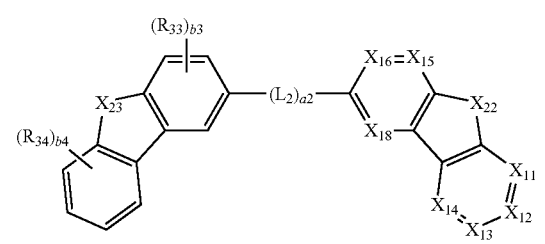

Formula 1B(8)
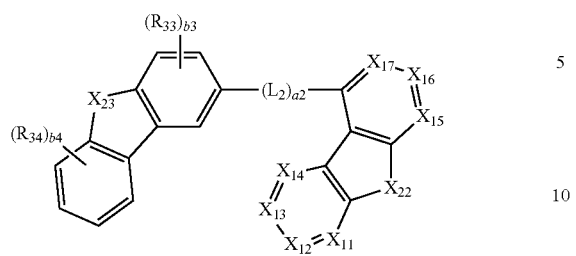
Formula 1B(9)
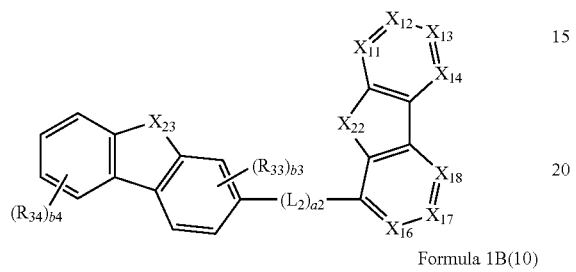
Formula 1B(10)
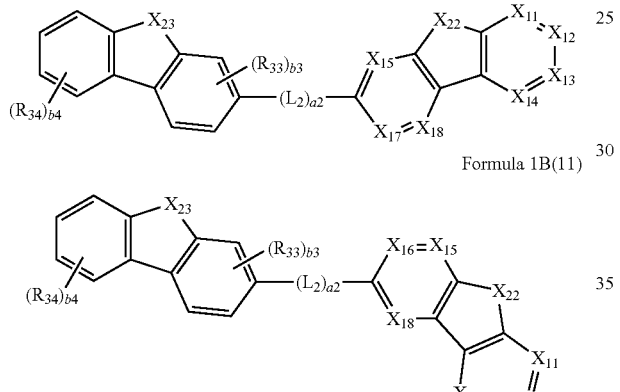
Formula 1B(11)
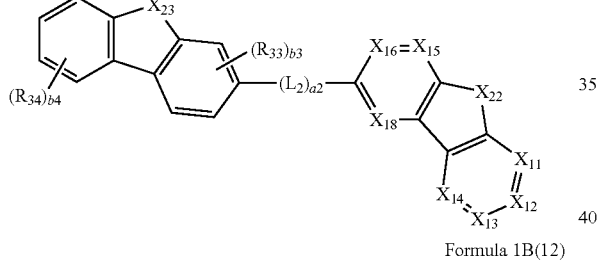
Formula 1B(12)
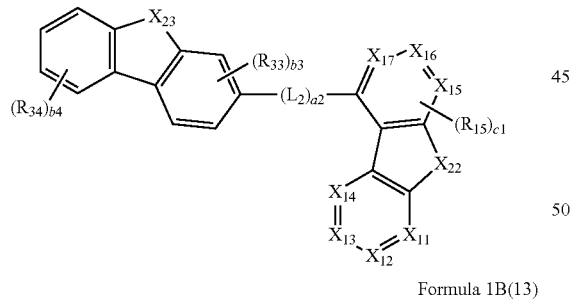
Formula 1B(13)
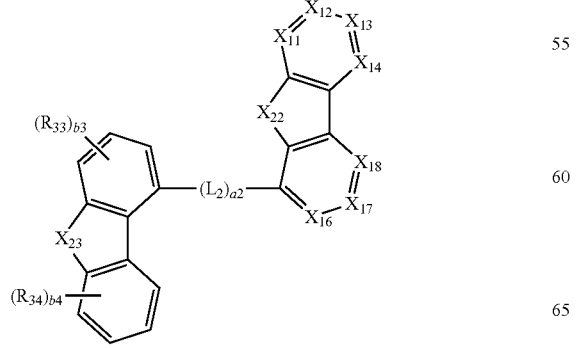
Formula 1B(14)
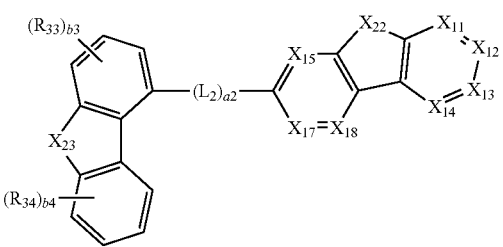
Formula 1B(15)
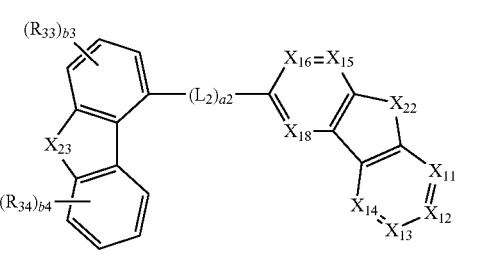
Formula 1B(16)
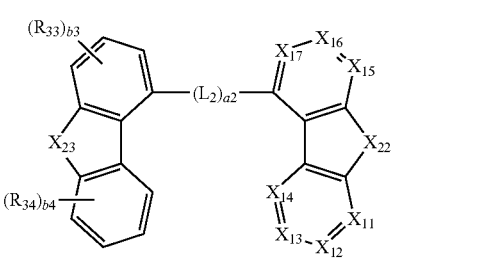
wherein, in Formulae 1B(1) to 1B(16), $X_{11}$ to $X_{18}$, $X_{22}$, $X_{23}$, $L_2$, a2, $R_{15}$, $R_{33}$, $R_{34}$, b3, and b4 are the same as in claim 1.
12. The condensed cyclic compound of claim 1, represented by one of Formulae 1B-A to 1B-P:
Formula 1B-A
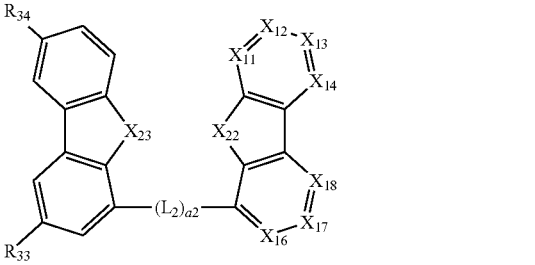
Formula 1B-B
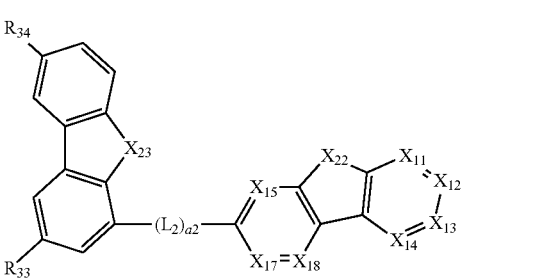

Formula 1B-C
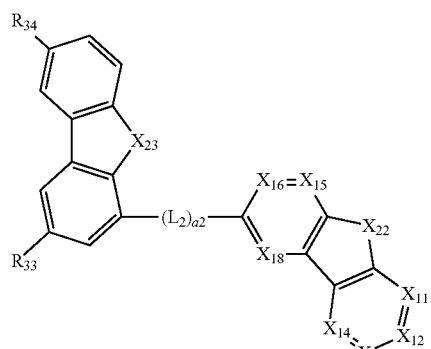
Formula 1B-D
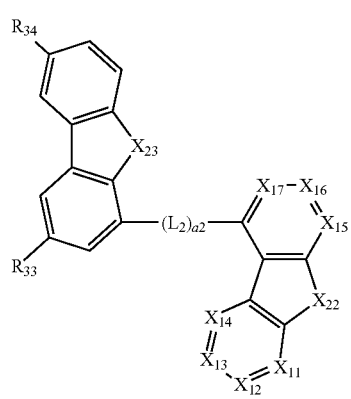
Formula 1B-E
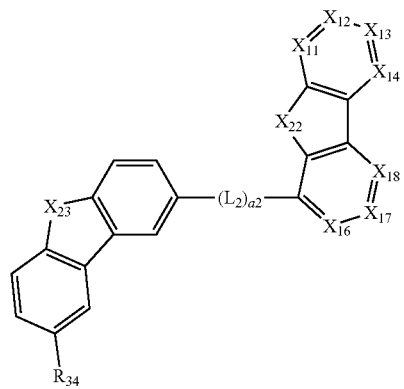
Formula 1B-F
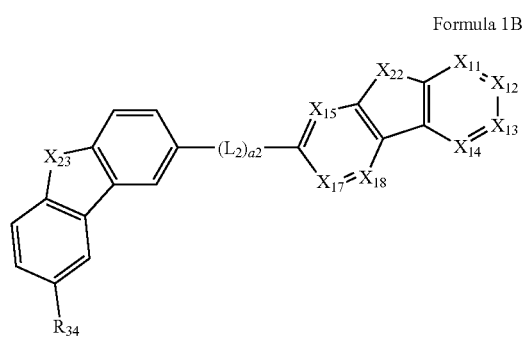
Formula 1B-G
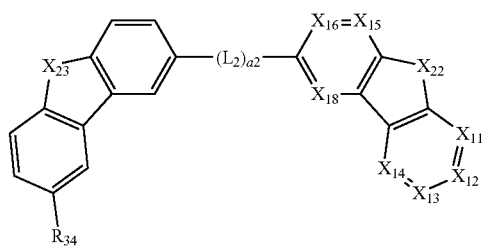
Formula 1B-H
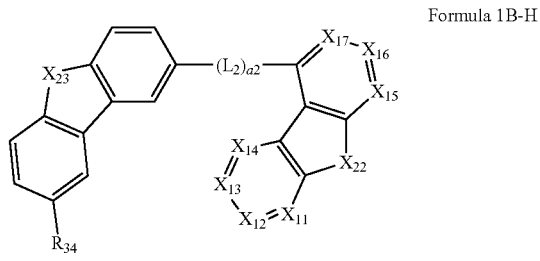
Formula 1B-I
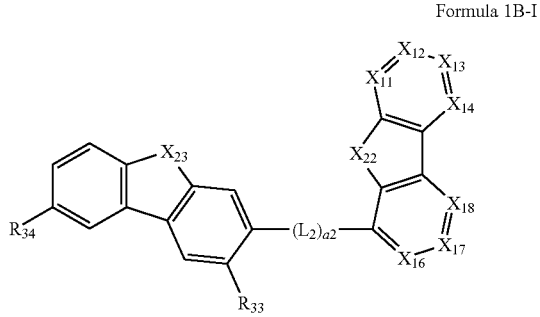
Formula 1B-J
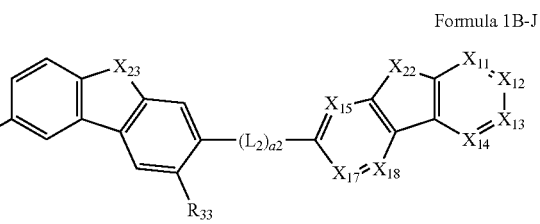
Formula 1B-K
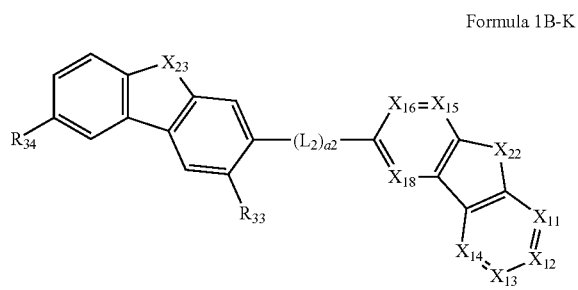
Formula 1B-L
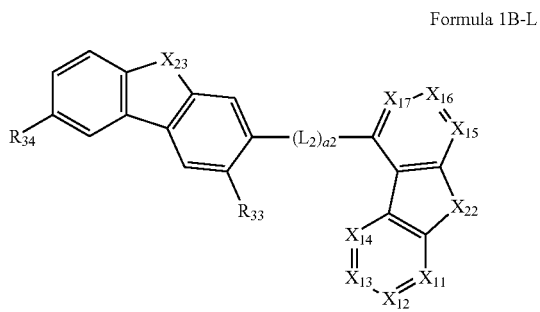

Formula 1B-M

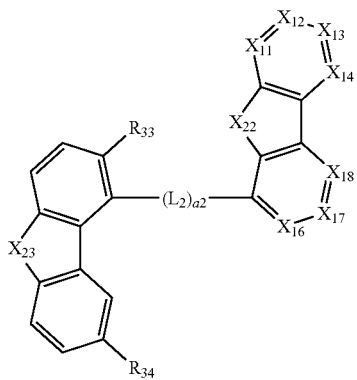

Formula 1B-N

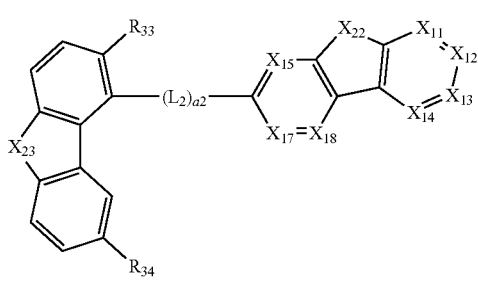

Formula 1B-O

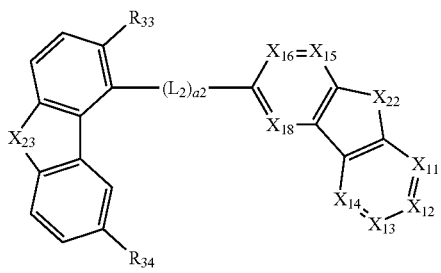

Formula 1B-P

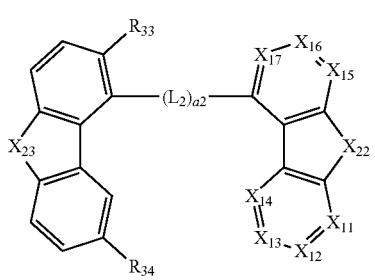

wherein, in Formulae 1B-A to 1B-P, $X_{11}$ to $X_{18}$, $X_{22}$, $X_{23}$, $L_2$, a2, $R_{33}$, and $R_{34}$ are the same as in claim 1.

13. The condensed cyclic compound of claim 1, represented by one of Formulae 1A-1 to 1A-4:

Formula 1A-1

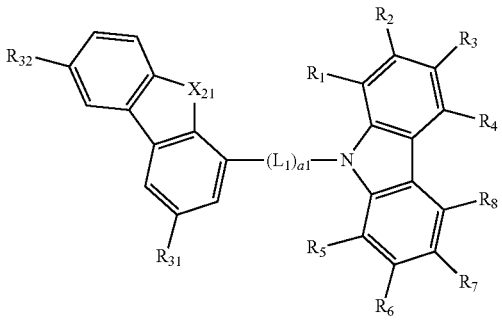

Formula 1A-2

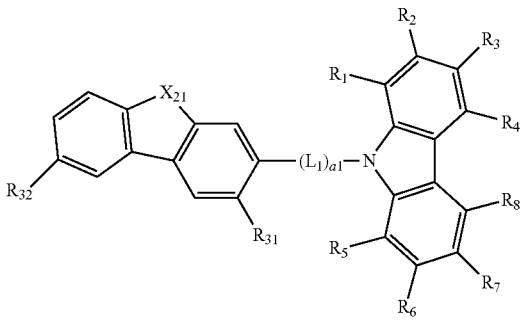

Formula 1A-3

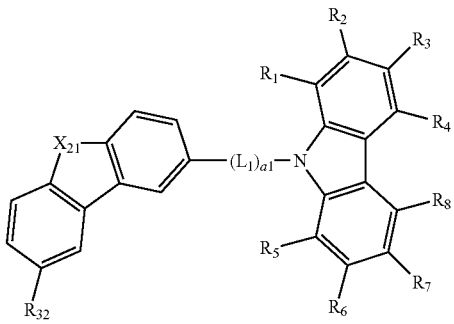

Formula 1A-4

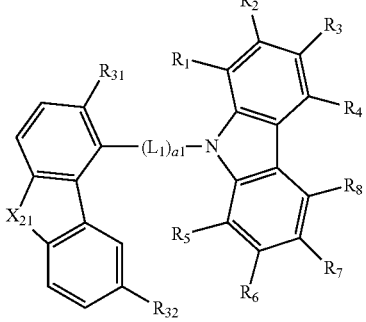

wherein, in Formulae 1A-1 to 1A-4,
$X_{21}$ is selected from O, S, $C(R_{21})(R_{22})$, and $N(R_{23})$,
wherein $R_{21}$ and $R_{22}$ are each independently selected from
a $C_1$-$C_{10}$ alkyl group and a $C_1$-$C_{10}$ alkoxy group;
a $C_1$-$C_{20}$ alkyl group and a $C_1$-$C_{20}$ alkoxy group, each substituted with at least one of a deuterium, —F, and a cyano group;
a phenyl group, a pyridinyl group, a fluorenyl group, a dibenzofuranyl group, and a dibenzothiophenyl group; and a phenyl group, a pyridinyl group, a fluorenyl group, a dibenzofuranyl group, and a dibenzothiophenyl group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group, $R_{23}$ is selected from a phenyl group, a pyridinyl group, a fluorenyl group, a dibenzofuranyl group, and a dibenzothiophenyl group; and a phenyl group, a pyridinyl group, a fluorenyl group, a dibenzofuranyl group, and a dibenzothiophenyl group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group, $L_1$ is represented by Formula 2-3 (wherein, in Formula 2-3, $Z_1$ to $Z_4$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group),

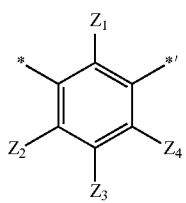

Formula 2-3 a1 is 0 or 1, $R_1$, $R_2$, $R_4$, $R_5$, $R_6$, and $R_8$ are each independently selected from a hydrogen, a deuterium, —F, a hydroxyl group, a $C_1$-$C_{10}$ alkyl group, a $C_1$-$C_{10}$ alkoxy group, a phenyl group, a pyridinyl group, a fluorenyl group, a dibenzofuranyl group, a dibenzothiophenyl group, and —Si($Q_{21}$)($Q_{22}$)($Q_{23}$), $R_3$, $R_7$, $R_{31}$, and $R_{32}$ are each independently selected from a hydrogen, a deuterium, —F, a hydroxyl group, a cyano group, a $C_1$-$C_{10}$ alkyl group, a $C_1$-$C_{10}$ alkoxy group, a phenyl group, a pyridinyl group, a fluorenyl group, a dibenzofuranyl group, a dibenzothiophenyl group, and —Si($Q_{21}$)($Q_{22}$)($Q_{23}$), wherein $Q_{21}$ to $Q_{23}$ are each independently selected from a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group, and at least one of $R_3$, $R_7$, $R_{31}$, and $R_{32}$ in Formulae 1A-1, 1A-2, and 1A-4 is a cyano group, and at least one of $R_3$, $R_7$, and $R_{32}$ in Formula 1A-3 is a cyano group.

14. The condensed cyclic compound of claim 1, represented by one of Formulae 1B-1 to 1B-4:

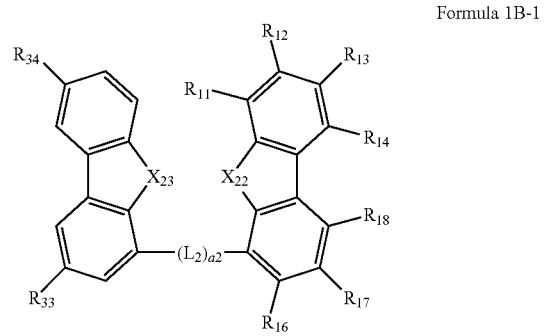

Formula 1B-1

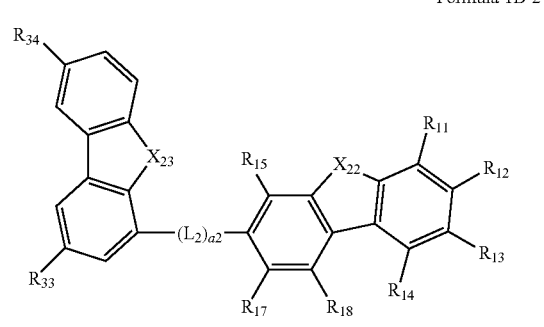

Formula 1B-2

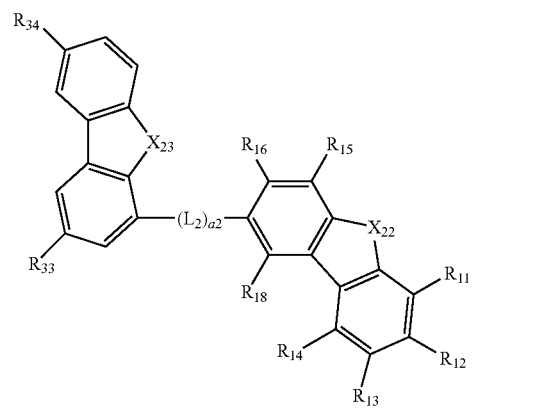

Formula 1B-3

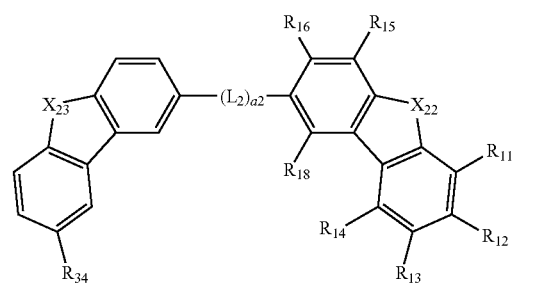

Formula 1B-4 wherein, in Formulae 1B-1 to 1B-4, $X_{22}$ is selected from O, S, C($R_{24}$)($R_{25}$), and N($R_{26}$), $X_{23}$ is selected from O, S, and C($R_{27}$)($R_{28}$), $R_{24}$, $R_{25}$, $R_{27}$, and $R_{28}$ are each independently selected from a $C_1$-$C_{10}$ alkyl group and a $C_1$-$C_{10}$ alkoxy group;

a $C_1$-$C_{20}$ alkyl group and a $C_1$-$C_{20}$ alkoxy group, each substituted with at least one of a deuterium, —F, and a cyano group;

a phenyl group, a pyridinyl group, a fluorenyl group, a dibenzofuranyl group, and a dibenzothiophenyl group; and a phenyl group, a pyridinyl group, a fluorenyl group, a dibenzofuranyl group, and a dibenzothiophenyl group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group, $R_{26}$ and $R_{29}$ are each independently selected from a phenyl group, a pyridinyl group, a fluorenyl group, a dibenzofuranyl group, and a dibenzothiophenyl group; and a phenyl group, a pyridinyl group, a fluorenyl group, a dibenzofuranyl group, and a dibenzothiophenyl group, each substituted with at least one of a deuterium, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group, $L_2$ is represented by Formula 2-3 (wherein, in Formula 2-3, $Z_1$ to $Z_4$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group), Formula 2-3

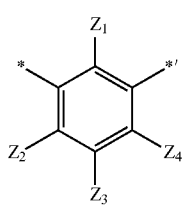

a2 is 0 or 1, $R_{11}$, $R_{12}$, $R_{14}$, $R_{15}$, $R_{16}$, and $R_{18}$ are each independently selected from a hydrogen, a deuterium, —F, a hydroxyl group, a $C_1$-$C_{10}$ alkyl group, a $C_1$-$C_{10}$ alkoxy group, a phenyl group, a pyridinyl group, a fluorenyl group, a dibenzofuranyl group, a dibenzothiophenyl group, and —Si($Q_{21}$)($Q_{22}$)($Q_{23}$), and $R_{13}$, $R_{17}$, $R_{33}$, and $R_{34}$ are each independently selected from a hydrogen, a deuterium, —F, a hydroxyl group, a cyano group, a $C_1$-$C_{10}$ alkyl group, a $C_1$-$C_{10}$ alkoxy group, a phenyl group, a pyridinyl group, a fluorenyl group, a dibenzofuranyl group, a dibenzothiophenyl group, and —Si($Q_{21}$)($Q_{22}$)($Q_{23}$), wherein $Q_{21}$ to $Q_{23}$ are each independently selected from a $C_1$-$C_{20}$ alkyl group, a $C_1$-$C_{20}$ alkoxy group, a phenyl group, a pyridinyl group, a fluorenyl group, a dibenzofuranyl group, and a dibenzothiophenyl group, and at least one of $R_{13}$, $R_{17}$, $R_{33}$, and $R_{34}$ in Formulae 1B-1 and 1B-2 is a cyano group, at least one of $R_{13}$, $R_{33}$, and $R_{34}$ in Formula 1B-3 is a cyano group, and at least one of $R_{13}$ and $R_{34}$ in Formula is a cyano group.

15. The condensed cyclic compound of claim 1, comprising at least one of Compounds 1 to 72:

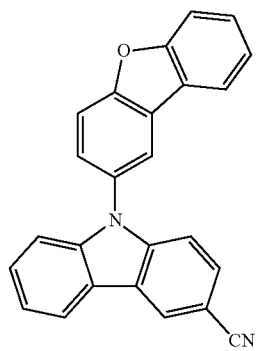

1

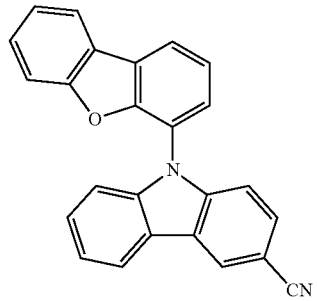

2

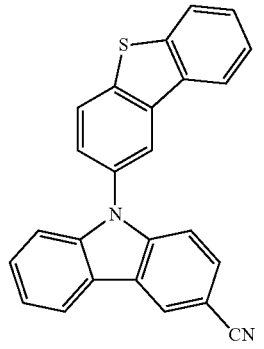

3

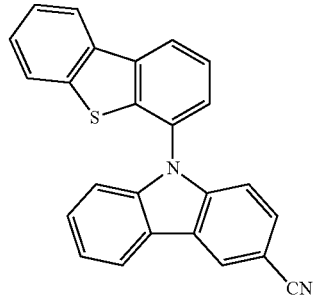

4

-continued
5
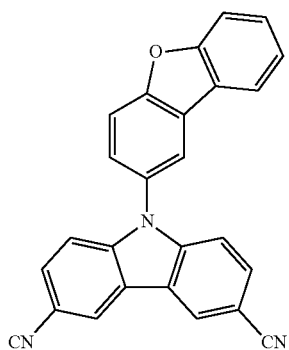
6
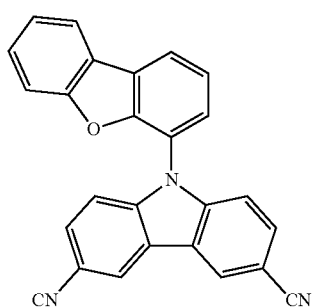
7
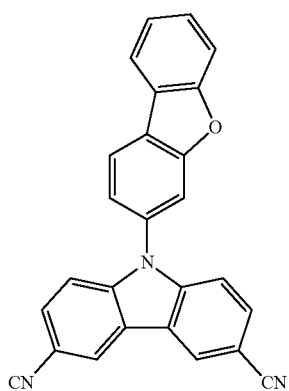
8
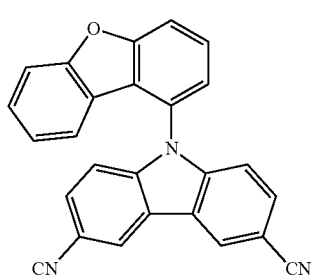
-continued
9
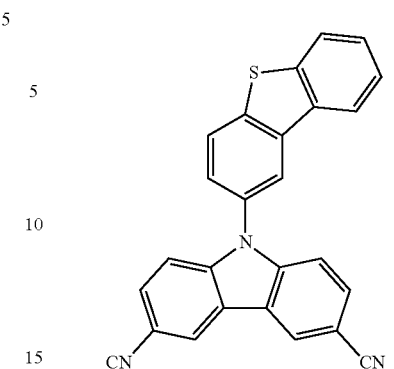
10
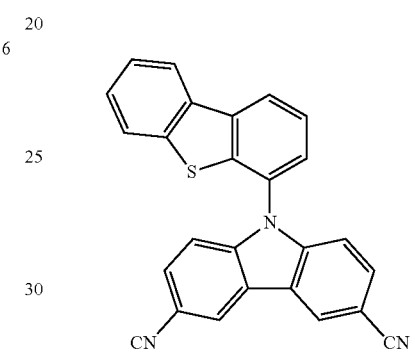
11
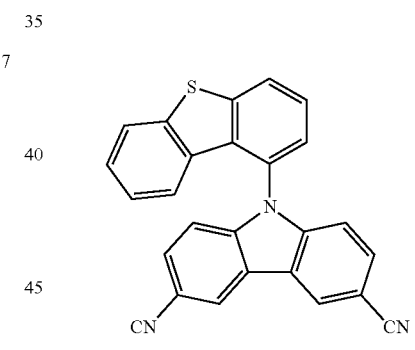
12
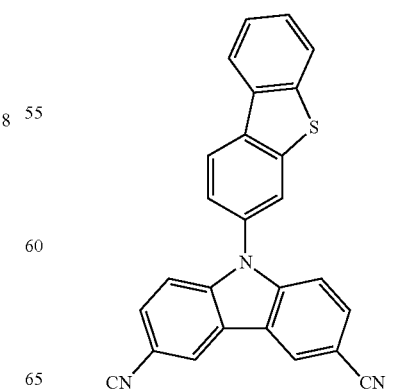

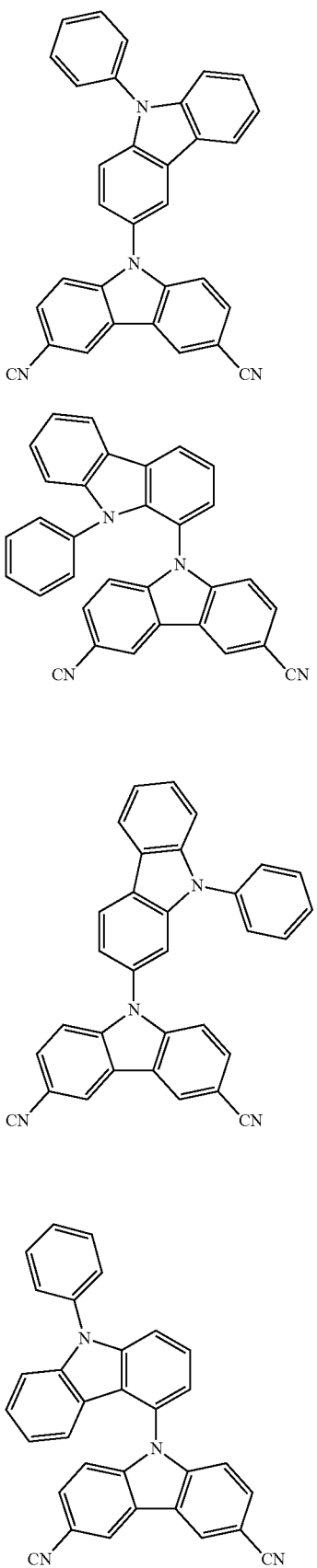
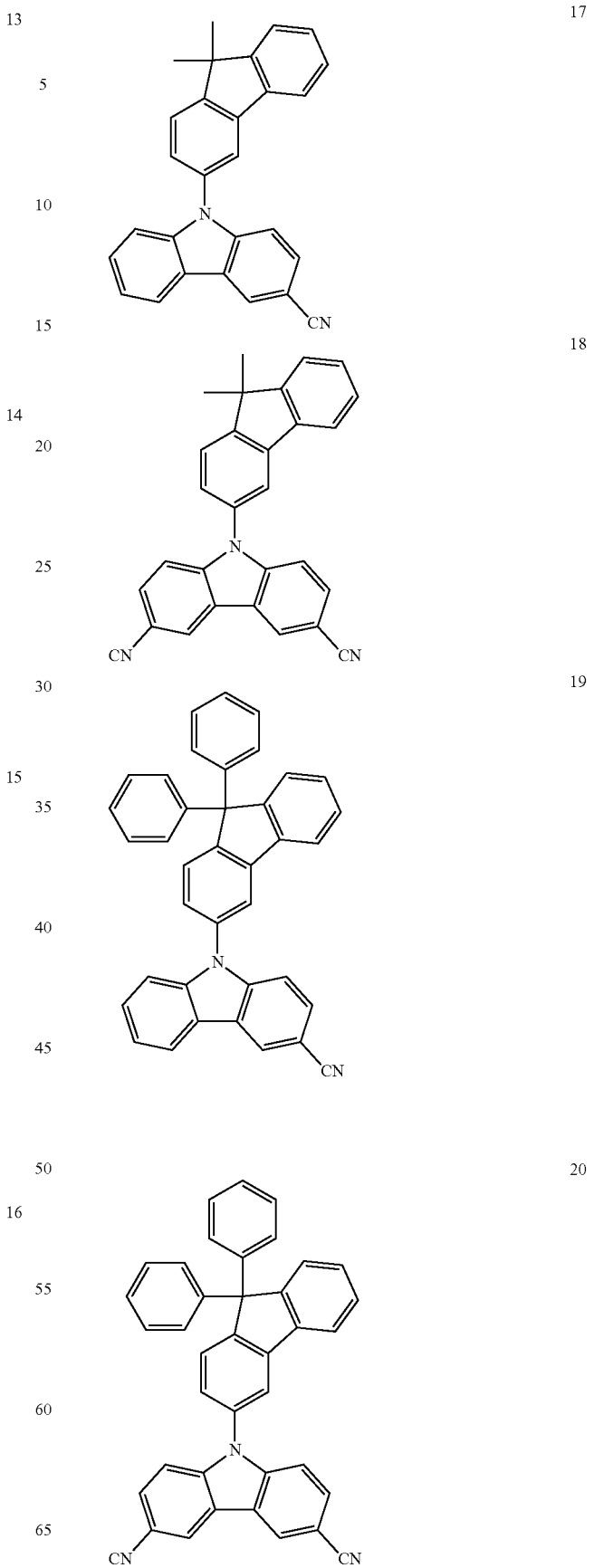

21
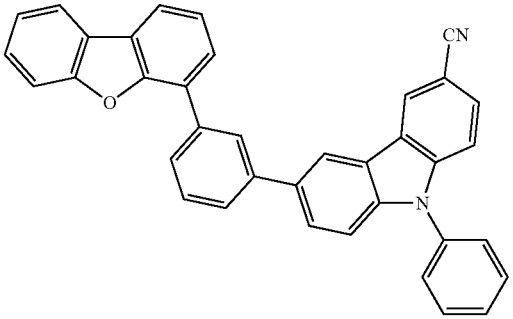
22
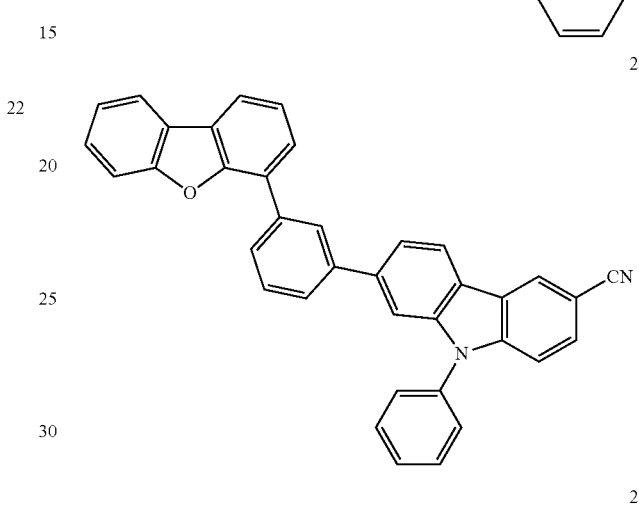
23
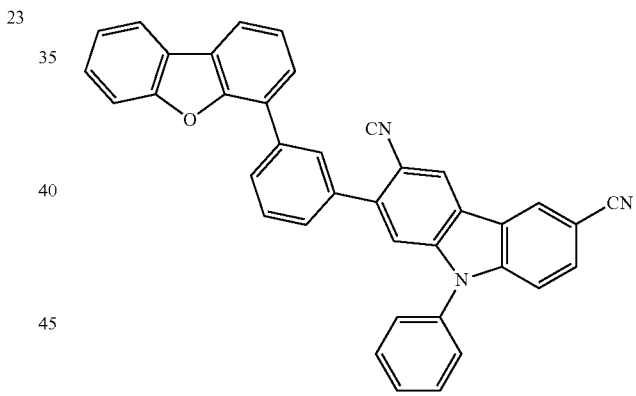
24
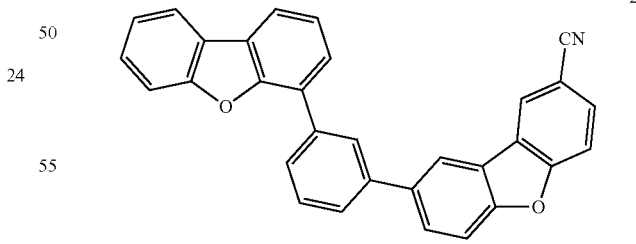
25
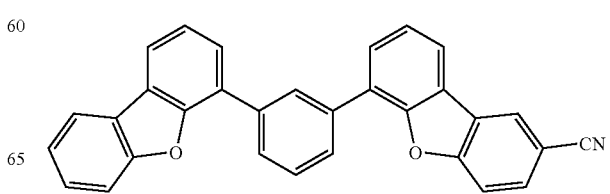
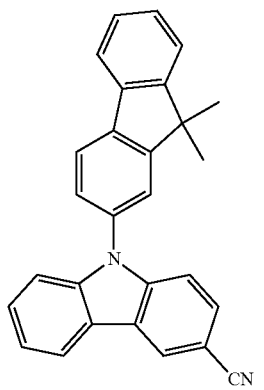
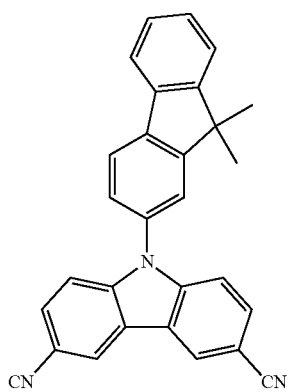
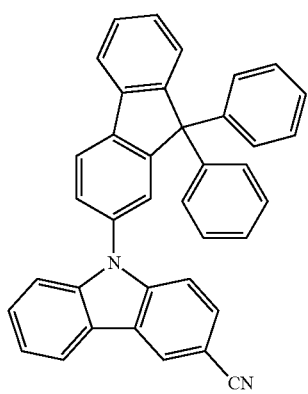
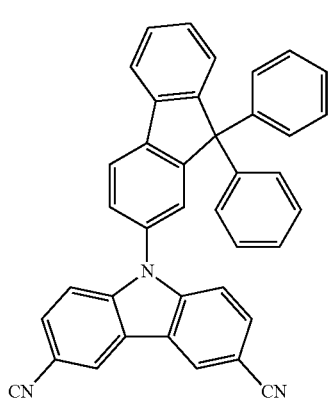

30
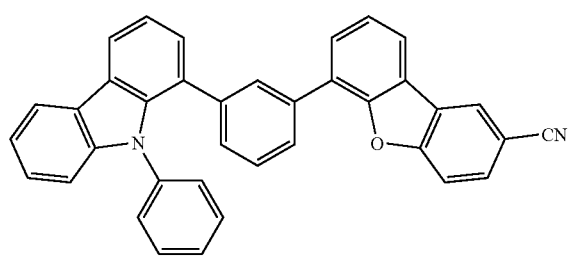
31
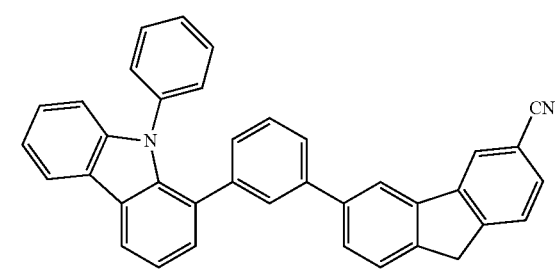
32
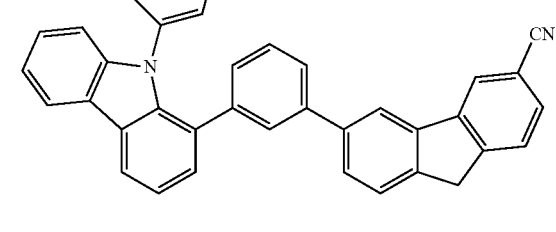
33
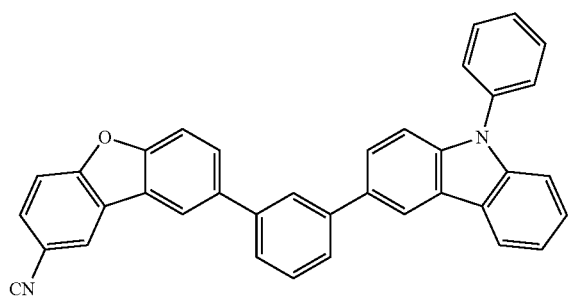
34
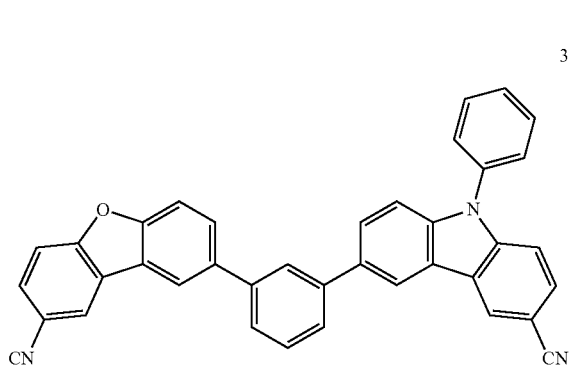
35
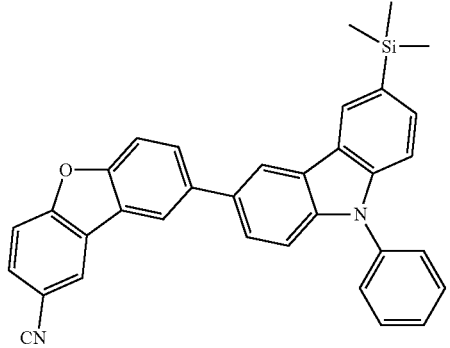
36
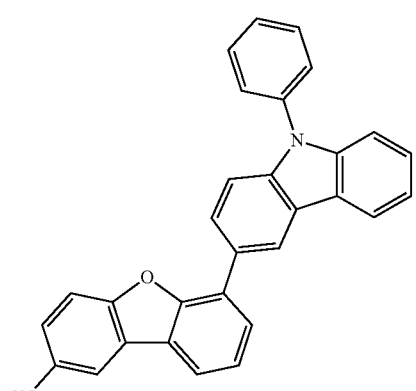
37
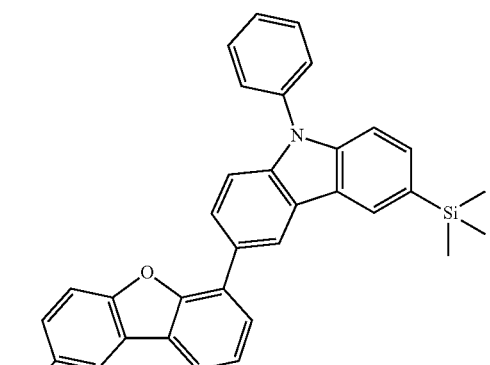
38
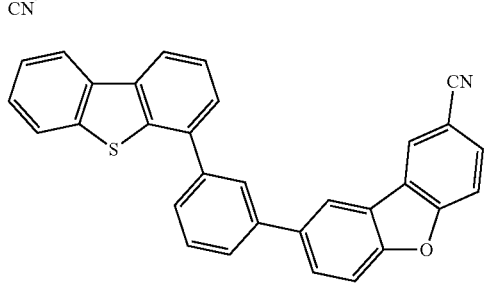
39
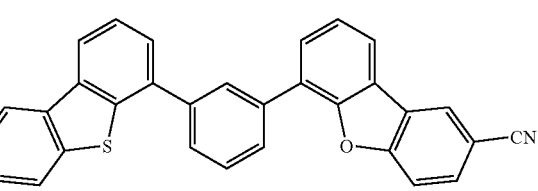

40 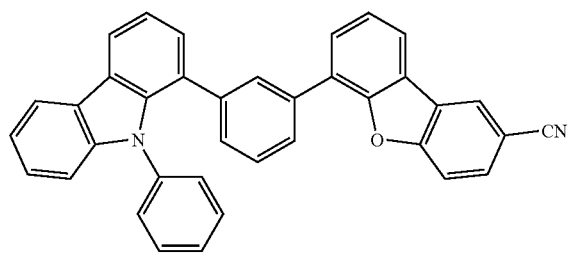
41 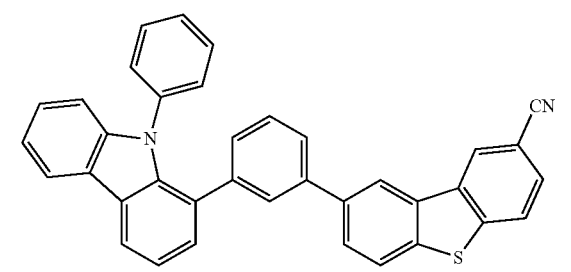
42 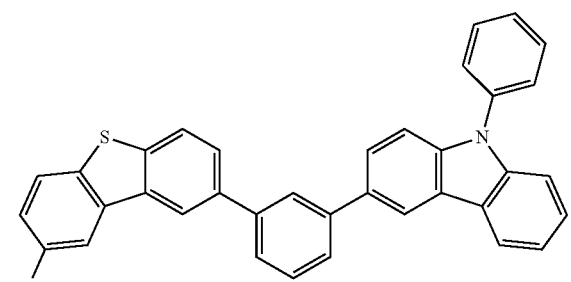
43 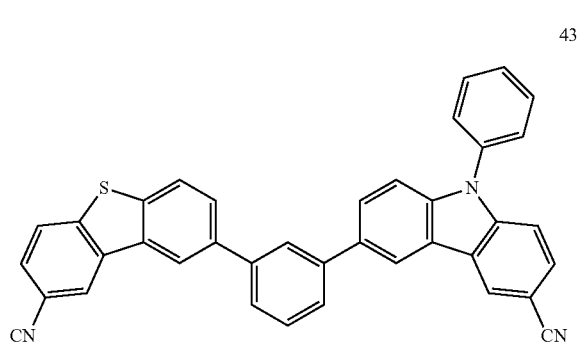
44 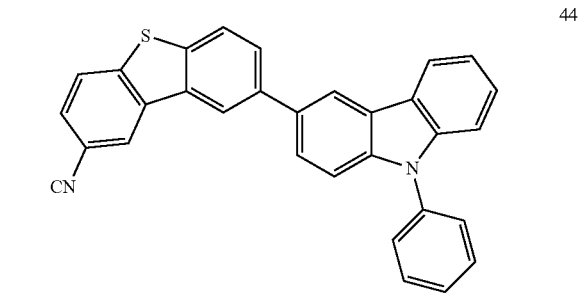
45 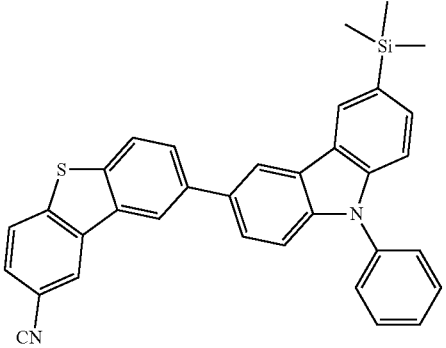
46 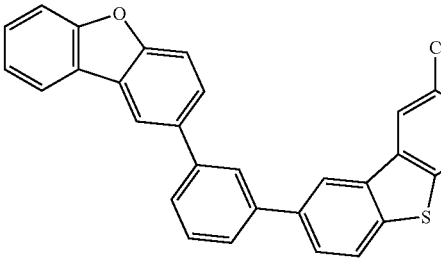
47 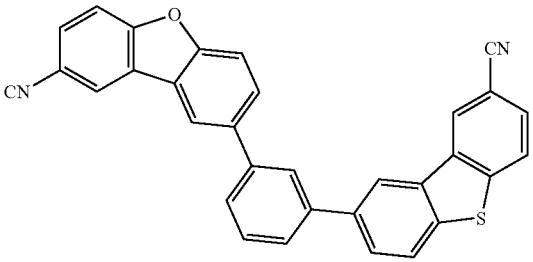
48 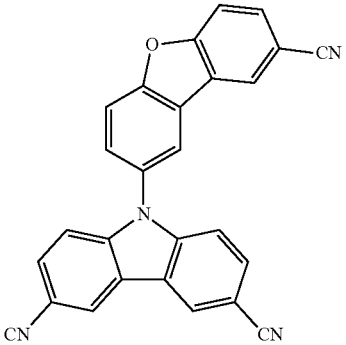
49 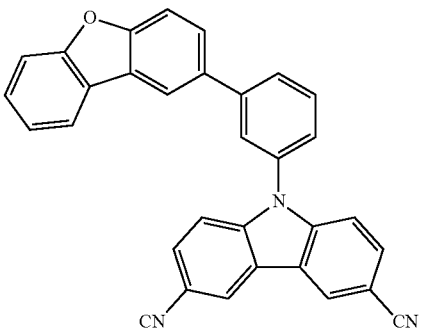

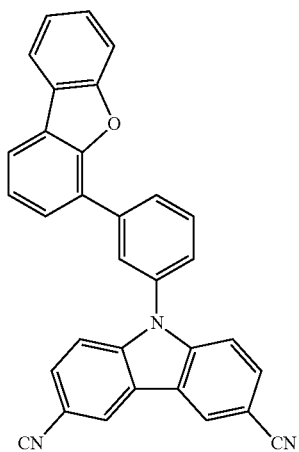
50
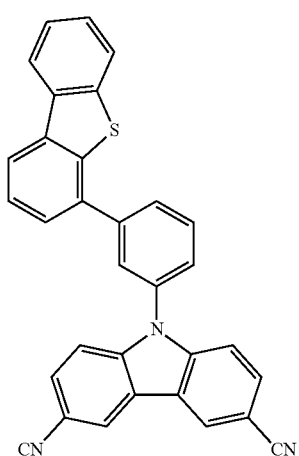
51
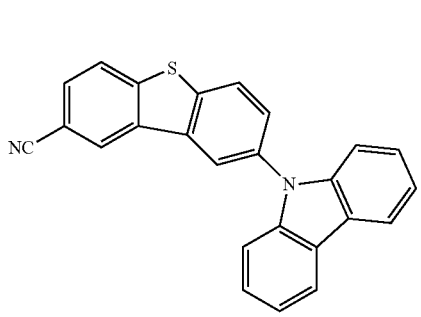
52
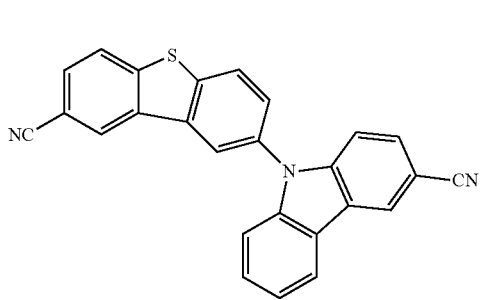
53
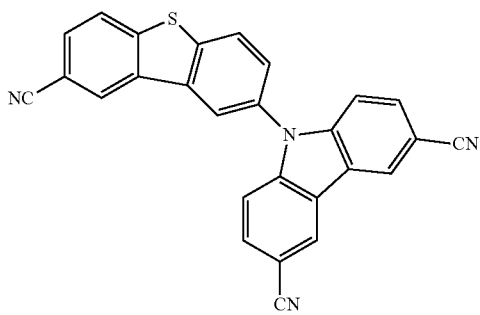
54
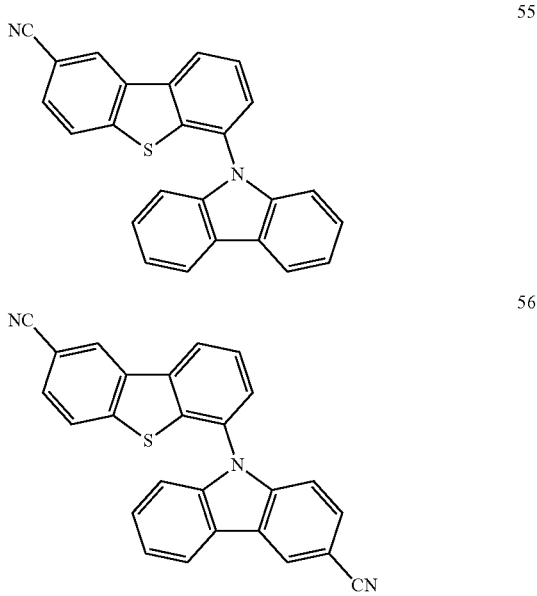
55
56
57
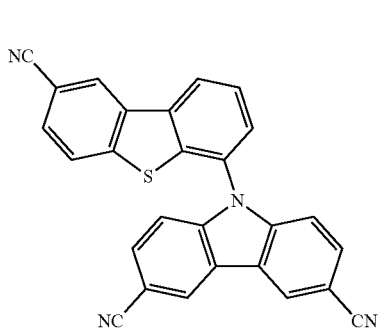
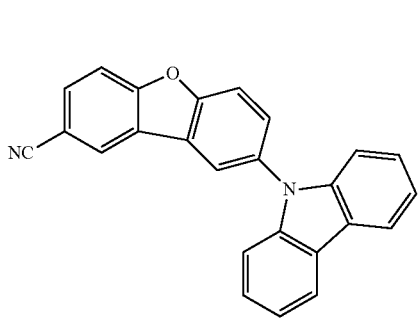
58

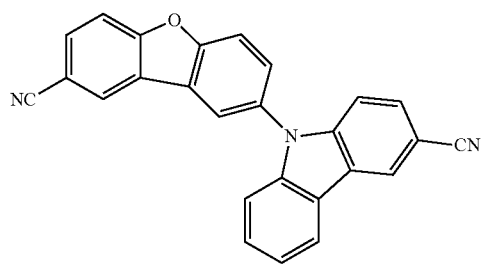
59
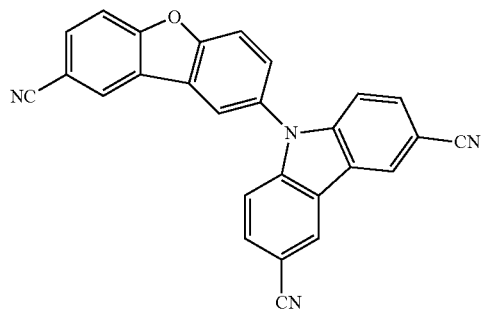
60
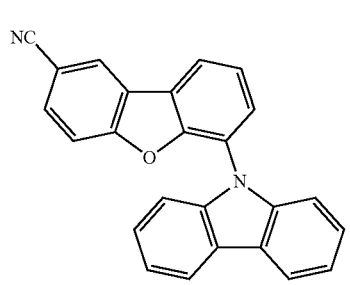
61
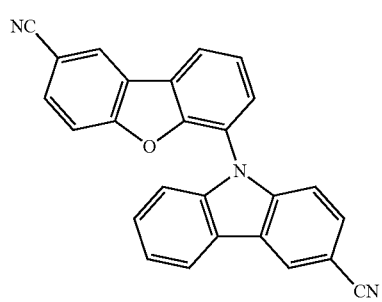
62
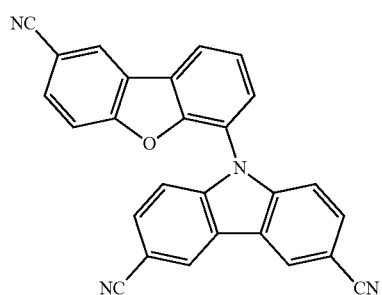
63
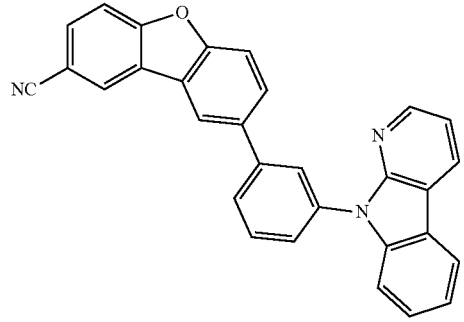
64
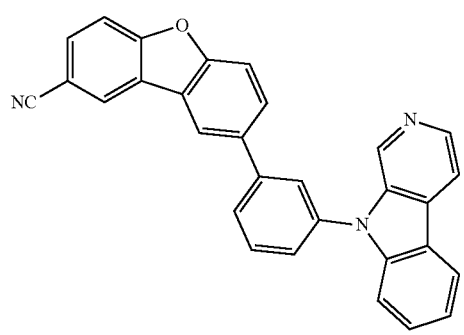
65
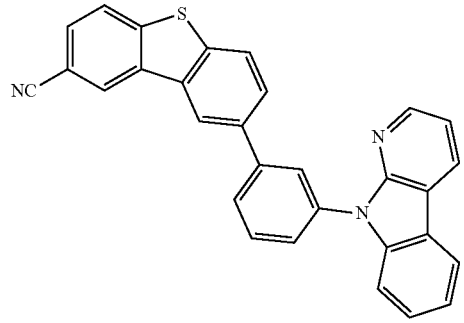
66
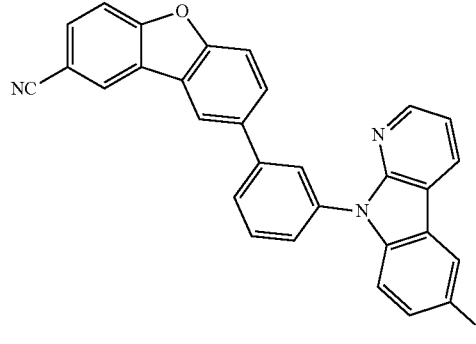
67

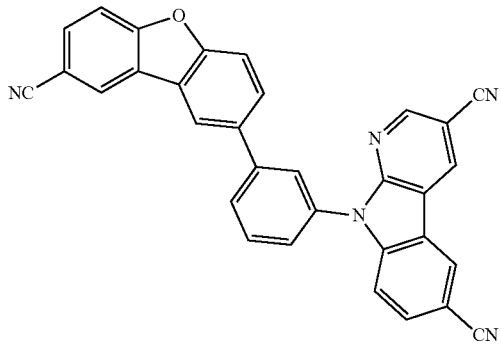
68

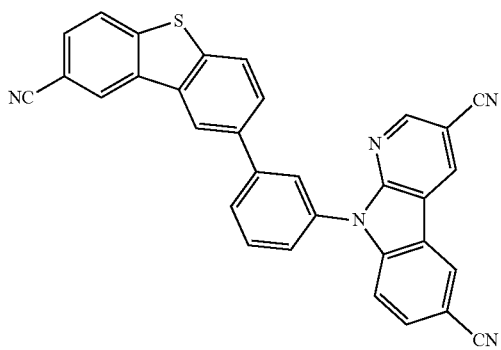
69

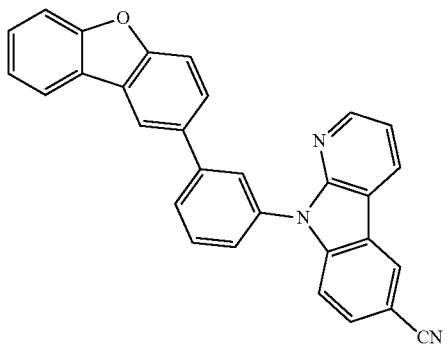
70

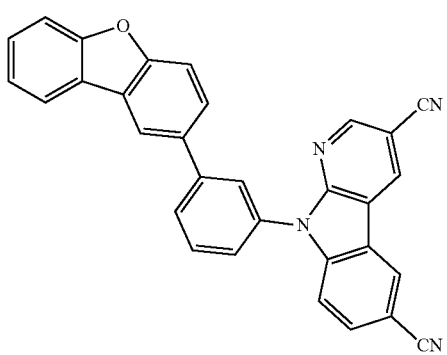
71

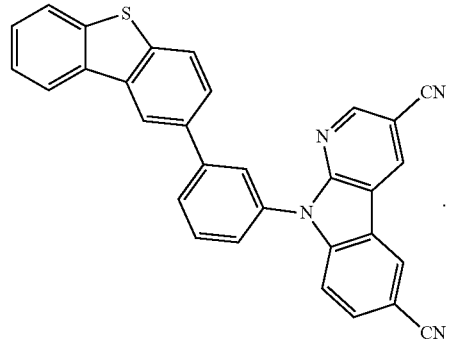
72

16. An organic light-emitting device, comprising
a first electrode;
a second electrode; and
an organic layer disposed between the first electrode and the second electrode,
wherein the organic layer comprises an emission layer, and
wherein the organic layer comprises at least one condensed cyclic compound of Formulae 1A and 1B of claim 1.

17. The organic light-emitting device of claim 16, wherein
the first electrode is an anode;
the second electrode is a cathode; and
the organic layer further comprises
i) a hole transport region disposed between the first electrode and the emission layer, wherein the hole transport region comprises at least one of a hole injection layer, a hole transport layer, and an electron blocking layer; and
ii) an electron transport region disposed between the emission layer and the second electrode, wherein the electron transport region comprises at least one of a hole blocking layer, an electron transport layer, and an electron injection layer.

18. The organic light-emitting device of claim 16, wherein the emission layer comprises the condensed cyclic compound of Formulae 1A or 1B.

19. The organic light-emitting device of claim 16, wherein the emission layer comprises the condensed cyclic compound of Formulae 1A or 1B, and further comprises a phosphorescent dopant.

20. The organic light-emitting device of claim 19, wherein the phosphorescent dopant comprises an organometallic compound represented by Formula 81:

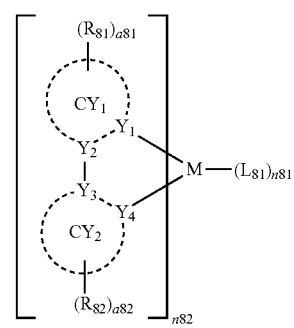

wherein, in Formula 81,

M is selected from iridium, platinum, osmium, titanium, zirconium, hafnium, europium, terbium, and thulium, $Y_1$ to $Y_4$ are each independently C or N, $Y_1$ and $Y_2$ are linked with each other by a single bond or a double bond, and $Y_3$ and $Y_4$ are linked with each other by a single bond or a double bond, $CY_1$ and $CY_2$ are each independently selected from a benzene, a naphthalene, a fluorene, a spiro-fluorene, an indene, a pyrrole, a thiophene, a furan, an imidazole, a pyrazole, a thiazole, an isothiazole, an oxazole, an isoxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzoxazole, an isobenzoxazole, a triazole, a tetrazole, an oxadiazole, a triazine, a dibenzofuran, and a dibenzothiophene, wherein $CY_1$ and $CY_2$ are optionally additionally linked with each other by an organic linking group, $R_{81}$ and $R_{82}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$), a81 and a82 are each independently an integer selected from 1 to 5, n81 is an integer selected from 0 to 4, n82 is 1, 2, or 3, and $L_{81}$ is a monovalent organic ligand, a divalent organic ligand, or a trivalent organic ligand.

* * * * *